United States Patent
Schmidt et al.

(10) Patent No.: US 8,236,715 B2
(45) Date of Patent: Aug. 7, 2012

(54) ABSORBENT STRUCTURE WITH IMPROVED WATER-ABSORBING MATERIAL

(75) Inventors: Mattias Schmidt, Idstein (DE); Axel Meyer, Frankfurt (DE); Renae Dianna Fossum, Middletown, OH (US); Jean-Philippe Marie Autran, Wyoming, OH (US); Ulrich Riegel, Landstuhl (DE); Thomas Daniel, Waldsee (DE); Stefan Bruhns, Mannheim (DE); Mark Elliott, Ludwigshafen (DE); Karl Haeberle, Speyer (DE)

(73) Assignee: The Procter & Gamble Company, Cincinnati, OH (US)

( * ) Notice: Subject to any disclaimer, the term of this patent is extended or adjusted under 35 U.S.C. 154(b) by 995 days.

(21) Appl. No.: 11/890,089

(22) Filed: Aug. 3, 2007

(65) Prior Publication Data

US 2008/0032035 A1 Feb. 7, 2008

Related U.S. Application Data

(63) Continuation of application No. PCT/US2006/002114, filed on Jan. 23, 2006.

(60) Provisional application No. 60/650,344, filed on Feb. 4, 2005, provisional application No. 60/650,291, filed on Feb. 4, 2005.

(51) Int. Cl.
*D04H 1/00* (2006.01)
(52) U.S. Cl. ............... 442/327; 427/2.31; 523/111
(58) Field of Classification Search .......... 442/327; 427/2.31; 523/111
See application file for complete search history.

(56) References Cited

U.S. PATENT DOCUMENTS

| | | | |
|---|---|---|---|
| 3,905,929 A | 9/1975 | Noll | |
| 4,092,286 A | 5/1978 | Noll et al. | |
| 4,190,566 A | 2/1980 | Noll et al. | |
| 4,541,871 A | 9/1985 | Obayashi et al. | |
| 4,666,983 A | 5/1987 | Tsubakimoto et al. | |
| 4,923,720 A * | 5/1990 | Lee et al. ............... | 427/422 |
| 5,066,745 A | 11/1991 | Engelhardt et al. | |
| 5,211,985 A | 5/1993 | Shirley, Jr. et al. | |
| 5,281,683 A | 1/1994 | Yano et al. | |
| 5,331,059 A | 7/1994 | Engelhardt et al. | |
| 5,409,771 A | 4/1995 | Dahmen et al. | |

(Continued)

FOREIGN PATENT DOCUMENTS

DE 2730514 A1 1/1979
(Continued)

OTHER PUBLICATIONS

English Translation of JP56-159232 (Dec. 1981) to Yoshitake (6 pages).*

(Continued)

*Primary Examiner* — Peter Y Choi
(74) *Attorney, Agent, or Firm* — John G. Powell; Richard L. Alexander

(57) ABSTRACT

The present invention relates to an absorbent structure suitable in, or being an adult or infant diaper or feminine hygiene article, comprising a water-absorbing material comprising water-absorbing particles that comprise a film coating, comprising an elastic film-forming polymer and a coalescing agent.

The invention also relates to an absorbent structure comprising a water absorbent material obtainable by a process of:
  a) spray-coating water-absorbing polymeric particles with an elastic film-forming polymer in a fluidized bed reactor at a temperature in the range from 0° C. to 150° C. and
  b) heat-treatment of the coated polymeric particles at a temperature above 50° C., wherein in step a) and/or b) a coalescing agent is added.

11 Claims, 2 Drawing Sheets

U.S. PATENT DOCUMENTS

| | | | |
|---|---|---|---|
| 5,453,323 A | | 9/1995 | Chambers et al. |
| 5,459,197 A | * | 10/1995 | Schwindt et al. ............ 524/591 |
| 5,532,323 A | | 7/1996 | Yano et al. |
| 5,562,646 A | | 10/1996 | Goldman et al. |
| 5,574,121 A | | 11/1996 | Irie et al. |
| 5,624,967 A | | 4/1997 | Hitomi et al. |
| 5,700,867 A | | 12/1997 | Ishiyama et al. |
| 5,731,365 A | | 3/1998 | Engelhardt et al. |
| 5,836,929 A | | 11/1998 | Plischke et al. |
| 5,837,789 A | | 11/1998 | Stockhausen et al. |
| 5,851,672 A | | 12/1998 | Wang et al. |
| 6,143,821 A | | 11/2000 | Houben |
| 6,241,928 B1 | | 6/2001 | Hatsuda et al. |
| 6,245,051 B1 | * | 6/2001 | Zenker et al. ............ 604/385.23 |
| 6,265,488 B1 | | 7/2001 | Fujino et al. |
| 6,300,423 B1 | | 10/2001 | Engelhardt et al. |
| 6,472,478 B1 | | 10/2002 | Funk et al. |
| 6,503,979 B1 | | 1/2003 | Funk et al. |
| 6,559,239 B1 | | 5/2003 | Riegel et al. |
| 6,657,015 B1 | | 12/2003 | Riegel et al. |
| 6,710,141 B1 | | 3/2004 | Heide et al. |
| 6,809,158 B2 | | 10/2004 | Ikeuchi et al. |
| 6,911,499 B1 | | 6/2005 | Brehm et al. |
| 6,979,564 B2 | | 12/2005 | Glucksmann et al. |
| 7,183,360 B2 | | 2/2007 | Daniel et al. |
| 7,183,456 B2 | | 2/2007 | Hatsuda et al. |
| 7,259,212 B2 | | 8/2007 | Popp et al. |
| 2003/0148684 A1 | | 8/2003 | Cramer et al. |
| 2003/0195293 A1 | | 10/2003 | Lubnin |
| 2004/0097895 A1 | | 5/2004 | Busam et al. |
| 2004/0162536 A1 | | 8/2004 | Becker et al. |
| 2004/0214937 A1 | | 10/2004 | Miller et al. |
| 2005/0008839 A1 | | 1/2005 | Cramer et al. |
| 2005/0031868 A1 | | 2/2005 | Fossum |
| 2005/0031872 A1 | | 2/2005 | Schmidt |
| 2005/0043474 A1 | | 2/2005 | Schmidt |
| 2005/0245684 A1 | | 11/2005 | Daniel et al. |
| 2006/0155057 A1 | | 7/2006 | Hermeling et al. |
| 2006/0167215 A1 | | 7/2006 | Hermeling et al. |
| 2006/0211828 A1 | | 9/2006 | Daniel et al. |
| 2006/0212011 A1 | | 9/2006 | Popp et al. |
| 2006/0235141 A1 | | 10/2006 | Riegel et al. |
| 2007/0160539 A1 | | 7/2007 | Friedman et al. |
| 2007/0203289 A1 | | 8/2007 | Bruchmann et al. |

FOREIGN PATENT DOCUMENTS

| | | | |
|---|---|---|---|
| DE | | 10204937 A | 8/2003 |
| DE | | 10355401 A1 | 6/2005 |
| EP | | 0 300 571 | 1/1989 |
| EP | | 0 612 533 | 8/1994 |
| EP | | 0 618 005 | 10/1994 |
| EP | | 0 705 643 | 4/1996 |
| JP | | 56159232 A * | 12/1981 |
| WO | | WO 90/15830 A1 | 12/1990 |
| WO | | WO 93/21237 A1 | 10/1993 |
| WO | | WO 96/14885 | 5/1996 |
| WO | | WO 01/45758 A1 | 6/2001 |
| WO | | WO 03/043670 | 5/2003 |
| WO | | WO 2004/071340 A2 | 8/2004 |
| WO | | WO 2004/071341 A2 | 8/2004 |
| WO | | WO 2004/071342 A2 | 8/2004 |
| WO | | WO 2005/014065 | 2/2005 |
| WO | | WO 2005/014067 A1 | 2/2005 |
| WO | | WO 2005/014697 A1 | 2/2005 |
| WO | | WO 2006/042704 | 4/2006 |

OTHER PUBLICATIONS

PCT Search Report, mailed Sep. 25, 2006, 4 pages.

* cited by examiner

ABSORBENT STRUCTURE WITH IMPROVED WATER-ABSORBING MATERIAL

CROSS REFERENCE TO RELATED APPLICATIONS

This application is a continuation application of prior copending International Application No. PCT/US2006/002114, filed Jan. 23, 2006, designating the U.S., which claims the benefit of U.S. Provisional Application No. 60/650,344, filed Feb. 4, 2005, and U.S. Provisional Application No. 60/650,291, filed Feb. 4, 2005, the substances of which are incorporated herein by reference.

FIELD OF THE INVENTION

This invention relates to improved absorbent structures containing improved water-absorbing material having a specific coating of elastic, film-forming polymers and/or which are made by a specific coating process. Typically, said absorbent structure is, or is suitable in (for example as absorbent core), an adult incontinence article (diaper) or infant diaper, including training or pull-on pants, or feminine hygiene article or catamenial devices, such as sanitary napkins.

BACKGROUND OF THE INVENTION

An important component of disposable absorbent articles such as diapers is an absorbent core structure comprising water-absorbing polymers, typically hydrogel-forming water-absorbing polymers, also referred to as absorbent gelling material, AGM, or super-absorbent polymers, or SAP's. This polymer material ensures that large amounts of bodily fluids, e.g. urine, can be absorbed by the article during its use and locked away, thus providing low rewet and good skin dryness.

Especially useful water-absorbing polymers or SAP's are often made by initially polymerizing unsaturated carboxylic acids or derivatives thereof, such as acrylic acid, alkali metal (e.g., sodium and/or potassium) or ammonium salts of acrylic acid, alkyl acrylates, and the like in the presence of relatively small amounts of di- or poly-functional monomers such as N,N'-methylenebisacrylamide, trimethylolpropane triacrylate, ethylene glycol di(meth)acrylate, or triallylamine. The di- or poly-functional monomer materials serve to lightly cross-link the polymer chains thereby rendering them water-insoluble, yet water-absorbing. These lightly crosslinked absorbent polymers contain a multiplicity of carboxylate groups attached to the polymer backbone. It is generally believed that the neutralized carboxylate groups generate an osmotic driving force for the absorption of body fluids by the crosslinked polymer network. In addition, the polymer particles are often treated as to form a surface cross-linked layer on the outer surface in order to improve their properties in particular for application in baby diapers, adult incontinence articles and fem-care articles.

Water-absorbing (hydrogel-forming) polymers useful as absorbents in absorbent members and articles such as disposable diapers need to have adequately high absorption capacity, as well as adequately high gel strength. Absorption capacity needs to be sufficiently high to enable the absorbent polymer to absorb significant amounts of the aqueous body fluids encountered during use of the absorbent article. Together with other properties of the gel, gel strength relates to the tendency of the swollen polymer particles to resist deformation under an applied stress. The gel strength needs to be high enough in the absorbent member or article so that the particles do not deform and fill the capillary void spaces to an unacceptable degree causing so-called gel blocking. This gel-blocking inhibits the rate of fluid uptake or the fluid distribution, i.e. once gel-blocking occurs, it can substantially impede the distribution of fluids to relatively dry zones or regions in the absorbent article and leakage from the absorbent article can take place well before the water-absorbing polymer particles are fully saturated or before the fluid can diffuse or wick past the "gel blocking" particles into the rest of the absorbent article. Thus, it is important that the water-absorbing polymers (when incorporated in an absorbent structure or article) maintain a high wet-porosity and have a high resistance against deformation thus yielding high permeability for fluid transport through the swollen gel bed. On the other side it is also beneficial that the swollen gel bed has narrow pores in order to allow efficient fluid distribution by wicking mechanisms.

Absorbent polymers with relatively high permeability can be made by increasing the level of internal crosslinking or surface crosslinking, which increases the resistance of the swollen gel against deformation by an external pressure such as the pressure caused by the wearer, but this typically also reduces the absorbent capacity of the gel which is undesirable. It is a significant draw back of this conventional approach that the absorbent capacity has to be sacrificed in order to gain permeability. The lower absorbent capacity must be compensated by a higher dosage of the absorbent polymer in hygiene articles which for example leads to difficulties with the core integrity of a diaper during wear. Hence, special, technically challenging and expensive fixation technologies are required to overcome this issue in addition to the higher costs that are incurred because of the required higher absorbent polymer dosing level.

Because of the trade-off between absorbent capacity and permeability in the conventional approach, it is extremely difficult to produce absorbent polymers that show improved properties regarding absorbent capacity and permeability versus what is described by the following empirical relation:

$$\mathrm{Log}(CS\text{-}SFC'/150) \leq 3.36 - 0.133 \times CS\text{-}CRC \qquad (1)$$

and it is even more difficult to produce absorbent polymers that show improved properties regarding absorbent capacity and permeability versus what is described by the following empirical relation:

$$\mathrm{Log}(CS\text{-}SFC'/150) \leq 2.5 - 0.095 \times CS\text{-}CRC \qquad (2)$$

It is therefore very desirable to produce absorbent polymers that fulfil the following relations (3) or (4) or preferred (3) and (4):

$$\mathrm{Log}(CS\text{-}SFC'/150) > 3.36 - 0.133 \times CS\text{-}CRC \qquad (3)$$

$$\mathrm{Log}(CS\text{-}SFC'/150) > 2.5 - 0.095 \times CS\text{-}CRC \qquad (4)$$

In all relations above, CS-SFC'=CS-SFC×$10^7$ and the dimension of 150 is [cm$^3$ s/g].

If in the relations (1) through (4) above the CS-CRC is replaced with the CCRC as defined herein, all of the relations remain valid. It is therefore particularly desirable to produce absorbent polymers that fulfil the following relations (5) or (6):

$$\mathrm{Log}(CS\text{-}SFC'/150) > 3.36 - 0.133 \times CCRC \qquad (5)$$

$$\mathrm{Log}(CS\text{-}SFC'/150) > 2.5 - 0.095 \times CCRC \qquad (6)$$

In relations (5) and (6) above, CS-SFC'=CS-SFC×107 and the dimension of 150 is [cm$^3$ s/g]. Log is the logarithm to the basis 10.

Often the surface cross linked water-absorbing polymer particles are constrained by the surface-cross linked shell and cannot absorb and swell sufficiently, and/or the surface-cross linked shell is not strong enough to withstand the stresses of swelling or the stresses associated with performance under load.

As a result thereof the coatings or shells of the water-absorbing polymers, as used in the art, including surface cross-linking 'coatings', break when the polymer swells significantly or it has been in a swollen state for a period of time. Often the coated and/or surface-cross linked water-absorbing polymers or super-absorbent materials known in the art deform significantly in use thus leading to relatively low porosity and permeability of the gel bed in the wet state.

The present invention thus has for its objective to provide absorbent structures with improved water-absorbing material having a more advantageous modification of the surface whose integrity is preserved during the swelling and preferably also during the lifetime of the hygiene article manufactured using this absorbent polymer, and/or such water-absorbing materials obtainable by a specific improved process that provides for these improved properties.

EP-A-0 703 265 teaches the treatment of hydrogel with film-forming polymers such as acrylic/methacrylic acid dispersions to produce abrasion-resistant absorbents. The treating agents identified include polyurethanes. However, the absorbent particles obtained therein give unsatisfactory absorption values, especially with regard to CCRC, CS-CRC and CS-SFC. More particularly, the reference cited does not teach how to produce uniform coatings that retain their mechanical properties to a sufficient degree during swelling and during use.

The older PCT-applications WO 2005/014697, WO 2005/014067, US 2005/031868, US 2005/031872 and US 2005/043474 teach the spray-coating of hydrogel with elastic-film-forming polymers in a fluidized bed reactor. However, there is no teaching about adding an antioxidant. There is no teaching on the optimum annealing time in the heat treatment step and there is no teaching on advantageous coalescing agents.

In general, the handling of water-absorbing polymeric particles at higher temperatures is done under an inert gas or a vacuum is applied to reduce performance losses of the hydrogel. Both results in a high apparative effort. Another possibility is to work at lower temperatures, which results in longer reaction time and a low production output. The objective of the invention accordingly is to provide a process for producing water absorbing polymeric particles with a good space-time yield. It is an objective of the invention to provide a process with a short heat-treatment step. It is a further objective of the invention to provide a method for determination of the optimum heat-treatment time and to provide a process for production of performance optimized water-absorbing polymeric particles.

The objective of this invention accordingly is to provide absorbent structures with water-absorbing polymeric particles having high core shell centrifuge retention capacity (CS-CRC), high core shell absorbency under load (CS-AUL) and high core shell saline flow conductivity (CS-SFC), the water-absorbing polymers having to have high core shell saline flow conductivity (CS-SFC) in particular.

The objective of this invention accordingly is to provide absorbent structures with water-absorbing polymeric particles having high cylinder centrifuge retention capacity (CCRC), high core shell absorbency under load (CS-AUL) and high core shell saline flow conductivity (CS-SFC), the water-absorbing polymers having to have high core shell saline flow conductivity (CS-SFC) in particular.

SUMMARY OF THE INVENTION

The present invention relates to an absorbent structure suitable in, or being an adult or infant diaper or feminine hygiene article, comprising a water-absorbing material comprising water-absorbing particles that comprise a film coating, comprising an elastic film-forming polymer and a coalescing agent.

The invention also relates to an absorbent structure comprising a water-absorbing material obtainable by a process of:
  a) spray-coating water-absorbing polymeric particles with an elastic film-forming polymer in a fluidized bed reactor at a temperature in the range from 0° C. to 150° C. and
  b) heat-treatment of the coated polymeric particles at a temperature above 50° C.,
  wherein in step a) and/or b) a coalescing agent is added.

The elastic film-forming polymer is preferably a polyurethane polymer, as described herein.

Preferred absorbent structures include adult and infant diapers and absorbent cores thereof.

DETAILED DESCRIPTION OF THE INVENTION

Absorbent Structures

Figure 1:
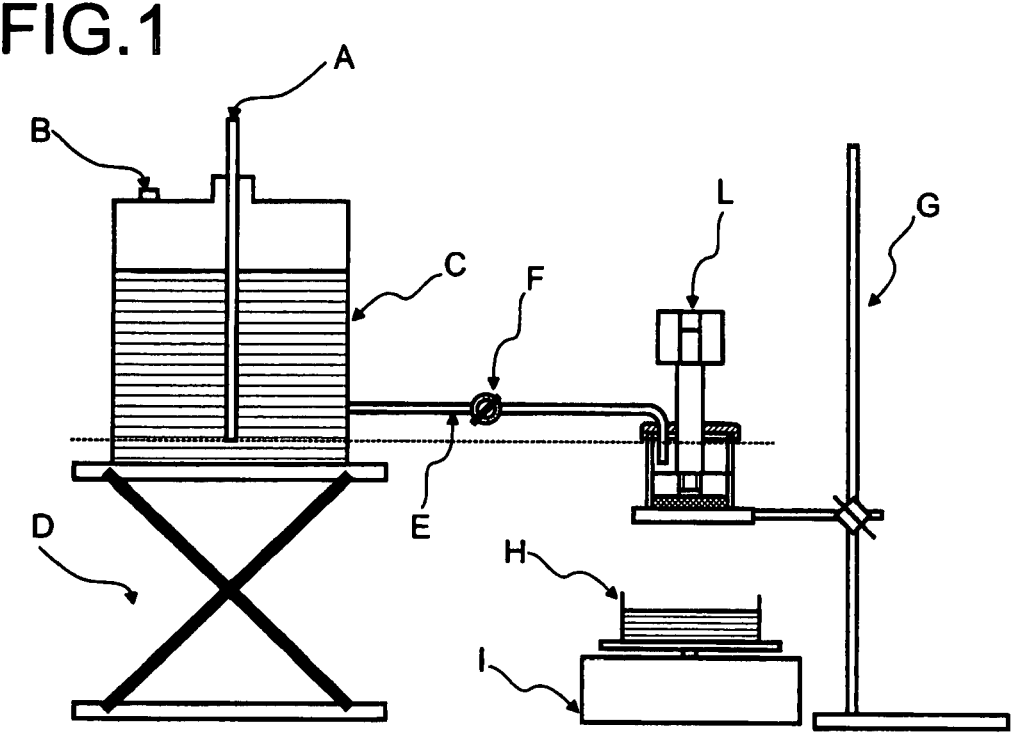
FIG. 1 is a schematic view of the permeability equipment setup.

"Absorbent structure" refers to any three dimensional structure, comprising water-absorbing material, useful to absorb and retain liquids, such as urine, menses or blood. As described herein the absorbent structure of the invention may be absorbent article, such as a diaper, feminine hygiene article, or the absorbent structure may be a structure, e.g. absorbent core, suitable for incorporation into such an article.

"Absorbent article" refers to devices that absorb and retain liquids (such as blood, menses and urine), and more specifically, refers to devices that are placed against or in proximity to the body of the wearer to absorb and contain the various exudates discharged from the body. Absorbent articles include but are not limited to infant diapers, including training pants, adult incontinence diapers (including briefs), diaper holders and liners, feminine hygiene articles, including sanitary napkins and the like.

"Diaper" refers to an absorbent article generally worn by infants and incontinent persons about the lower torso.

"Disposable" is used herein to describe articles that are generally not intended to be laundered or otherwise restored or reused (i.e., they are intended to be discarded after a single use and, preferably, to be recycled, composted or otherwise disposed of in an environmentally compatible manner).

"Inert gases" as used herein are materials which are in gaseous form under the respective reaction conditions and which, under these conditions, do not have an oxidizing effect on the constituents of the reaction mixture or on the polymer, and also mixtures of these gases. Useful inert gases include for example nitrogen, carbon dioxide, argon or steam, and nitrogen is preferred.

The absorbent structure typically comprises the water-absorbing material herein and a structuring material, such as a core wrap or wrapping material, support layer for the water-absorbing material or structuring agent such as described below.

The absorbent structure is or forms part of an absorbent article, and preferably disposable absorbent articles, such as preferably sanitary napkins, panty liners, and more preferably adult incontinence products, diapers, and training pants.

If the absorbent structure is part of a disposable absorbent article, then the absorbent structure of the invention is typically that part of an absorbent article which serves to store and/or acquire bodily fluids, the absorbent structure may be the storage layer of an absorbent article, or the acquisition layer, or both, either as two or more layers or as unitary structure.

The absorbent structure may be a structure that consists of the water-absorbing material and that is then shaped into the required three-dimensional structure, or preferably, it may comprise additional components, such as those used in the art for absorbent structures.

If the absorbent structure herein is an absorbent component (core) for an absorbent article, it may be preferred that the absorbent structure also comprise one or more support or wrapping materials, such as foams, films, woven webs and/or nonwoven webs, as known in the art, such as spunbond, meltblown and/or carded nonwovens. One preferred material is a so-called SMS material, comprising a spunbonded, a melt-blown and a further spunbonded layer. Highly preferred are permanently hydrophilic nonwovens, and in particular nonwovens with durably hydrophilic coatings. An alternative preferred material comprises a SMMS-structure. The top layer and the bottom layer may be provided from two or more separate sheets of materials or they may be alternatively provided from a unitary sheet of material.

Preferred non-woven materials are provided from synthetic fibers, such as PE, PET and most preferably PP. As the polymers used for nonwoven production are inherently hydrophobic, they are preferably coated with hydrophilic coatings, e.g., coated with nanoparticles, as known in the art.

Preferred nonwoven materials and absorbent structures using such materials are described in, for example, co-pending applications US2004/03625, US2004/03624, and US2004/03623 and in US 2004/0162536, EP1403419-A, WO2002/0192366, EP1470281-A and EP1470282-A.

If the absorbent structure herein is an absorbent component (core) for an absorbent article, then the absorbent structure may also comprise a structuring agent or matrix agent, such as absorbent fibrous material, such as airfelt fibers, and/or adhesive, which each may serve to immobilize the water-absorbing material.

Because the water-absorbing material herein has an excellent permeability, even when swollen, there is no need for large amounts of structuring agents, such as absorbent fibrous material (airfelt), as normally used in the art. Thus, when the absorbent structure herein is an absorbent component (core) for an absorbent article, then a relatively low amount or no absorbent fibrous (cellulose) material is used in the absorbent structure of the invention. Thus, it may be preferred that said absorbent structure herein comprises large amounts of the water-absorbing material herein and only very little or no absorbent (cellulose) fibers, preferably less than 20% by weight of the water-absorbing material, or even less than 10% by weight of the water-absorbing material, or even less than 5% by weight. Preferred may even be that the absorbent core (structure) is substantially free of absorbent (cellulose) fibers.

Preferred absorbent structures for use in absorbent articles herein comprise a layer of a substrate material such as the core-wrap materials described herein, and thereon a water-absorbing material layer, optionally as a discontinuous layer, and thereon a layer of an adhesive and/or thermoplastic material or preferably a (fibrous) thermoplastic adhesive material, which is laid down onto the layer of water-absorbing material. Preferred may be that the thermoplastic or adhesive layer is then in direct contact with the water-absorbing material, but also partially in direct contact with the substrate layer, where the substrate layer is not covered by the absorbent polymeric material. This imparts an essentially three-dimensional structure to the (fibrous) layer of thermoplastic or adhesive material, which in itself is essentially a two-dimensional structure of relatively small thickness (in z-direction), as compared to the extension in x- and y-direction. Thereby, the thermoplastic or adhesive material provides cavities to hold the water-absorbing material and thereby immobilizes this material. In a further aspect, the thermoplastic or adhesive material bonds to the substrate and thus affixes the water-absorbing material to the substrate. In this embodiment, it may be preferred that no absorbent fibrous material is present in the absorbent structure.

The thermoplastic composition may comprise, in its entirety, a single thermoplastic polymer or a blend of thermoplastic polymers, having a softening point, as determined by the ASTM Method D-36-95 "Ring and Ball", in the range between 50° C. and 300° C., or alternatively the thermoplastic composition may be a hot melt adhesive comprising at least one thermoplastic polymer in combination with other thermoplastic diluents such as tackifying resins, plasticizers and additives such as antioxidants.

The thermoplastic polymer has typically a molecular weight (Mw) of more than 10,000 and a glass transition temperature (Tg) usually below room temperature. A wide variety of thermoplastic polymers are suitable for use in the present invention. Such thermoplastic polymers are preferably water insensitive. Exemplary polymers are (styrenic) block copolymers including AB-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof.

Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alphaolefins.

The resin has typically a Mw below 5,000 and a Tg usually above room temperature, typical concentrations of the resin in a hot melt are in the range of 30-60%. The plasticizer has a low Mw of typically less than 1,000 and a Tg below room temperature, a typical concentration is 0-15%.

Preferably the adhesive is present in the forms of fibres throughout the core, i.e., the adhesive is fiberized or fibrous. Preferably, the fibres will preferably have an average thickness of 1-50 micrometer and an average length of 5 mm to 50 cm.

Preferably, the absorbent structure or absorbent core, in particular when no or little absorbent fibres are present, as described above, has a density greater than about 0.4 g/cm$^3$. Preferably, the density is greater than about 0.5 g/cm$^3$, more preferably greater than about 0.6 g/cm³. Preferred absorbent structures or components, as defined above, can for example be made as follows:

a) providing a substrate material that can serve as a wrapping material;
b) depositing the water-absorbing material herein onto a first surface of the substrate material, preferably in a pattern comprising at least one zone which is substantially free of water-absorbing material, and the pattern comprising at least one zone comprising water-absorbing material, preferably such that openings are formed between the separate zones with water-absorbing material;
c) depositing a thermoplastic material onto the first surface of the substrate material and the water-absorbing material, such that portions of the thermoplastic material are in direct contact with the first surface of the substrate and portions of the thermoplastic material are in direct contact with the water-absorbing material; and
d) then typically closing the above by folding the substrate material over, or by placing another substrate matter over the above.

The absorbent structure or component as defined above, may comprise an acquisition layer and a storage layer, which may have the same dimensions, however it may be preferred that the acquisition layer is laterally centered on the storage layer with the same lateral width but a shorter longitudinal length than storage layer. The acquisition layer may also be narrower than the storage layer while remaining centered thereon. Said another way, the acquisition layer suitably has an area ratio with respect to storage layer of 1.0, but the area ratio may preferably be less than 1.0, e.g., less than about 0.75, or more preferably less than about 0.50.

For absorbent structures and absorbent articles designed for absorption of urine, it may be preferred that the acquisition layer is longitudinally shorter than the storage layer and positioned such that more than 50% of its longitudinal length is forward of transverse axis of the absorbent structure or of the absorbent article herein. This positioning is desirable so as to place acquisition layer under the point where urine is most likely to first contact absorbent structure or absorbent article.

Also, the absorbent core, or the acquisition layer and/or storage layer thereof, may comprise an uneven distribution of water-absorbing material basis weight in one or both of the machine and cross directions. Such uneven basis weight distribution may be advantageously applied in order to provide extra, predetermined, localized absorbent capacity to the absorbent structure or absorbent article.

As defined above, the absorbent structure of the invention may be, or may be part of an absorbent article, and in the latter case, it may be the absorbent core of an absorbent article, or the storage layer and/or acquisition layer of such an article.

Preferred (disposable) absorbent article comprising the absorbent structure of the invention are sanitary napkins, panty liners, adult incontinence products (diapers, briefs) and infant diapers or training or pull-on pants, whereby articles which serve to absorb urine, e.g., adult incontinence products, diapers and training or pull-on pants are the most preferred articles herein. Preferred articles herein have a topsheet and a backsheet, which each have a front region, back region and crotch region, positioned therein between. The absorbent component or core, or structure, as described herein is typically positioned in between the topsheet and backsheet. Preferred backsheets are vapor pervious but liquid impervious. Preferred topsheet materials are at least partially hydrophilic; preferred are also so-called apertured topsheets. Preferred may be that the topsheet comprises a skin care composition, e.g., a lotion.

Because the water-absorbing material herein has a very high absorbency capacity, it is possible to use only low levels of this material in the absorbent articles herein. Preferred are thus thin absorbent articles, such as adult and infant diapers, training pants, sanitary napkins comprising an absorbent structure of the invention, the articles having an average caliper (thickness) in the crotch region of less than 1.0 cm, preferably less than 0.7 cm, more preferably less than 0.5 cm, or even less than 0.3 cm (for this purpose alone, the crotch region being defined as the central zone of the product, when laid out flat and stretched, having a dimension of 20% of the length of the article and 50% of the width of the article).

Because the water-absorbing material herein have a very good permeability, there is no need to have large amounts of traditional structuring agents presents, such as absorbent fibres, such as airfelt, and the may thus be omitted or only used in very small quantities, as described above. This further helps to reduce the thickness of the absorbent structure, or absorbent articles herein.

Preferred articles according to the present invention achieve a relatively narrow crotch width, which increases the wearing comfort. A preferred article according to the present invention achieves a crotch width of less than 100 mm, 90 mm, 80 mm, 70 mm, 60 mm or even less than 50 mm, as measured along a transversal line with is positioned at equal distance to the front edge and the rear edge of the article, or at the point with the narrowest width. Hence, preferably an absorbent structure according to the present invention has a crotch width as measured along a transversal line with is positioned at equal distance to the front edge and the rear edge of the core which is of less than 100 mm, 90 mm, 80 mm, 70 mm, 60 mm or even less than 50 mm. It has been found that for most absorbent articles the liquid discharge occurs predominately in the front half.

A preferred diaper herein has a front waist band and a back waist band, whereby the front waist band and back waist band each have a first end portion and a second end portion and a middle portion located between the end portions, and whereby preferably the end portions comprise each a fastening system, to fasten the front waist band to the rear waist band or whereby preferably the end portions are connected to one another, and whereby the middle portion of the back waist band and/or the back region of the backsheet and/or the crotch region of the backsheet comprises a landing member, preferably the landing member comprising second engaging elements selected from loops, hooks, slots, slits, buttons, magnets. Most preferred are hooks, adhesive or cohesive second engaging elements. Preferred may be that the engaging elements on the article, or preferably diaper are provided with a means to ensure they are only engage able at certain moments, for example, they may be covered by a removable tab, which is removed when the engaging elements are to be engaged and may be re-closed when engagement is no longer needed, as described above.

Preferred diapers and training pants herein have one or more sets of leg elastics and/or barrier leg cuffs, as known in the art. Preferred may also be that diaper has a secondary topsheet, in contact with the skin and preferably overlaying a primary topsheet, as for example described above), said secondary topsheet having an elongated slit opening, preferably with elastication means along the length thereof, where through waste material can pass into a void space above the absorbent structure, and which ensures said waste material is isolated in this void space, away from the wearer's skin.

Water-Absorbing Polymers and Materials

Useful for the purposes of the present invention are in principle all particulate water-absorbing polymers known to one skilled in the art from superabsorbent literature for example as described in Modern Superabsorbent Polymer Technology, F. L. Buchholz, A. T. Graham, Wiley 1998. The superabsorbent particles are preferably spherical superabsorbent particles, or vienna-sausage shaped superabsorbent particles, or ellipsoid shaped superabsorbent particles of the kind typically obtained from inverse phase suspension polymerizations; they can also be optionally agglomerated at least to some extent to form larger irregular particles. Useful for the purposes of the present invention are also round-shaped particles from spray- or other gas-phase dispersion polymerisations. But most particular preference is given to commercially available irregularly shaped particles of the kind obtainable by current state of the art production processes as is more particularly described herein below by way of example. The porosity of the water-absorbing particles useful in the present invention is not critical.

The polymeric particles that are coated according to the process of the present invention are preferably polymeric particles obtainable by polymerization of a monomer solution comprising
i) at least one ethylenically unsaturated acid-functional monomer,
ii) at least one crosslinker,
iii) if appropriate one or more ethylenically and/or allylically unsaturated monomers copolymerizable with i) and
iv) if appropriate one or more water-soluble polymers onto which the monomers i), ii) and if appropriate iii) can be at least partially grafted,
wherein the base polymer obtained thereby is dried, classified and—if appropriate—is subsequently treated with
v) at least one post-crosslinker
before being dried and thermally post-crosslinked (i.e. Surface crosslinked).

Useful monomers i) include for example ethylenically unsaturated carboxylic acids, such as acrylic acid, methacrylic acid, maleic acid, fumaric acid, tricarboxy ethylene and itaconic acid, or derivatives thereof, such as acrylamide, methacrylamide, acrylic esters and methacrylic esters. Acrylic acid and methacrylic acid are particularly preferred monomers. Acrylic acid is most preferable.

The water-absorbing polymers to be used according to the present invention are typically crosslinked, i.e., the polymerization is carried out in the presence of compounds having two or more polymerizable groups which can be free-radically copolymerized into the polymer network. Useful crosslinkers ii) include for example ethylene glycol dimethacrylate, diethylene glycol diacrylate, allyl methacrylate, trimethylolpropane triacrylate, triallylamine, tetraallyloxyethane as described in EP-A 530 438, di- and triacrylates as described in EP-A 547 847, EP-A 559 476, EP-A 632 068, WO 93/21237, WO 03/104299, WO 03/104300, WO 03/104301 and in the DE-A 103 31 450, mixed acrylates which, as well as acrylate groups, comprise further ethylenically unsaturated groups, as described in DE-A 103 31 456 and DE-A 103 55 401, or crosslinker mixtures as described for example in DE-A 195 43 368, DE-A 196 46 484, WO 90/15830 and WO 02/32962.

Useful crosslinkers ii) include in particular N,N'-methylenebisacrylamide and N,N'-methylenebismethacrylamide, esters of unsaturated mono- or polycarboxylic acids of polyols, such as diacrylate or triacrylate, for example butanediol diacrylate, butanediol dimethacrylate, ethylene glycol diacrylate, ethylene glycol dimethacrylate and also trimethylolpropane triacrylate and allyl compounds, such as allyl(meth)acrylate, triallyl cyanurate, diallyl maleate, polyallyl esters, tetraallyloxyethane, triallylamine, tetraallylethylenediamine, allyl esters of phosphoric acid and also vinylphosphonic acid derivatives as described for example in EP-A 343 427. Useful crosslinkers ii) further include pentaerythritol diallyl ether, pentaerythritol triallyl ether, pentaerythritol tetraallyl ether, polyethylene glycol diallyl ether, ethylene glycol diallyl ether, glycerol diallyl ether, glycerol triallyl ether, polyallyl ethers based on sorbitol, and also ethoxylated variants thereof. The process of the present invention preferably utilizes di(meth)acrylates of polyethylene glycols, the polyethylene glycol used having a molecular weight in the range from 300 g/mole to 1000 g/mole.

However, particularly advantageous crosslinkers ii) are di- and triacrylates of altogether 3- to 15-tuply ethoxylated glycerol, of altogether 3- to 15-tuply ethoxylated trimethylolpropane, especially di- and triacrylates of altogether 3-tuply ethoxylated glycerol or of altogether 3-tuply ethoxylated trimethylolpropane, of 3-tuply propoxylated glycerol, of 3-tuply propoxylated trimethylolpropane, and also of altogether 3-tuply mixedly ethoxylated or propoxylated glycerol, of altogether 3-tuply mixedly ethoxylated or propoxylated trimethylolpropane, of altogether 15-tuply ethoxylated glycerol, of altogether 15-tuply ethoxylated trimethylolpropane, of altogether at least 40-tuply ethoxylated glycerol and also of altogether at least 40-tuply ethoxylated trimethylolpropane. Where n-tuply ethoxylated means that n mols of ethylene oxide are reacted to one mole of the respective polyol with n being an integer number larger than 0.

Very particularly preferred for use as crosslinkers ii) are diacrylated, dimethacrylated, triacrylated or trimethacrylated multiply ethoxylated and/or propoxylated glycerols as described for example in WO 03/104301. Di- and/or triacrylates of 3- to 10-tuply ethoxylated glycerol are particularly advantageous. Very particular preference is given to di- or triacrylates of 1- to 5-tuply ethoxylated and/or propoxylated glycerol. The triacrylates of 3- to 5-tuply ethoxylated and/or propoxylated glycerol are most preferred. These are notable for particularly low residual levels in the water-absorbing polymer (typically below 10 ppm) and the aqueous extracts of water-absorbing polymers produced therewith have an almost unchanged surface tension compared with water at the same temperature (typically not less than 0.068 N/m).

Examples of ethylenically unsaturated monomers iii) which are copolymerizable with the monomers i) are acrylamide, methacrylamide, crotonamide, dimethylaminoethyl methacrylate, dimethylaminoethyl acrylate, dimethylaminopropyl acrylate, diethylaminopropyl acrylate, dimethylaminobutyl acrylate, dimethylaminoethyl methacrylate, diethylaminoethyl methacrylate, dimethylaminoneopentyl acrylate and dimethylaminoneopentyl methacrylate.

Useful water-soluble polymers iv) include polyvinyl alcohol, polyvinylpyrrolidone, starch, starch derivatives, polyglycols, polyacrylic acids, polyvinylamine or polyallylamine, partially hydrolysed polyvinylformamide or polyvinylacetamide, preferably polyvinyl alcohol and starch.

Preference is given to water-absorbing polymeric particles whose base polymer is lightly crosslinked. The light degree of crosslinking is reflected in the high CRC value and also in the fraction of extractables.

The crosslinker is preferably used (depending on its molecular weight and its exact composition) in such amounts that the base polymers produced have a CRC between 20 and 60 g/g when their particle size is between 150 and 850 □m and the 16 h extractables fraction is not more than 25% by weight. The CRC is preferably between 30 and 50 g/g, more preferably between 33 and 45 g/g.

Particular preference is given to base polymers having a 16 h extractables fraction of not more than 20% by weight, preferably not more than 15% by weight, even more preferably not more than 10% by weight and most preferably not more than 7% by weight and whose CRC values are within the preferred ranges that are described above.

The preparation of a suitable base polymer and also further useful hydrophilic ethylenically unsaturated monomers i) are described in DE-A 199 41 423, EP-A 686 650, WO 01/45758 and WO 03/14300.

The reaction is preferably carried out in a kneader as described for example in WO 01/38402, or on a belt reactor as described for example in EP-A-955 086.

It is further possible to use any conventional inverse suspension polymerization process using any known suitable solvent. If appropriate, the fraction of crosslinker can be greatly reduced or completely omitted in such an inverse suspension polymerization process, since self-crosslinking occurs in such processes under certain conditions known to one skilled in the art.

It is further possible to make base polymers using any desired spray- or other gas-phase polymerization process capable of producing spherical or irregular shaped particles in a gas phase suspension of fine droplets, preferably in an inert gas phase. Inert gases are the ones described herein, organic solvent vapor and water-vapor.

The acid groups of the base polymers obtained are typically 0-100 mol %, preferably 25-100 mol %, more preferably 65-90 mol % and most preferably 68-80 mol % neutralized, for which the customary neutralizing agents can be used, for example ammonia, or amines, such as ethanolamine, diethanolamine, triethanolamine or dimethylaminoethanolamine, preferably alkali metal hydroxides, alkali metal oxides, alkali metal carbonates or alkali metal bicarbonates and also mixtures thereof, in which case sodium and potassium are particularly preferred as alkali metal salts, but most preferred is sodium hydroxide, sodium carbonate or sodium bicarbonate and also mixtures thereof. Typically, neutralization is achieved by admixing the neutralizing agent as an aqueous solution or as an aqueous dispersion or else preferably as a molten or as a solid material.

Neutralization can be carried out after polymerization, at the base polymer stage. But it is also possible to neutralize up to 40 mol %, preferably from 10 to 30 mol % and more preferably from 15 to 25 mol % of the acid groups before polymerization by adding a portion of the neutralizing agent to the monomer solution and to set the desired final degree of neutralization only after polymerization, at the base polymer stage. The monomer solution may be neutralized by admixing the neutralizing agent, either to a predetermined degree of preneutralization with subsequent post-neutralization to the final value after or during the polymerization reaction, or the monomer solution is directly adjusted to the final value by admixing the neutralizing agent before polymerization. The base polymer can be mechanically comminuted, for example by means of a meat grinder, in which case the neutralizing agent can be sprayed, sprinkled or poured on and then carefully mixed in. To this end, the gel mass obtained can be repeatedly minced for homogenization.

The neutralized base polymer is then dried with a belt, fluidized bed, tower dryer or drum dryer until the residual moisture content is preferably below 13% by weight, especially below 8% by weight and most preferably below 4% by weight, the water content being determined according to EDANA's recommended test method No. 430.2-02 "Moisture content" (EDANA=European Disposables and Nonwovens Association). The dried base polymer is thereafter ground and sieved, useful grinding apparatus typically include roll mills, pin mills, hammer mills, jet mills or swing mills.

The water-absorbing polymers to be used can be post-crosslinked in one version of the present invention. Useful post-crosslinkers v) include compounds comprising two or more groups capable of forming covalent bonds with the carboxylate groups of the polymers. Useful compounds include for example alkoxysilyl compounds, polyaziridines, polyamines, polyamidoamines, di- or polyglycidyl compounds as described in EP-A 083 022, EP-A 543 303 and EP-A 937 736, polyhydric alcohols as described in DE-C 33 14 019. Useful post-crosslinkers v) are further said to include by DE-A 40 20 780 cyclic carbonates, by DE-A 198 07 502 2-oxazolidone and its derivatives, such as N-(2-hydroxyethyl)-2-oxazolidone, by DE-A 198 07 992 bis- and poly-2-oxazolidones, by DE-A 198 54 573 2-oxotetrahydro-1,3-oxazine and its derivatives, by DE-A 198 54 574 N-acyl-2-oxazolidones, by DE-A 102 04 937 cyclic ureas, by DE-A 103 34 584 bicyclic amide acetals, by EP-A 1 199 327 oxetanes and cyclic ureas and by WO 03/031482 morpholine-2,3-dione and its derivatives.

Post-crosslinking is typically carried out by spraying a solution of the post-crosslinker onto the base polymer or the dry base-polymeric particles. Spraying is followed by thermal drying, and the post-crosslinking reaction can take place not only before but also during or after drying.

Preferred post-crosslinkers v) are amide acetals, carbamic esters, polyhydric alcohols like diols or polyols, cyclic carbonates or bisoxazolines described for example in prior PCT application PCT/EP/05011073, which is hereby expressly incorporated herein by reference.

The at least one post-crosslinker v) is typically used in an amount of about 1.50 wt. % or less, preferably not more than 0.50% by weight, more preferably not more than 0.30% by weight and most preferably in the range from 0.001% and 0.15% by weight, all percentages being based on the base polymer, as an aqueous solution. It is possible to use a single post-crosslinker v) from the above selection or any desired mixtures of various post-crosslinkers.

The aqueous post-crosslinking solution, as well as the at least one post-crosslinker v), can typically further comprise a cosolvent. Cosolvents which are technically highly useful are $C_1$-$C_6$-alcohols, such as methanol, ethanol, n-propanol, iso-propanol, n-butanol, sec-butanol, tert-butanol or 2-methyl-1-propanol, $C_2$-$C_5$-diols, such as ethylene glycol, 1,2-propylene glycol, 1,3-propanediol or 1,4-butanediol, ketones, such as acetone, or carboxylic esters, such as ethyl acetate.

One particular embodiment does not utilize any cosolvent. The at least one post-crosslinker v) is then only employed as a solution in water, with or without an added deagglomerating aid. Deagglomerating aids are known to one skilled in the art and are described for example in DE-A-10 239 074 and also prior PCT application PCT/EP/05011073, which are each hereby expressly incorporated herein by reference. Preferred deagglomerating aids are surfactants such as ethoxylated and alkoxylated derivatives of 2-propylheptanol and also sorbitan monoesters. Particularly preferred deagglomerating aids are Plantaren® (Cognis), Span® 20, Polysorbate® 20—also referred to as Tween® 20 or polyoxyethylene 20 sorbitan monolaurate, and polyethylene glycol 400 monostearate.

The concentration of the at least one post-crosslinker v) in the aqueous post-crosslinking solution is for example in the range from 1% to 50% by weight, preferably in the range from 1.5% to 20% by weight and more preferably in the range from 2% to 5% by weight, based on the post-crosslinking solution.

In a further embodiment, the post-crosslinker is dissolved in at least one organic solvent and spray dispensed; in this case, the water content of the solution is less than 10 wt. %, preferably no water at all is utilized in the post-crosslinking solution.

It is however understood that post-crosslinkers which effect comparable surface-crosslinking results with respect to the final polymer performance may of course be used in this invention even when the water content of the solution containing such post-crosslinker and optionally a cosolvent is anywhere in the range of >0 to <100% by weight.

The total amount of post-crosslinking solution based on the base polymer is typically in the range from 0.3% to 15% by weight and preferably in the range from 2% to 6% by weight. The practice of post-crosslinking is common knowledge to those skilled in the art and described for example in DE-A-12 239 074 and also prior PCT application PCT/EP/05011073.

Spray nozzles useful for post-crosslinking are not subject to any restriction. Suitable nozzles and atomizing systems are described for example in the following literature references: Zerstäuben von Flüssigkeiten, Expert-Verlag, volume 660, Reihe Kontakt & Studium, Thomas Richter (2004) and also in Zerstäubungstechnik, Springer-Verlag, VDI-Reihe, Günter Wozniak (2002). Mono- and polydisperse spraying systems can be used. Suitable polydisperse systems include one-material pressure nozzles (forming a jet or lamellae), rotary atomizers, two-material atomizers, ultrasonic atomizers and impact nozzles. With regard to two-material atomizers, the mixing of the liquid phase with the gas phase can take place not only internally but also externally. The spray pattern produced by the nozzles is not critical and can assume any desired shape, for example a round jet, flat jet, wide angle round jet or circular ring. When two-material atomizers are used, the use of an inert gas stream will be advantageous. Such nozzles can be pressure fed with the liquid to be spray dispensed. The atomization of the liquid to be spray dispensed can in this case be effected by decompressing the liquid in the nozzle bore after the liquid has reached a certain minimum velocity. Also useful are one-material nozzles, for example slot nozzles or swirl or whirl chambers (full cone) nozzles (available for example from Düsen-Schlick GmbH, Germany or from Spraying Systems Deutschland GmbH, Germany). Such nozzles are also described in EP-A-0 534 228 and EP-A-1 191 051. One-material nozzles and two-material nozzles are sometimes also referred to as single-fluid or two-fluid nozzles, respectively.

After spraying, the water-absorbing polymeric particles are thermally dried, and the post-crosslinking reaction can take place before, during or after drying.

The spraying with the solution of post-crosslinker is preferably carried out in mixers having moving mixing implements, such as screw mixers, paddle mixers, disk mixers, plowshare mixers and shovel mixers. Particular preference is given to vertical mixers and very particular preference to plowshare mixers and shovel mixers. Useful mixers include for example Lödige® mixers, Bepex® mixers, Nauta® mixers, Processall® mixers and Schugi® mixers.

Contact dryers are preferable, shovel dryers are more preferable and disk dryers are most preferable as the apparatus in which thermal drying is carried out. Suitable dryers include for example Bepex dryers and Nara® dryers. Fluidized bed dryers can be used as well, an example being Carman® dryers.

Drying can take place in the mixer itself, for example by heating the jacket or introducing a stream of hot inert gases. It is similarly possible to use a downstream dryer, for example a tray dryer, a rotary tube oven, a continuous fluidized bed dryer, or a continuous spouted bed dryer, or a heatable screw. But it is also possible for example to utilize an azeotropic distillation as a drying process.

It is particularly preferable to apply the solution of post-crosslinker in a high speed mixer, for example of the Schugi-Flexomix® or Turbolizer® type, to the base polymer and the latter can then be thermally post-crosslinked in a reaction dryer, for example of the Nara-Paddle-Dryer type or a disk dryer (i.e. Torus-Disc Dryer®, Hosokawa). The temperature of the base polymer can be in the range from 10 to 120° C. from preceding operations, and the post-crosslinking solution can have a temperature in the range from 0 to 150° C. More particularly, the post-crosslinking solution can be heated to lower the viscosity. The preferred post-crosslinking and drying temperature range is from 30 to 220° C., especially from 120 to 210° C. and most preferably from 145 to 190° C. The preferred residence time at this temperature in the reaction mixer or dryer is preferably less than 100 minutes, more preferably less than 70 minutes and most preferably less than 40 minutes.

It is particularly preferable to utilize a continuous fluidized bed dryer or continuous spouted bed dryer for the crosslinking reaction, and the residence time is then preferably below 30 minutes, more preferably below 20 minutes and most preferably below 10 minutes.

The post-crosslinking dryer or fluidized bed dryer may be operated with air, or dehumidified air, or dried air to remove vapors efficiently from the polymer.

The post-crosslinking dryer is preferably purged with an inert gas during the drying and post-crosslinking reaction in order that vapors may be removed and oxidizing gases, such as atmospheric oxygen, may be displaced. The inert gas typically has the same limitations for relative humidity as described above for air. Mixtures of air and inert gases may also be used. To augment the drying process, the dryer and the attached assemblies are thermally well-insulated and ideally fully heated. The inside of the post-crosslinking dryer is preferably at atmospheric pressure, or else at a slight under- or overpressure.

To produce a very white polymer, the gas space in the dryer is kept as free as possible of oxidizing gases; at any rate, the volume fraction of oxygen in the gas space is not more than 14% by volume.

The water-absorbing polymeric particles can have a particle size distribution in the range from 45 µm to 4000 µm. Particle sizes used in the hygiene sector preferably range from 45 µm to 1000 µm, preferably from 45-850 µm, and especially from 100 µm to 850 µm. It is preferable to coat water-absorbing polymeric particles having a narrow particle size distribution, especially 100-850 µm, or even 100-600 µm.

Narrow particle size distributions are those in which not less than 80% by weight of the particles, preferably not less than 90% by weight of the particles and most preferably not less than 95% by weight of the particles are within the selected range; this fraction can be determined using the familiar sieve method of EDANA 420.2-02 "Particle Size Distribution". Selectively, optical methods can be used as well, provided these are calibrated against the accepted sieve method of EDANA.

Preferred narrow particle size distributions have a span of not more than 700 µm, more preferably of not more than 600 µm, and most preferably of less than 400 µm. Span here refers to the difference between the coarse sieve and the fine sieve which bound the distribution. The coarse sieve is not coarser than 850 µm and the fine sieve is not finer than 45 µm. Particle size ranges which are preferred for the purposes of the present invention are for example fractions of 150-600 µm (span: 450

μm), of 200-600 μm (span: 400 μm), of 300-600 μm (span: 300 μm), of 200-700 μm (span: 500 μm), of 150-500 μm (span: 350 μm), of 150-300 μm (span: 150 μm), of 300-700 μm (span: 400 μm), of 400-800 μm (span: 400 μm), of 100-800 μm (span: 700 μm).

Particularly preferred water-absorbing particles contain less than 3 wt. %, more preferably less than 1 wt. %, most preferably less than 0.5 wt. % particles with a particle size less than 150 μm.

Between the coarse sieve and the fines sieve, there can be additional sieves placed in the machine to increase the efficiency of screening. The water-absorbing polymeric particles may be sifted at elevated temperature by heating the screening apparatus and/or the water-absorbing particles. Preferably screening takes place under negative pressure vs. outside atmosphere to ensure fine dust containment at all times. Preferably screening takes place under dehumidified or dried air atmosphere. In another preferred embodiment screening takes place under inert gas, optionally dehumidified or dried inert gas. Screening typically takes place after grinding of the base polymer and optionally after surface-cross-linking. Screening preferably takes place before coating the water-absorbing polymeric particles with a film-forming polymer and optionally a second time after heat-treatment of the coated particles. Fine particles generated during any of the foregoing screening processes may be disposed or optionally recycled in the production process. Coarse particles may be disposed or preferably recycled in the production process. Coarse particle may be recycled by passing them through the grinding step at least one more time.

Preference is likewise given to monodisperse water-absorbing polymeric particles as obtained from the inverse suspension polymerization process. It is similarly possible to select mixtures of monodisperse particles of different diameter as water-absorbing polymeric particles, for example mixtures of monodisperse particles having a small diameter and monodisperse particles having a large diameter. It is similarly possible to use mixtures of monodisperse with polydisperse water-absorbing polymeric particles.

Coating these water-absorbing polymeric particles having narrow particle size distributions and preferably having a maximum particle size of ≦600 μm according to the present invention provides a water-absorbing material, which swells rapidly and therefore is particularly preferred.

The water-absorbing particles can be spherical in shape as well as irregularly shaped particles.

Film-Forming Elastic Polymers

The water-absorbing material herein comprises water-absorbing polymer particles that are coated with a film coating formed from one or more coating agents, which include at least an elastic film-forming polymer and a coalescing agent. Typically, the film coating is formed by spray-coating the water-absorbing polymer particles with said elastic film forming polymer and heat treating or annealing the thus obtained coating to form a film coating, as described herein below in detail.

The term polymer as used herein refers to single polymers and blends of polymers. The polymers to be preferably used according to the present invention for coating are film forming and have elastomeric properties. Polymers having film-forming and also elastic properties are generally suitable, such as copolyesters, copolyamides, silicones, styrene-isoprene block copolymers, styrene-butadiene block copolymers, polyurethanes and blends with these polymers. Preferred are polyurethanes and polyurethane blends.

Film-forming means that the respective polymer can readily be made into a layer or coating upon evaporation of the solvent in which it is dissolved or dispersed. The polymer may for example be thermoplastic and/or crosslinked. Elastomeric means the material will exhibit stress-induced deformation that is partially or completely reversed upon removal of the stress.

In one embodiment, the polymer has a tensile stress at break in the wet state of at least 1 MPa, or even at least 3 MPa and more preferably at least 5 MPa, or even at least 8 MPa. Most preferred materials have tensile stress at break of at least 10 MPa, preferably at least 40 MPa. This can be determined by the test method, described below.

In one embodiment, particularly preferred polymers herein are materials that have a wet secant elastic modulus at 400% elongation ($SM_{wet\ 400\%}$) of at least 0.25 MPa, preferably at least about 0.50 MPa, more preferably at least about 0.75 or even at least 2.0 MPa, and most preferably of at least about 3.0 MPa as determined by the test method below.

In one embodiment, preferred polymers herein have a ratio of [wet secant elastic modulus at 400% elongation ($SM_{wet\ 400\%}$)] to [dry secant elastic modulus at 400% elongation ($SM_{dry\ 400\%}$)] of 10 or less, preferably of 1.4 or less, more preferably 1.2 or less or even more preferably 1.0 or less, and it may be preferred that this ratio is at least 0.1, preferably at least 0.6, or even at least 0.7.

In one embodiment, the film-forming polymer is present in the form of a coating that has a shell tension, which is defined as the (Theoretical equivalent shell caliper)×(Average wet secant elastic modulus at 400% elongation) of about 5 to 200 N/m, or preferably of 10 to 170 N/m, or more preferably 20 to 130 N/m, and even more preferably 40 to 110 N/m.

In one embodiment of the invention where the water-absorbing polymer particles herein have been post-crosslinked (either prior to application of the shell described herein, or at the same time as applying said shell), it may even be more preferred that the shell tension of the water-absorbing material is in the range from 15 N/m to 60N/m, or even more preferably from 20 N/m to 60N/m, or preferably from 40 to 60 N/m.

In yet another embodiment wherein the water absorbing polymeric particles are not post-crosslinked, it is even more preferred that the shell tension of the water-absorbing material is in the range from about 60 to 110 N/m.

In one embodiment, the film-forming polymer is present in the form of a coating on the surface of the water absorbing material, that has a shell impact parameter, which is defined as the (Average wet secant elastic modulus at 400% elongation)*(Relative Weight of the shell polymer compared to the total weight of the coated polymer) of about 0.03 MPa to 0.6 MPa, preferably 0.07 MPa to 0.45 MPa, more preferably about 0.1 to 0.35 MPa. The "Relative Weight of the shell polymer compared to the total weight of the coated polymer" is a fraction typically from 0.0 to 1.0.

The resulting water absorbing materials show an unusual beneficial combination of absorbent capacity as measured in the CS-CRC test and permeability as measured in the CS-SFC test described herein.

In one embodiment, preference is given to film-forming polymers especially polyurethanes, which, in contrast to the water-absorbing polymeric particles, swell only little if at all in contact with aqueous fluids. This means in practice that the film-forming polymers have preferably a water-swelling capacity of less than 1 g/g, or even less than 0.5 g/g, or even less than 0.2 g/g or even less than 0.1 g/g, as may be determined by the method, as set out below.

In another embodiment preference is given to film-forming polymers, especially polyurethanes, which, in contrast to the water-absorbing polymeric particles, swell only moderately on contact with aqueous fluids. This means in practice that the film-forming polymers have preferably a water-swelling capacity of at least 1 g/g, or more than 2 g/g, or even more than 3 g/g, or preferably 4 to 10 g/g, but less than 30 g/g, preferably less than 20 g/g, most preferably less than 12 g/g, as may be determined by the method, as set out below.

The film-forming polymer is typically such that the resulting coating on the water-swellable polymers herein is not water-soluble and, preferably not water-dispersible once a film has been formed.

In one embodiment, the polymer is preferably such that the resulting coating on the water-swellable polymers herein is water-permeable, but not water-soluble and, preferably not water-dispersible. Preferably, the polymer especially the polyurethane (tested in the form of a film of a specific caliper, as described herein) is at least moderately water-permeable (breathable) with a moisture vapor transmission rate (MVTR) of more than 200 g/m$^2$/day, preferably breathable with a MVTR of 800 g/m$^2$/day or more preferably 1200 to 1500 g/m$^2$$^1$ day, even more preferably breathable with a MVTR of at least 1500 g/m$^2$ day, up to 2100 g/m$^2$/day (inclusive), and most preferably the coating agent or material is highly breathable with a MVTR of 2100 g/m$^2$ day or more.

In order to impart desirable properties to the elastic polymer, additionally fillers such as particulates, oils, solvents, plasticizers, surfactants, dispersants, or blowing aids may be optionally incorporated into the polymer, polymer solution, or polymer dispersion.

Blowing aids are for example—but not limited to—chemical additives like urea, components of baking powder, sodium hydrogen carbonate, azodicarbonamide, azo-compounds, carbon dioxide, nitrogen which by a chemical reaction or a physical effect—for example at elevated temperature—form gas bubbles inside the coating layer which perforate the films in a controlled manner.

In one embodiment of the invention the resulting coating with the film-forming polymer shows in addition a low permeability to water. In these cases the use of blowing aids or fillers is preferred to create defects in the shell in order to enable swelling of the water-swellable polymers.

The mechanical properties as described above are believed to be characteristic in certain embodiments for a suitable film-forming polymer for coating. The polymer may be hydrophobic or hydrophilic. For fast wetting it is however preferable that the polymer is hydrophilic.

The film-forming polymer can for example be applied from a solution or an aqueous solution or in another embodiment can be applied from a dispersion or in a preferred embodiment from an aqueous dispersion. The solution can be prepared using any suitable organic solvent for example acetone, isopropanol, tetrahydrofuran, methyl ethyl ketone, dimethyl sulfoxide, dimethylformamide, N-methylpyrrolidone, chloroform, ethanol, methanol or mixtures thereof.

Polymers can also be blended prior to coating by blending their respective solutions or their respective dispersions. Alternatively polymers can be blended by simultaneous spraying or subsequent spraying. In particular, polymers that do not fulfill the elastic criteria or permeability criteria by themselves can be blended with polymers that do fulfill these criteria and yield a blend that is suitable for coating in the present invention.

Suitable elastomeric polymers which are applicable from solution are for example Vector® 4211 (Dexco Polymers, Texas, USA), Vector 4111, Septon 2063 (Septon Company of America, A Kuraray Group Company), Septon 2007, Estane® 58245 (Noveon, Cleveland, USA), Estane 4988, Estane 4986, Estane® X-1007, Estane T5410, Irogran PS370-201 (Huntsman Polyurethanes), Irogran VP 654/5, Pellethane 2103-70A (Dow Chemical Company), Elastollan® LP 9109 (Elastogran).

In a preferred embodiment the polymer is in the form of an aqueous dispersion and in a more preferred embodiment the polymer is an aqueous dispersion of a polyurethane.

The synthesis of polyurethanes and the preparation of polyurethane dispersions is well described for example in Ullmann's Encyclopedia of Industrial Chemistry, Sixth Edition, 2000 Electronic Release.

The polyurethane is preferably hydrophilic and in particular surface hydrophilic. This hydrophilicity may also be achieved (enhanced) via addition of fillers, surfactants, deagglomeration and coalescing agents. The surface hydrophilicity may be determined by methods known to those skilled in the art. In a preferred execution, the hydrophilic polyurethanes are materials that are wetted by the liquid that is to be absorbed (0.9% saline; urine). They may be characterized by a contact angle that is less than 90 degrees. Contact angles can for example be measured with the Video-based contact angle measurement device, Krüss G10-G1041, available from Kruess, Germany or by other methods known in the art.

In one preferred embodiment, the hydrophilic properties are achieved as a result of the polyurethane comprising hydrophilic polymer blocks, for example polyether groups having a fraction of groups derived from ethylene glycole ($CH_2CH_2O$) or from 1,4-butanediole ($CH_2CH_2CH_2CH_2O$) or from 1,3-propanediole ($CH_2CH_2CH_2O$) or from 1,2-propanediole (—$CH(CH_3)$—$CH_2O$—), or mixtures thereof. Polyetherpolyurethanes are therefore preferred film-forming polymers. The hydrophilic blocks can be constructed in the manner of comb polymers where parts of the side chains or all side chains are hydrophilic polymeric blocks. But the hydrophilic blocks can also be constituents of the main chain (i.e., of the polymer's backbone). A preferred embodiment utilizes polyurethanes where at least the predominant fraction of the hydrophilic polymeric blocks is present in the form of side chains. The side chains can in turn be polyethylene glycol or block copolymers such as poly(ethylene glycol)-co-poly (propylene glycol). If poly(ethylene glycol)-co-poly(propylene glycol) copolymers are used, then the content of ethylene oxide units should be at least 50 mole %, preferably at least 65 mole %.

It is further possible to obtain hydrophilic properties for the polyurethanes through an elevated fraction of ionic groups, preferably carboxylate, sulfonate, phosphonate or ammonium groups. The ammonium groups may be protonated or alkylated tertiary or quarternary groups. Carboxylates, sulfonates, and phosphates may be present as alkali-metal or ammonium salts. Suitable ionic groups and their respective precursors are for example described in "Ullmanns Encyclopädie der technischen Chemie", 4$^{th}$ Edition, Volume 19, p. 311-313 and are furthermore described in DE-A 1 495 745 and WO 03/050156.

The hydrophilicity of the preferred polyurethanes facilitates the penetration and dissolution of water into the water-absorbing polymeric particles, which are enveloped by the film-forming polymer. The present invention's coatings with these preferred polyurethanes are notable for the fact that the mechanical properties are not excessively impaired even in the moist state, despite the hydrophilicity.

Preferred film forming polymers have two or more glass transition temperatures (Tg) (determined by DSC). Ideally, the polymers used exhibit the phenomenon of phase separation, i.e., they contain two or more different blocks of low and high Tg side by side in the polymer (Thermoplastic Elastomers: A Comprehensive Review, eds. Legge, N. R., Holden, G., Schroeder, H. E., 1987, chapter 2). However, the measurement of Tg may in practice be very difficult in cases when several Tg's are close together or for other experimental reasons. Even in cases when the Tg's cannot be determined clearly by experiment the polymer may still be suitable in the scope of the present invention.

Especially preferred phase-separating polymers, and especially polyurethanes, herein comprise one or more phase-separating block copolymers, having a weight average molecular weight Mw of at least 5 kg/mol, preferably at least 10 kg/mol and higher.

In one embodiment such a block copolymer has at least a first polymerized homopolymer segment (block) and a second polymerized homopolymer segment (block), polymerized with one another, whereby preferably the first (soft) segment has a $Tg_1$ of less than 25° C. or even less than 20° C., or even less than 0° C., and the second (hard) segment has a $Tg_2$ of at least 50° C., or of 55° C. or more, preferably 60° C. or more or even 70° C. or more.

In another embodiment, especially with polyurethanes, such a block copolymer has at least a first polymerized polymer segment (block) and a second polymerized polymer segment (block), polymerized with one another, whereby preferably the first (soft) segment has a $Tg_1$ of less than 25° C. or even less than 20° C., or even less than 0° C., and the second (hard) segment has a $Tg_2$ of at least 50° C., or of 55° C. or more, preferably 60° C. or more or even 70° C. or more.

The preferred weight average molecular weight of a first (soft) segment (with a Tg of less than 25° C.) is at least 500 g/mol, preferably at least 1000 g/mol or even at least 2000 g/mol, but preferably less than 8000 g/mol, preferably less than 5000 g/mol.

However, the total of the first (soft) segments is typically 20% to 95% by weight of the total block copolymer, or even from 20% to 85% or more preferably from 30% to 75% or even from 40% to 70% by weight. Furthermore, when the total weight level of soft segments is more than 70%, it is even more preferred that an individual soft segment has a weight average molecular weight of less than 5000 g/mol.

It is well understood by those skilled in the art that "polyurethanes" is a generic term used to describe polymers that are obtained by reacting di- or polyisocyanates with at least one di- or polyfunctional "active hydrogen-containing" compound. "Active hydrogen containing" means that the di- or polyfunctional compound has at least 2 functional groups which are reactive toward isocyanate groups (also referred to as reactive groups), e.g. hydroxyl groups, primary and secondary amino groups and mercapto (SH) groups.

It also is well understood by those skilled in the art that polyurethanes also include allophanate, biuret, carbodiimide, oxazolidinyl, isocyanurate, uretdione, and other linkages in addition to urethane and urea linkages.

In one embodiment the block copolymers useful herein are preferably polyether urethanes and polyester urethanes. Especially preferred are polyether urethanes comprising polyalkylene glycol units, especially polyethylene glycol units or poly(tetramethylene glycol) units.

In one preferred embodiment polyester urethanes are used as they often exhibit better mechanical properties in the wet state when compared to polyether urethanes.

As used herein, the term "alkylene glycol" includes both alkylene glycols and substituted alkylene glycols having 2 to 10 carbon atoms, such as ethylene glycol, 1,3-propylene glycol, 1,2-propylene glycol, 1,2-butylene glycol, 1,3-butylene glycol, 1,4-butylene glycol, styrene glycol and the like.

The polyurethanes used according to the present invention are generally obtained by reaction of polyisocyanates with active hydrogen-containing compounds having two or more reactive groups. These include
a) high molecular weight compounds having a molecular weight in the range of preferably 300 to 100 000 g/mol especially from 500 to 30 000 g/mol
b) low molecular weight compounds and
c) compounds having polyether groups, especially polyethylene oxide groups or polytetrahydrofuran groups and a molecular weight in the range from 200 to 20 000 g/mol, the polyether groups in turn having no reactive groups.

These compounds can also be used as mixtures.

Suitable polyisocyanates have an average of about two or more isocyanate groups, preferably an average of about two to about four isocyanate groups and include aliphatic, cycloaliphatic, araliphatic, and aromatic polyisocyanates, used alone or in mixtures of two or more. Diisocyanates are more preferred. Especially preferred are aliphatic and cycloaliphatic polyisocyanates, especially diisocyanates.

Specific examples of suitable aliphatic diisocyanates include alpha, omega-alkylene diisocyanates having from 5 to 20 carbon atoms, such as 1,6-hexamethylene diisocyanate, 1,12-dodecane diisocyanate, 2,2,4-trimethylhexamethylene diisocyanate, 2,4,4-trimethylhexamethylene diisocyanate, 2-methyl-1,5-pentamethylene diisocyanate, and the like. Polyisocyanates having fewer than 5 carbon atoms can be used but are less preferred because of their high volatility and toxicity. Preferred aliphatic polyisocyanates include 1,6-hexamethylene diisocyanate, 2,2,4-trimethyl-hexamethylene diisocyanate, and 2,4,4-trimethyl-hexamethylene diisocyanate.

Specific examples of suitable cycloaliphatic diisocyanates include dicyclohexylmethane diisocyanate, (commercially available as Desmodur® W from Bayer Corporation), isophorone diisocyanate, 1,4-cyclohexane diisocyanate, 1,3-bis(isocyanatomethyl)cyclohexane, and the like. Preferred cycloaliphatic diisocyanates include dicyclohexylmethane diisocyanate and isophorone diisocyanate.

Specific examples of suitable araliphatic diisocyanates include m-tetramethyl xylylene diisocyanate, p-tetramethyl xylylene diisocyanate, 1,4-xylylene diisocyanate, 1,3-xylylene diisocyanate, and the like. A preferred araliphatic diisocyanate is tetramethyl xylylene diisocyanate.

Examples of suitable aromatic diisocyanates include 4,4'-diphenylmethane diisocyanate, toluene diisocyanate, their isomers, naphthalene diisocyanate, and the like. A preferred aromatic diisocyanate is toluene diisocyanate and 4,4'-diphenylmethane diisocyanate.

Examples of high molecular weight compounds a) having 2 or more reactive groups are such as polyester polyols and polyether polyols, as well as polyhydroxy polyester amides, hydroxyl-containing polycaprolactones, hydroxyl-containing acrylic copolymers, hydroxyl-containing epoxides, polyhydroxy polycarbonates, polyhydroxy polyacetals, polyhydroxy polythioethers, polysiloxane polyols, ethoxylated polysiloxane polyols, polybutadiene polyols and hydrogenated polybutadiene polyols, polyacrylate polyols, halogenated polyesters and polyethers, and the like, and mixtures thereof. The polyester polyols, polyether polyols, polycarbonate polyols, polysiloxane polyols, and ethoxylated polysiloxane polyols are preferred. Particular preference is given to polyesterpolyols, polycarbonate polyols, polyalkylene ether polyols, and polytetrahydrofurane. The number of functional groups in the aforementioned high molecular weight compounds is preferably on average in the range from 1.8 to 3 and especially in the range from 2 to 2.2 functional groups per molecule.

The polyester polyols typically are esterification products prepared by the reaction of organic polycarboxylic acids or their anhydrides with a stoichiometric excess of a diol. The diols used in making the polyester polyols include alkylene glycols, e.g., ethylene glycol, 1,2- and 1,3-propylene glycols, 1,2-, 1,3-, 1,4-, and 2,3-butane diols, hexane diols, neopentyl glycol, 1,6-hexanediol, 1,8-octanediol, and other diols such as bisphenol-A, cyclohexanediol, cyclohexane dimethanol (1,4-bis-hydroxymethylcyclohexane), 2-methyl-1,3-propanediol, 2,2,4-trimethyl-1,3-pentanediol, diethylene glycol, triethylene glycol, tetraethylene glycol, polyethylene glycol, dipropylene glycol, polypropylene glycol, dibutylene glycol, polybutylene glycol, dimerate diol, hydroxylated bisphenols, polyether glycols, halogenated diols, and the like, and mixtures thereof. Preferred diols include ethylene glycol, diethylene glycol, butane diol, hexane diol, and neopentylglycol. Alternatively or in addition, the equivalent mercapto compounds may also be used.

Suitable carboxylic acids used in making the polyester polyols include dicarboxylic acids and tricarboxylic acids and anhydrides, e.g., maleic acid, maleic anhydride, succinic acid, glutaric acid, glutaric anhydride, adipic acid, suberic acid, pimelic acid, azelaic acid, sebacic acid, chlorendic acid, 1,2,4-butane-tricarboxylic acid, phthalic acid, the isomers of phthalic acid, phthalic anhydride, fumaric acid, dimeric fatty acids such as oleic acid, and the like, and mixtures thereof. Preferred polycarboxylic acids used in making the polyester polyols include aliphatic or aromatic dibasic acids.

Examples of suitable polyester polyols include poly(glycol adipate)s, poly(ethylene terephthalate) polyols, polycaprolactone polyols, orthophthalic polyols, sulfonated and phosphonated polyols, and the like, and mixtures thereof.

The preferred polyester polyol is a diol. Preferred polyester diols include poly(butanediol adipate); hexanediol adipic acid and isophthalic acid polyesters such as hexaneadipate isophthalate polyester; hexanediol neopentyl glycol adipic acid polyester diols, e.g., Piothane 67-3000 HNA (Panolam Industries) and Piothane 67-1000 HNA, as well as propylene glycol maleic anhydride adipic acid polyester diols, e.g., Piothane SO-1000 PMA, and hexane diol neopentyl glycol fumaric acid polyester diols, e.g., Piothane 67-SO0 HNF. Other preferred Polyester diols include Rucoflex® S101.5-3.5, S1040-3.5, and S-1040-110 (Bayer Corporation).

Polyether polyols are obtained in known manner by the reaction of a starting compound that contain reactive hydrogen atoms, such as water or the diols set forth for preparing the polyester polyols, and alkylene glycols or cyclic ethers, such as ethylene glycol, propylene glycol, butylene glycol, styrene glycol, ethylene oxide, propylene oxide, 1,2-butylene oxide, 2,3-butylene oxide, oxetane, tetrahydrofuran, epichlorohydrin, and the like, and mixtures thereof. Preferred polyethers include poly(ethylene glycol), poly(propylene glycol), polytetrahydrofuran, and co[poly(ethylene glycol)-poly(propylene glycol)]. Polyethyleneglycol and Polypropyleneglycol can be used as such or as physical blends. In case that propyleneoxide and ethyleneoxide are copolymerized, these polypropylene-co-polyethylene polymers can be used as random polymers or block-copolymers.

In one embodiment the polyetherpolyol is a constituent of the main polymer chain. In another embodiment the polyesterpolyole is a constituent of the main polymer chain. In a preferred embodiment the polyetherpolyol and the polyesterpolyol are both constituents of the main polymer chain.

In another embodiment the polyetherol is a terminal group of the main polymer chain. In yet another embodiment the polyetherpolyol is a constituent of a side chain which is comb-like attached to the main chain. An example of such a monomer is Tegomer D-3403 (Degussa). Polycarbonates include those obtained from the reaction of diols such 1,3-propanediol, 1,4-butanediol, 1,6-hexanediol, diethylene glycol, triethylene glycol, tetraethylene glycol, and the like, and mixtures thereof with dialkyl carbonates such as diethyl carbonate, diaryl carbonates such as diphenyl carbonate or phosgene.

Examples of low molecular weight compounds b) having two reactive functional groups are the diols such as alkylene glycols and other diols mentioned above in connection with the preparation of polyesterpolyols. They also include diamines such as diamines and polyamines, which are among the preferred compounds useful in preparing the polyesteramides and polyamides. Suitable diamines and polyamines include 1,2-diaminoethane, 1,6-diaminohexane, 2-methyl-1,5-pentanediamine, 2,2,4-trimethyl-1,6-hexanediamine, 1,12-diaminododecane, 2-aminoethanol, 2-[(2-aminoethyl)amino]-ethanol, piperazine, 2,5-dimethylpiperazine, 1-amino-3-aminomethyl-3,5,5-trimethylcyclohexane (isophorone diamine or IPDA), bis-(4-aminocyclohexyl)-methane, bis-(4-amino-3-methyl-cyclohexyl)-methane, 1,4-diaminocyclohexane, 1,2-propylenediamine, hydrazine, urea, amino acid hydrazides, hydrazides of semicarbazidocarboxylic acids, bis-hydrazides and bis-semicarbazides, diethylene triamine, triethylene tetramine, tetraethylene pentamine, pentaethylene hexamine, N,N,N-tris-(2-aminoethyl)amine, N-(2-piperazinoethyl)-ethylene diamine, N,N'-bis-(2-aminoethyl)-piperazine, N,N,N'-tris-(2-aminoethyl)ethylene diamine, N—[N-(2-aminoethyl)-2-aminoethyl]-N'-(2-aminoethyl)-piperazine, N-(2-aminoethyl)-N'-(2-piperazinoethyl)-ethylene diamine, N,N-bis-(2-aminoethyl)-N-(2-piperazinoethyl)amine, N,N-bis-(2-piperazinoethyl)amine, polyethylene imines, iminobispropylamine, guanidine, melamine, N-(2-aminoethyl)-1,3-propane diamine, 3,3'-diaminobenzidine, 2,4,6-triaminopyrimidine, polyoxypropylene amines, tetrapropylenepentamine, tripropylenetetramine, N,N-bis-(6-aminohexyl)amine, N,N'-bis-(3-aminopropyl)ethylene diamine, and 2,4-bis-(4'-aminobenzyl)-aniline, and the like, and mixtures thereof. Preferred diamines and polyamines include 1-amino-3-aminomethyl-3,5,5-trimethyl-cyclohexane (isophorone diamine or IPDA), bis-(4-aminocyclohexyl)-methane, bis-(4-amino-3-methylcyclohexyl)methane, ethylene diamine, diethylene triamine, triethylene tetramine, tetraethylene pentamine, and pentaethylene hexamine, and the like, and mixtures thereof. Other suitable diamines and polyamines for example include Jeffamine® D-2000 and D-4000, which are amine-terminated polypropylene glycols differing only by molecular weight, and Jeffamine® XTJ-502, T 403, T 5000, and T 3000 which are amine terminated polyethyleneglycols, amine terminated copolypropylene-polyethylene glycols, and triamines based on propoxylated glycerol or trimethylolpropane and which are available from Huntsman Chemical Company.

The poly(alkylene glycol) may be part of the polymer main chain or be attached to the main chain in comb-like shape as a side chain.

In a preferred embodiment, the polyurethane comprises poly(alkylene glycol) side chains sufficient in amount to comprise about 10 wt. % to 90 wt. %, preferably about 12 wt. % to about 80 wt. %, preferably about 15 wt. % to about 60 wt. %, and more preferably about 20 wt. % to about 50 wt. %, of poly(alkylene glycol) units in the final polyurethane on a dry weight basis. At least about 50 wt. %, preferably at least about 70 wt. %, and more preferably at least about 90 wt. % of the poly(alkylene glycol) side-chain units comprise poly(ethylene glycol), and the remainder of the side-chain poly-(alkylene glycol) units can comprise alkylene glycol and substituted alkylene glycol units having from 3 to about 10 carbon atoms. The term "final polyurethane" means the polyurethane used for coating the water-absorbing polymeric particles.

Preferably the amount of the side-chain units is (i) at least about 30 wt. % when the molecular weight of the side-chain units is less than about 600 g/mol, (ii) at least about 15 wt. % when the molecular weight of the side-chain units is from about 600 to about 1000 g/mol, and (iii) at least about 12 wt. % when the molecular weight of said side-chain units is more than about 1000 g/mol. Mixtures of active hydrogen-containing compounds having such poly(alkylene glycol) side chains can be used with active hydrogen-containing compounds not having such side chains.

These side chains can be incorporated in the polyurethane by replacing a part or all of the aforementioned high molecular diols a) or low molecular compounds b) by compounds c) having at least two reactive functional groups and a polyether group, preferably a polyalkylene ether group, more preferably a polyethylene glycol group that has no reactive group.

For example, active hydrogen-containing compounds having a polyether group, in particular a poly(alkylene glycol) group, include diols having poly(ethylene glycol) groups such as those described in U.S. Pat. No. 3,905,929 (incorporated herein by reference in its entirety). Further, U.S. Pat. No. 5,700,867 (incorporated herein by reference in its entirety) teaches methods for incorporation of poly(ethylene glycol) side chains at col. 4, line 3.5 to col. 5, line 4.5. A preferred active hydrogen-containing compound having poly(ethylene glycol) side chains is trimethylol propane mono(polyethylene oxide methyl ether), available as Tegomer D-3403 from Degussa-Goldschmidt. Another method to incorporate poly(ethylene glycol) as a side chain into the main polymer chain is described in DE 2 730 514 (incorporated herein by reference in its entirety). According to this method a diisocyanate having two isocyanate groups of different reactivity is reacted with a HO-monofunctional poly(ethyleneoxide) in stoichiometric ratio (1 mole:1 mole), and subsequently the second isocyanate group is reacted in stoichiometric ratio (1 mole:1 mole) with a dialkanoleamine to form a diole. Such diole can be then incorporated by the conventional techniques. Suitable isocyanates are for example isophoronediisocyanate, a suitable dialkanoleamine is diethanolamine.

Preferably, the polyurethanes to be used in the present invention also have reacted therein at least one active hydrogen-containing compound not having said side chains and typically ranging widely in molecular weight from about 50 to about 10000 g/mol, preferably about 200 to about 6000 g/mol, and more preferably about 300 to about 3000 g/mol. Suitable active hydrogen-containing compounds not having said side chains include any of the amines and polyols described herein as compounds a) and b).

According to one preferred embodiment of the invention, the active hydrogen compounds are chosen to provide less than about 25 wt. %, more preferably less than about 15 wt. % and most preferably less than about 5 wt. % poly(ethylene glycol) units in the backbone (main chain) based upon the dry weight of final polyurethane, since such main-chain poly(ethylene glycol) units tend to cause swelling of polyurethane particles in the waterborne polyurethane dispersion and also contribute to lower in use tensile strength of articles made from the polyurethane dispersion.

The preparation of polyurethanes having polyether side chains is known to one skilled in the art and is extensively described for example in US 2003/0195293, which is hereby expressly incorporated herein by reference.

The present invention accordingly also provides a water-absorbing material comprising water-absorbing polymeric particles coated with an elastic film-forming polyurethane, wherein the polyurethane comprises not only side chains having polyethylene oxide units but also polyethylene oxide units in the main chain.

Advantageous polyurethanes within the realm of this invention are obtained by first preparing prepolymers having isocyanate end groups, which are subsequently linked together in a chain-extending step. The linking together can be through water or through reaction with a compound having at least one crosslinkable functional group.

The prepolymer is obtained by reacting one of the above-described isocyanate compounds with an active hydrogen compound. Preferably the prepolymer is prepared from the above-mentioned polyisocyanates, at least one compound c) and optionally at least one further active hydrogen compound selected from the compounds a) and b).

In one embodiment the ratio of isocyanate to active hydrogen in the compounds forming the prepolymer typically ranges from about 1.3/1 to about 2.5/1, preferably from about 1.5/1 to about 2.1/1, and more preferably from about 1.7/1 to about 2/1.

The polyurethane may additionally contain functional groups which can undergo further crosslinking reactions and which can optionally render them self-crosslinkable.

Compounds having at least one additional crosslinkable functional group include those having carboxylic, carbonyl, amine, hydroxyl, and hydrazide groups, and the like, and mixtures of such groups. The typical amount of such optional compound is up to about 1 milliequivalent, preferably from about 0.05 to about 0.5 milliequivalent, and more preferably from about 0.1 to about 0.3 milliequivalent per gram of final polyurethane on a dry weight basis.

The preferred monomers for incorporation into the isocyanate-terminated prepolymer are hydroxy-carboxylic acids having the general formula $(HO)_xQ(COOH)_y$ wherein Q is a straight or branched hydrocarbon radical having 1 to 12 carbon atoms, and x and y are 1 to 3. Examples of such hydroxy-carboxylic acids include citric acid, dimethylolpropanoic acid (DMPA), dimethylol butanoic acid (DMBA), glycolic acid, lactic acid, malic acid, dihydroxymalic acid, tartaric acid, hydroxypivalic acid, and the like, and mixtures thereof. Dihydroxy-carboxylic acids are more preferred with dimethylolpropanoic acid (DMPA) being most preferred.

Other suitable compounds providing crosslinkability include thioglycolic acid, 2,6-dihydroxybenzoic acid, and the like, and mixtures thereof.

Optional neutralization of the prepolymer having pendant carboxyl groups converts the carboxyl groups to carboxylate anions, thus having a water-dispersibility enhancing effect. Suitable neutralizing agents include tertiary amines, metal hydroxides, ammonia, and other agents well known to those skilled in the art.

As a chain extender, at least one of water, an inorganic or organic polyamine having an average of about 2 or more primary and/or secondary amine groups, polyalcohols, ureas, or combinations thereof is suitable for use in the present invention. Suitable organic amines for use as a chain extender include diethylene triamine (DETA), ethylene diamine (EDA), metaxylylenediamine (MXDA), aminoethyl ethanolamine (AEEA), 2-methyl pentane diamine, isophoronediamine (IPDA), and the like, and mixtures thereof. Also suitable for practice in the pre-sent invention are propylene diamine, butylene diamine, hexamethylene diamine, cyclohexylene diamine, phenylene diamine, tolylene diamine, 3,3-dichlorobenzidene, 4,4'-methylene-bis-(2-chloroaniline), 3,3-dichloro-4,4-diamino diphenylmethane, sulfonated primary and/or secondary amines, and the like, and mixtures thereof. Suitable inorganic and organic amines include hydrazine, substituted hydrazines, and hydrazine reaction products, and the like, and mixtures thereof. Suitable polyalcohols include those having from 2 to 12 carbon atoms, preferably from 2 to 8 carbon atoms, such as ethylene glycol, diethylene glycol, neopentyl glycol, butanediols, hexanediol, and the like, and mixtures thereof. Suitable ureas include urea and its derivatives, and the like, and mixtures thereof. Hydrazine is preferred and is most preferably used as a solution in water. The amount of chain extender typically ranges from about 0.5 to about 0.95 equivalents based on available isocyanate.

A degree of branching of the polyurethane may be beneficial, but is not required to maintain a high tensile strength and improve resistance to creep (cf. strain relaxation). This degree of branching may be accomplished during the prepolymer step or the extension step. For branching during the extension step, the chain extender DETA is preferred, but other amines having an average of about two or more primary and/or secondary amine groups may also be used. For branching during the prepolymer step, it is preferred that trimethylol propane (TMP) and other polyols having an average of more than two hydroxyl groups be used. The branching monomers can be present in amounts up to about 4 wt. % of the polymer backbone.

Polyurethanes are preferred film-forming polymers. They can be applied to the water-absorbing polymer particles as a solution or as a dispersion. Particularly preferred are aqueous dispersions.

Preferred aqueous polyurethane dispersions are Hauthane HD-4638 (ex Hauthaway), Hydrolar® HC 269 (ex COIMolm, Italy), Impraperm® 48180 (ex Bayer Material Science AG, Germany), Lurapret® DPS (ex BASF Aktiengesellschaft, Germany), Astacin® Finish LD 1603 (ex BASF Aktiengesellschaft, Germany), Permax® 120, Permax 200, and Permax 220 (ex Noveon, Brecksville, Ohio), Syntegra YM2000 and Syntegra YM2100 (ex Dow, Midland, Mich.), Witcobond® G-213, Witcobond G-506, Witcobond G-507, Witcobond 736 (ex Uniroyal Chemical, Middlebury, Conn.), Astacin Finish PUMN TF, Astacin TOP 140, Astacin Finish SUSI (all ex BASF) and Impranil® DLF (anionic aliphatic polyester-polyurethan dispersion from Bayer Material Science)

Particularly suitable elastic film-forming polyurethanes are extensively described in the literature references hereinbelow and expressly form part of the subject matter of the present disclosure. Particularly hydrophilic thermoplastic polyurethanes are sold by Noveon, Brecksville, Ohio, under the tradenames of Permax 120, Permax 200 and Permax 220 and are described in detail in "Proceedings International Waterborne High Solids Coatings, 32, 299, 2004" and were presented to the public in February 2004 at the "International Waterborne, High-Solids, and Powder Coatings Symposium" in New Orleans, USA. The preparation is described in detail in US 2003/0195293.

Furthermore, the polyurethanes described in U.S. Pat. No. 4,190,566, U.S. Pat. No. 4,092,286, US 2004/0214937 and also WO 03/050156 expressly form part of the subject matter of the present disclosure.

More particularly, the polyurethanes described can be used in mixtures with each other or with other film-forming polymers, fillers, oils, blowing aids, water-soluble polymers or plasticizing agents in order that particularly advantageous properties may be achieved with regard to hydrophilicity, water perviousness and mechanical properties. Polymers that are suitable for blending with polyurethane dispersions are in many cases also suitable to accomplish a sufficiently good coating when used alone.

In a particularly preferred embodiment the film forming polymer dispersion, most preferably a polyurethane dispersion, is blended with at least one other polymer dispersion selected for example from poly-co(ethylene-vinylacetate), polyacetale and homo- and copolymers comprising acrylonitrile, butadiene, styrene, (meth-)acrylate, isoprene or vinylpyrrolidone. (Meth)acrylate shall mean methacrylic acid and acrylic acid and all their respective derivatives, especially their esters. Blending can be done in any ratio, however particularly preferred are blending ratios that will lead to films on the water absorbing polymeric particles which yield comparable performance properties of the coated water-absorbing polymeric particles as would have otherwise been obtained by a coating with the unblended film forming polymers. Examples of such suitable dispersion for blending are Lepton® TOP LB (aqueous polyacrylate and wax dispersion, BASF Aktiengesellschaft), Airflex EP 17V (aqueous Vinylacetate-Ethylene-Copolymer dispersion, Air Products B.V.), Epotal® 480 (aqueous styrene-acrylonitrile-acrylate dispersion, BASF Aktiengesellschaft), Poligen® MA (hard film forming aqueous polyacrylate dispersion, BASF Aktiengesellschaft), Corial Binder OK (medium hard film forming aqueous polyacrylate dispersion, BASF Aktiengesellschaft), Corial Binder IF (soft film forming aqueous polyacrylate dispersion, BASF Aktiengesellschaft), Corial Ultrasoft NT (very soft film forming aqueous polyacrylate dispersion, BASF Aktiengesellschaft) and Mowilith® DM 799 from Celanese Emulsion GmbH (hard film forming anionic stabilized Acryl-/Methacrylate Polymer dispersion, OH-number ~18 [b.o. polymer], MFT ~90° C., Tg ~110° C.)

In another particularly preferred embodiment in a first step one film forming polymer dispersion, most preferably a polyurethane dispersion is applied onto the surface of the water absorbing particles followed by at least one second step applying a different film forming polymer dispersion onto the surface of the already coated water absorbing particles. This second film-forming polymer is most preferably not a polyurethane but forms a film, which is preferably less tacky than the polyurethane. Examples of such suitable dispersions are already described in the section before and encompass Lepton LB, Epotal A 480, Corial Binder IF, Mowilith DM 799, Airflex EP 17V.

In a most preferred embodiment this second film is more hydrophilic than the polyurethane. Preferred is a process, wherein the second, non polyurethane dispersion, which forms more hydrophilic films than polyurethanes is sprayed separately either immediately after coating the polyurethane dispersion before subsequent heat treatment according to step b) or finally after the heat treatment.

In case an aqueous polymer dispersion is used it may be preferred that the dispersion is self-emulating without the need to use excessive amounts of surfactants or without using any surfactants. Such properties are common for polyurethane dispersions and for some polyacrylate and other polymer dispersions which are commonly called hydroresins.

It may be preferred that the coating agent herein comprises fillers to reduce tack such as the commercially available resin Estane 58245-047P and Estane X-1007-040P, available from Noveon Inc., 9911 Brecksville Road, Cleveland, Ohio 44141-3247, USA.

Alternatively such fillers can be added in order to reduce tack and/or to improve other elastic properties of the film forming polymer to the dispersions or solutions of suitable elastomeric polymers before application. Typical fillers are Aerosil® (Degussa), Levasil® (H.C. Starck GmbH) or Ultrasil® (Degussa), but other inorganic deagglomeration aids as listed below can also be used. For example clay, titaniumdioxide, aluminumoxide, bor phosphate, iron phosphate, inorganic carbonates, aluminum phosphate, or Polyhedral Oligomeric Silsesquioxanes (POSS®) available from Hybrid Plastics (USA) can also be used. A particularly preferred filler is nano-particulate Calciumphosphate. Such fillers may improve also the functionality of the elastomeric coating beyond tackiness as they typically exhibit a reinforcing effect on the elastomeric polymer.

Preferred polyurethanes for use in the coating agent herein are strain hardening and/or strain crystallizing. Strain hardening is observed during stress-strain measurements, and is evidenced as the rapid increase in stress with increasing strain. It is generally believed that strain hardening is caused by orientation of the polymer chains in the film producing greater resistance to extension in the direction of drawing.

The coating agent is applied such that the resulting coating layer is preferably thin having an average calculated caliper (thickness) in the dry state of more than 0.1 μm; preferably the coating layer has an average caliper (thickness) from 1 micron (μm) to 100 microns, preferably from 1 micron to 50 microns, more preferably from 1 micron to 20 microns or even from 2 to 20 microns or even from 2 to 10 microns.

In one embodiment the coating is preferably virtually uniform in caliper and/or shape. Preferably, the average caliper is such that the ratio of the smallest to largest caliper is from 1:1 to 1:5, preferably from 1:1 to 1:3, or even 1:1 to 1:2, or even 1:1 to 1:1.5.

In another embodiment the coating may show some defects (i.e. holes) but still the polymer shows very good performance properties according to the present invention. In yet another embodiment of the invention, the coating may form a fibrous net around the water-absorbing particles.

The polymeric film is preferably applied in an amount of 0.01-25 parts by weight of the film-forming polymer (calculated as solids material) to 100 parts by weight of dry water-absorbing polymeric particles. The amount of film-forming polymer used per 100 parts by weight of water-absorbing polymeric particles is preferably 0.1-25 parts by weight, especially 0.1-15 parts by weight, especially 0.5-10 parts by weight, more preferably 0.5-7 parts by weight, even more preferably 0.5-5 parts by weight and in particular 0.5-4.5 parts by weight.

Particular preference is given to a water-absorbing material obtained by coating water-absorbing polymeric particles with <5 parts by weight, preferably 0.5-4.5 parts by weight, especially 0.5-4 parts by weight and more preferably 0.5-3 parts by weight of film-forming polymer based on 100 parts by weight of water-absorbing polymeric particles, preferably at temperatures in the range from 0° C. to <150° C., preferably from 20° C. to <100° C., more preferably from 40° C. to <90° C., and most preferably from 50° C. to <80° C., and then heat-treatment the coated particles at a temperature above 50° C.

The film-forming polymer can be applied as a solid material, as a hotmelt, as a dispersion, as an aqueous dispersion, as an aqueous solution or as an organic solution to the particles of the water-absorbing addition polymer. The form in which the film-forming polymer, especially the polyurethane is applied to the water-absorbing polymeric particles is preferably as a solution or more preferably as an aqueous dispersion.

Useful solvents for polyurethanes include solvents, which make it possible to establish 1 to not less than 40% by weight concentrations of the polyurethane in the respective solvent or mixture. As examples there may be mentioned alcohols, esters, ethers, ketones, amides, and halogenated hydrocarbons; examples include methyl ethyl ketone, acetone, isopropanol, tetrahydrofuran, dimethylformamide, N-methylpyrrolidone, chloroform and mixtures thereof. Solvents which are polar, aprotic and boil below 100° C. are particularly advantageous.

In case an aqueous dispersion of the film-building polymer is used together with a coalescing agent as described below then any solvent other than water and not desired to function as coalescing agent should be excluded from the dispersion.

It is particularly preferable to effect the coating in a fluidized bed reactor. The water-absorbing particles are introduced as generally customary, depending on the type of the reactor, and are generally coated by spraying with the film-forming polymer as a solid material or preferably as a polymeric solution or dispersion. Aqueous dispersions of the film-forming polymer are particularly preferred for this.

The polyurethane solution or dispersion applied by spray-coating is preferably very concentrated. For this, the viscosity of this polyurethane mixture must not be too high, or the polyurethane solution or dispersion can no longer be finely dispersed for spraying. Preference is given to an aqueous polymeric dispersion especially a polyurethane solution or dispersion having a viscosity of <500 mPa·s, preferably of <300 mPa·s, more preferably of <100 mPa·s, even more preferably of <10 mPa·s, and most preferably <5 mPa·s (typically determined with a rotary viscometer at a shear rate ≧200 rpm for the polyurethane dispersion, and specifically suitable is a Haake rotary viscometer type RV20, system M5, NV). The abovementioned viscosities are preferably exhibited at a temperature of 15-40° C., more preferably at 18-25° C. However, if the dispersion or solution is sprayed at an elevated temperature it is sufficient if the above-mentioned viscosities are exhibited at such elevated application temperature.

In embodiments in which other film-forming polymers or their mixtures with polyurethanes as blends of polymer dispersions are used, it is preferred that these exhibit the same viscosities as the polyurethanes when applied.

The concentration of polyurethane in the polyurethane solution or dispersion is generally in the range from 1% to 60% by weight, preferably in the range from 5% to 40% by weight and especially in the range from 10% to 30% by weight. Higher dilutions are possible, but generally lead to longer coating times. A particular advantage of polyurethane dispersions is their relatively low viscosity even at high concentrations and high molecular weights.

Fluidized bed in the context of the present invention means that the polymeric particles are carried upwards in erratic motion and maintained in a fluidized state by a gas stream or are maintained in an equivalent state by good mixing and reduction of density. Continuous means that uncoated water-absorbing polymeric particles are continuously fed to the coater and that coated water-absorbing polymeric particles are continuously discharged from the coater after passing all spraying-zones inside the coater.

Useful fluidized bed reactors include for example the fluidized or suspended bed coaters familiar in the pharmaceutical industry. Particular preference is given to reactors using the Wurster principles or the Glatt-Zeller principles which are described for example in "Pharmazeutische Technologie, Georg Thieme Verlag, 2nd edition (1989), pages 412-413" and also in "Arzneiformenlehre, Wissenschaftliche Verlagsbuchandlung mbH, Stuttgart 1985, pages 130-132". Particularly suitable batch and continuous fluidized bed processes on a commercial scale are described in Drying Technology, 20(2), 419-447 (2002).

According to the Wurster process the water-absorbing polymeric particles are carried by an upwardly directed stream of carrier gas in a central tube, against the force of gravity, past at least one spray nozzle and are sprayed concurrently with the finely dispersed polymeric solution or dispersion. The particles thereafter fall back to the base along the side walls, are collected on the base, and are again carried by the flow of carrier gas through the central tube past the spray nozzle. The spray nozzle typically sprays from the bottom into the fluidized bed, it can also project from the bottom into the fluidized bed.

According to the Glatt-Zeller process, the water-absorbing polymeric particles are conveyed by the carrier gas on the outside along the walls in the upward direction and then fall in the middle onto a central nozzle head, which typically comprises at least 3 two-material nozzles, which spray to the side. The particles are thus sprayed from the side, fall past the nozzle head to the base and are taken up again there by the carrier gas, so that the cycle can start anew.

The feature common to the two processes is that the particles are repeatedly carried in the form of a fluidized bed past the spray device, whereby a very thin and typically very homogeneous shell can be applied. Furthermore, a carrier gas is used at all times and it has to be fed and moved at a sufficiently high rate to maintain fluidization of the particles. As a result, liquids are rapidly vaporized in the apparatus, such as for example the solvent (i.e. water) of the dispersion, even at low temperatures, whereby the polymeric particles of the dispersion are layed down onto the surface of the particles of the water-absorbing polymer, which are to be coated. Useful carrier gases include the inert gases mentioned above and air, dehumidified air or dried air or mixtures of any of these gases.

Suitable fluidized bed reactors work according to the principle that the film-forming polymer solution or dispersion is finely sprayed (="atomized") and the droplets randomly collide with the water-absorbing polymer particles in a fluidized bed, whereby a substantially homogeneous shell builds up gradually and uniformly after many collisions. The size of the droplets must be inferior to the particle size of the absorbent polymer. Droplet size is determined by the type of nozzle, the spraying conditions i.e. temperature, concentration, viscosity and pressure. Typical droplets sizes are in the range 1 µm to 400 µm. A polymer particle size vs. droplet size ratio of at least 10 is typically observed. Small droplets with a narrow size distribution are favourable. The droplets of the "atomized" polymeric dispersion or solution are introduced either concurrently with the particle flow or from the side into the particle flow, and may also be sprayed from the top onto a fluidized bed. In this sense, other apparatus and equipment modifications, which comply with this principle and which are likewise capable of building up fluidized beds are perfectly suitable for producing such effects.

One embodiment, for example, is a cylindrical fluidized bed batch reactor, in which the water-absorbing polymer particles are transported upwards by a carrier-gas stream at the outer walls inside the apparatus and from one or more positions a film-forming polymer spray is applied from the side into this fluidized bed, whereas in the middle zone of the apparatus, in which there is no carrier gas stream at all and where the particles fall down again, a cubic agitator is moving and redistributing the entire fluidized particle bed.

Other embodiments, for example, may be Schuggi mixers, turbolizers or plowshare mixers, which can be used alone or preferably as a battery of plural consecutive units. If such a mixer is used alone, the water-absorbing polymer may have to be fed multiple times through the apparatus to become homogeneously coated. If two or more of such apparatus are set up as consecutive units then one pass may be sufficient.

In another embodiment continuous spray-mixers using the principles of the Telschig-type are used in which the spray hits free falling particles in-flight, the particles being repeatedly exposed to the spray. Suitable mixers are described in Chemie-Technik, 22 (1993), Nr. 4, p. 98 ff.

In a preferred embodiment, a continuous fluidized bed process is used and preferably the spray is operated in top or bottom-mode. In a particularly preferred embodiment the spray is operated bottom-mode and the process is continuous. A suitable apparatus is for example described in U.S. Pat. No. 5,211,985. Suitable apparatus are available also for example from Glatt Maschinen- und Apparatebau AG (Switzerland) as series GF (continuous fluidized bed) and as ProCell® spouted bed. The spouted bed technology uses a simple slot instead of a screen bottom to generate the fluidized bed and is particularly suitable for materials, which are difficult to fluidize.

In other embodiments it may also be desired to operate the spray top- and bottom-mode, or it may be desired to spray from the side or from a combination of several different spray positions.

The process of the present invention utilizes the aforementioned nozzles, which are customarily used for post-crosslinking. However, two-material nozzles are particularly preferred.

Preferred is a process wherein the fluidized bed reactor is a Wurster Coater or a Glatt-Zeller coater or a fluidized bed reactor equipped with spray nozzles.

The process of the present invention preferably utilizes Wurster Coaters. Examples for such coaters are PRECISION COATERS™ available from GEA-Aeromatic Fielder AG (Switzerland) and are accessible at Coating Place Inc. (Wisconsin, USA).

It is advantageous that the fluidized bed gas stream, which enters from below is likewise chosen such that the total amount of the water-absorbing polymeric particles is fluidized in the apparatus. The gas velocity for the fluidized bed is above the minimum fluidization velocity (measurement method described in Kunii and Levenspiel "Fluidization engineering" 1991) and below the terminal velocity of water-absorbing polymer particles, preferably 10% above the minimum fluidization velocity. The gas velocity for the Wurster tube is above the terminal velocity of water-absorbing polymer particles, usually below 100 m/s, preferably 10% above the terminal velocity.

The gas stream acts to vaporize the water, or the solvents. In a preferred embodiment, the coating conditions of gas stream and temperature are chosen so that the relative humidity or vapor saturation at the exit of the gas stream is in the range from 0.10% to 90%, preferably from 1% to 80%, or preferably from 10% to 70% and especially from 30% to 60%, based on the equivalent absolute humidity prevailing in the carrier gas at the same temperature or, if appropriate, the absolute saturation vapor pressure.

The fluidized bed reactor may be built from stainless steel or any other typical material used for such reactors, also the product contacting parts may be stainless steel to accommodate the use of organic solvents and high temperatures.

In a further embodiment, the inner surfaces of the fluidized bed reactor are at least partially coated with a material whose contact angle with water is more than 90° at 25° C. Teflon or polypropylene are examples of such a material. Preferably, all product-contacting parts of the apparatus are coated with this material. However, if the product is abrasive then such coating material must be sufficiently resistant to abrasion.

The choice of material for the product-contacting parts of the apparatus, however, also depends on whether these materials exhibit strong adhesion to the utilized polymeric dispersion or solution or to the polymers to be coated. Preference is given to selecting materials which have no such adhesion either to the polymer to be coated or to the polymer dispersion or solution in order that caking may be avoided.

It is preferred herein that the coating takes place at a product and/or carrier gas temperature in the range from 0° C. to 150° C., preferably from 20 to 100° C., especially from 40 to 90° C. and most preferably from 50 to 80° C.

According to one embodiment of the present invention, an antioxidant is added in step a) and/or b), preferably in step a).

Antioxidants, also called inhibitors (of oxidation), are organic compounds that are added to oxidizable organic materials to retard autooxidation and to retard oxidative processes in the substrate, in general, to prolong the useful life and performance properties of the substrates. Antioxidants are agents that are capable to reduce or suppress degradation of the film forming polymer by oxidative stress, especially during the heat treatment step subsequent to coating, but also during extended storage of the products.

Antioxidants are for example hindered phenols, secondary aromatic amines, certain sulfide esters, trivalent phosphorus compounds, hindered amines, metal dithiocarbamates, and metal dithiophosphates.

The group of the antioxidants comprises, for example:

alkylated monophenols, such as, for example, 2,6-di(tert-butyl)-4-methylphenol, 2-(tert-butyl)-4,6-dimethylphenol, 2,6-di(tert-butyl)-4-ethylphenol, 2,6-di(tert-butyl)-4-(n-butyl)phenol, 2,6-di(tert-butyl)-4-isobutylphenol, 2,6-dicyclopentyl-4-methylphenol, 2-α-methylcyclohexyl)-4,6-dimethylphenol, 2,6-dioctadecyl-4-methylphenol, 2,4,6-tricyclohexylphenol, 2,6-di(tert-butyl)-4-methoxymethylphenol, unbranched nonylphenols or nonylphenols which are branched in the side chain, such as, for example, 2,6-dinonyl-4-methylphenol, 2,4-dimethyl-6-(1-methylundec-1-yl)phenol, 2,4-dimethyl-6-(1-methylheptadec-1-yl)phenol, 2,4-dimethyl-6-(1-methyltridec-1-yl) phenol and mixtures thereof.

Alkylthiomethylphenols, such as, for example, 2,4-dioctylthiomethyl-6-(tert-butyl)phenol, 2,4-dioctylthiomethyl-6-methylphenol, 2,4-dioctylthiomethyl-6-ethylphenol and 2,6-didodecylthiomethyl-4-nonylphenol.

Hydroquinones and alkylated hydroquinones, such as, for example, 2,6-di(tert-butyl)-4-methoxyphenol, 2,5-di(tert-butyl)hydroquinone, 2,5-di(tert-amyl)hydroquinone, 2,6-diphenyl-4-octadecyloxyphenol, 2,6-di(tert-butyl)hydroquinone, 2,5-di(tert-butyl)-4-hydroxyanisole, 3,5-di(tert-butyl)-4-hydroxyanisole, 3,5-di(tert-butyl)-4-hydroxyphenyl stearate and bis(3,5-di(tert-butyl)-4-hydroxyphenyl) adipate.

Tocopherols, such as, for example, α-tocopherol, β-tocopherol, γ-tocopherol, δ-tocopherol and mixtures thereof (vitamin E), vitamin E acetate, vitamin E phosphate, and chromanol and its derivatives.

Hydroxylated thiodiphenyl ethers, such as, for example, 2,2'-thiobis(6-(tert-butyl)-4-methylphenol), 2,2'-thiobis(4-octylphenol), 4,4'-thiobis(6-(tert-butyl)-3-methylphenol), 4,4'-thiobis(6-(tert-butyl)-2-methylphenol), 4,4'-thiobis(3,6-di(sec-amyl)phenol) and 4,4'-bis(2,6-dimethyl-4-hydroxyphenyl)disulfide.

Alkylidenebisphenols, such as, for example, 2,2'-methylenebis(6-(tert-butyl)-4-methylphenol), 2,2'-methylenebis(6-(tert-butyl)-4-ethylphenol), 2,2'-methylenebis[4-methyl-6-α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di(tert-butyl)phenol), 2,2'-ethylidenebis(4,6-di(tert-butyl)phenol), 2,2'-ethylidenebis(6-(tert-butyl)-4-isobutylphenol), 2,2'-methylenebis[6-α-methylbenzyl)-4-nonylphenol], 2,2'-methylenebis[6-(α,α-dimethylbenzyl)-4-nonylphenol], 4,4'-methylenebis(2,6-di(tert-butyl)phenol), 4,4'-methylenebis(6-(tert-butyl)-2-methylphenol), 1,1-bis(5-(tert-butyl)-4-hydroxy-2-methylphenyl)butane, 2,6-bis(3-(tert-butyl)-5-methyl-2-hydroxybenzyl)-4-methylphenol, 1,1,3-tris(5-(tert-butyl)-4-hydroxy-2-methylphenyl)butane, 1,1-bis(5-(tert-butyl)-4-hydroxy-2-methylphenyl)-3-(n-dodecylmercapto)butane, ethylene glycol bis[3,3-bis(3-(tert-butyl)-4-hydroxyphenyl)butyrate], bis(3-(tert-butyl)-4-hydroxy-5-methylphenyl)dicyclopentadiene, bis[2-(3'-(tert-butyl)-2-hydroxy-5-methylbenzyl)-6-(tert-butyl)-4-methylphenyl]terephthalate, 1,1-bis(3,5-dimethyl-2-hydroxyphenyl)butane, 2,2-bis(3,5-di(tert-butyl)-4-hydroxyphenyl)propane, 2,2-bis(5-(tert-butyl)-4-hydroxy-2-methylphenyl)-4-(n-dodecylmercapto)butane and 1,1,5,5-tetra(5-(tert-butyl)-4-hydroxy-2-methylphenyl)pentane.

Benzyl compounds, such as, for example, 3,5,3',5'-tetra(tert-butyl)-4,4'-dihydroxydibenzyl ether, octadecyl 4-hydroxy-3,5-dimethylbenzylmercaptoacetate, tridecyl 4-hydroxy-3,5-di(tertbutyl)benzylmercaptoacetate, tris(3,5-di(tert-butyl)-4-hydroxybenzyl)amine, 1,3,5-tri(3,5-di(tert-butyl)-4-hydroxybenzyl)-2,4,6-trimethylbenzene, di(3,5-di(tert-butyl)-4-hydroxybenzyl)sulfide, isooctyl 3,5-di(tert-butyl)-4-hydroxybenzylmercaptoacetate, bis(4-(tert-butyl)-3-hydroxy-2,6-dimethylbenzyl)dithioterephthalate, 1,3,5-tris(3,5-di(tert-butyl)-4-hydroxybenzyl)isocyanurate, 1,3,5-tris(4-(tert-butyl)-3-hydroxy-2,6-dimethylbenzyl) isocyanurate, 3,5-di(tert-butyl)-4-hydroxybenzyl dioctadecyl phosphate and 3,5-di(tert-butyl)-4-hydroxybenzyl monoethyl phosphate, calcium salt.

Hydroxybenzylated malonates, such as, for example, dioctadecyl 2,2-bis(3,5-di(tert-butyl)-2-hydroxybenzyl)malonate, dioctadecyl 2-(3-(tert-butyl)-4-hydroxy-5-methylbenzyl)malonate, didodecylmercaptoethyl 2,2-bis(3,5-di(tert-butyl)-4-hydroxybenzyl)malonate and bis[4-(1,1,3,3-tetramethylbutyl)phenyl]2,2-bis(3,5-di(tert-butyl)-4-hydroxybenzyl)malonate.

Hydroxybenzyl aromatic compounds, such as, for example, 1,3,5-tris(3,5-di(tert-butyl)-4-hydroxybenzyl)-2,4,6-trimethylbenzene, 1,4-bis(3,5-di(tert-butyl)-4-hydroxybenzyl)-2,3,5,6-tetramethylbenzene and 2,4,6-tris(3,5-di(tert-butyl)-4-hydroxybenzyl)phenol.

Triazine compounds, such as, for example, 2,4-bis(octylmercapto)-6-(3,5-di(tert-butyl)-4-hydroxyanilino)-1,3,5-triazine, 2-octylmercapto-4,6-bis(3,5-di(tert-butyl)-4-hydroxyanilino)-1,3,5-triazine, 2-octylmercapto-4,6-bis(3,5-di(tert-butyl)-4-hydroxyphenoxy)-1,3,5-triazine, 2,4,6-tris(3,5-di(tert-butyl)-4-hydroxyphenoxy)-1,3,5-triazine, 1,3,5-tris(3,5-di(tert-butyl)-4-hydroxybenzyl)isocyanurate, 1,3,5-tris(4-(tert-butyl)-3-hydroxy-2,6-dimethylbenzyl)isocyanurate, 2,4,6-tris(3,5-di(tert-butyl)-4-hydroxyphenylethyl)-1,3,5-triazine, 1,3,5-tris(3,5-di(tert-butyl)-4-hydroxyphenylpropionyl)-hexahydro-1,3,5-triazine and 1,3,5-tris(3,5-dicyclohexyl-4-hydroxybenzyl)isocyanurate.

Benzylphosphonates, such as, for example, dimethyl 2,5-di(tert-butyl)-4-hydroxybenzylphosphonate, diethyl 3,5-di(tert-butyl)-4-hydroxybenzylphosphonate ((3,5-bis(1,1-dimethylethyl)-4-hydroxyphenyl)methylphosphonic acid diethyl ester), dioctadecyl 3,5-di(tert-butyl)-4-hydroxybenzylphosphonate, dioctadecyl 5-(tert-butyl)-4-hydroxy-3-methylbenzylphosphonate and calcium salt of 3,5-di(tert-butyl)-4-hydroxybenzylphosphonic acid monoethyl ester.

Acylaminophenols, such as, for example, lauric acid 4-hydroxyanilide, stearic acid 4-hydroxyanilide, 2,4-bisoctylmercapto-6-(3,5-(tert-butyl)-4-hydroxyanilino)-s-triazine and octyl N-(3,5-di(tert-butyl)-4-hydroxyphenyl)carbamate.

Esters of β-(3,5-di(tert-butyl)-4-hydroxyphenyl)propionic acid with mono- or polyvalent alcohols, such as, e.g., with methanol, ethanol, n-octanol, isooctanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxalic acid diamide, 3-thiaundecanol, 3-thiapentadecanol, trimethylhexanediol, trimethylolpropane and 4-hydroxymethyl-1-phospha-2,6,7-trioxabicyclo[2.2.2]octane.

Esters of β-(5-(tert-butyl)-4-hydroxy-3-methylphenyl)propionic acid with mono- or polyvalent alcohols, such as, e.g., with methanol, ethanol, n-octanol, isooctanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxalic acid diamide, 3-thiaundecanol, 3-thiapentadecanol, trimethylhexanediol, trimethylolpropane and 4-hydroxymethyl-1-phospha-2,6,7-trioxabicyclo[2.2.2]octane.

Esters of β-(3,5-dicyclohexyl-4-hydroxyphenyl)propionic acid with mono- or polyvalent alcohols, such as, e.g., with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxalic acid diamide, 3-thiaundecanol, 3-thiapentadecanol, trimethylhexanediol, trimethylolpropane and 4-hydroxymethyl-1-phospha-2,6,7-trioxabicyclo[2.2.2]octane.

Esters of 3,5-di(tert-butyl)-4-hydroxyphenylacetic acid with mono- or polyvalent alcohols, such as, e.g., with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxalic acid diamide, 3-thiaundecanol, 3-thiapentadecanol, trimethylhexanediol, trimethylolpropane and 4-hydroxymethyl-1-phospha-2,6,7-trioxabicyclo[2.2.2]octane.

Amides of β-(3,5-di(tert-butyl)-4-hydroxyphenyl)propionic acid, such as, e.g., N,N'-bis(3,5-di(tert-butyl)-4-hydroxyphenylpropionyl)hexamethylenediamine, N,N'-bis(3,5-di(tert-butyl)-4-hydroxyphenylpropionyl) trimethylenediamine, N,N'-bis(3,5-di(tert-butyl)-4-hydroxyphenylpropionyl)hydrazine and N,N'-bis[2-(3-[3,5-di(tert-butyl)-4-hydroxyphenyl]propionyloxy)ethyl]oxamide (e.g. Naugard®XL-1 from Uniroyal).

Ascorbic acid (vitamin C).

Aminic antioxidants, such as, for example, N,N'-diisopropyl-p-phenylenediamine, N,N'-di(secbutyl)-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-tolylsulfamoyl)diphenylamine, N,N'-dimethyl-N,N'-di(secbutyl)-p-phenylenediamine, diphenylamine, N-allyldiphenylamine, 4-isopropoxydiphenylamine, N-phenyl-1-naphthylamine, N-(4-(tert-octyl)phenyl)-1-naphthylamine, N-phenyl-2-naphthylamine, octylated diphenylamine, for example p,p'-di(tert-octyl)diphenylamine, 4-(n-butylamino)phenol, 4-butyrylaminophenol, 4-nonanoylaminophenol, 4-dodecanoylaminophenol, 4-octadecanoylaminophenol, bis(4-methoxyphenyl)amine, 2,6-di(tert-butyl)-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, mixture of mono- and dialkylated tert-butyl/tert-octyldiphenylamines, mixture of mono- and dialkylated nonyldiphenylamines, mixture of mono- and dialkylated dodecyldiphenylamines, mixture of mono- and dialkylated isopropyl/isohexyldiphenylamines, mixture of mono- and dialkylated tert-butyldiphenylamines, 2,3-dihydro-3,3-dimethyl-4H-1,4-benzothiazine, phenothiazine, mixture of mono- and dialkylated tert-butyl/tert-octylphenothiazines, mixture of mono- and dialkylated tert-octylphenothiazines, N-allylphenothiazine, N,N,N',N'-tetraphenyl-1,4-diaminobut-2-ene, N,N-bis(2,2,6,6-tetramethylpiperidin-4-yl)hexamethylenediamine, bis(2,2,6,6-tetramethylpiperidin-4-yl)sebacate, 2,2,6,6-tetramethylpiperidin-4-one, 2,2,6,6-tetramethylpiperidin-4-ol, the dimethyl succinate polymer with 4-hydroxy-2,2,6,6-tetramethyl-1-piperidinethanol [CAS number 65447-77-0] (for example Tinuvin® 622 from Ciba Specialty Chemicals Inc.) and the polymer of 2,2,4,4-tetramethyl-7-oxa-3,20-diazadispiro[5.1.11.2]henicosan-21-one and epichlorhydrin [CAS-No.: 202483-55-4] (for example Hostavin® 30 from Ciba Specialty Chemicals Inc.).

Preferred antioxidants are alkylated monophenols, hydroquinones and alkylated hydroquinones, tocopherol and its derivatives, chromanol and its derivatives, ascorbic acid, and Irganox 1010.

The antioxidants are used as a solid or liquid material, a solution or in the form of aqueous dispersions, preferably as an additive, which is soluble or dispersible in the film-forming polymer dispersion or film-forming polymer solution. Solids are typically jetted into the apparatus as fine dusts by means of a carrier gas. The dispersion is preferably applied by means of a high-speed stirrer by preparing the dispersion from solid material and water in a first step and introducing it in a second step rapidly into the fluidized bed preferably via a nozzle. The liquid or the solution is preferably applied by means of a nozzle.

The antioxidant can preferably be applied together with the polyurethane (or other film-forming polymer) or as a separate dispersion via separate nozzles at the same time as the polyurethane or at different times from the polyurethane.

In a particular preferred embodiment, especially with polyurethanes, the antioxidant is added already during, before or after synthesis of the film-forming polymer dispersion or film-forming polymer solution to it.

In a preferred embodiment, the antioxidant is used in an amount in the range from 0 to 6.0% to % by weight, preferably less than 3% by weight, especially in the range from 0.1% to 2.5% by weight and most preferably from 1.0 to 1.5% by weight, based on the weight of the film-forming polymer.

In another embodiment of this invention a coalescing agent is added in the spray-coating step a).

Coalescing agents are preferably at least partially water-soluble organic solvents. Water soluble means that the coalescing agent is fully miscible with water or is miscible to at least 10 wt. %, preferably to at least 25 wt. % with water at 25 C and 1 bar ambient pressure. Any organic solvent that is accelerating the formation of a film when admixed to the aqueous film-forming polymer dispersion or solution after this dispersion or solution is coated onto the water-absorbing polymeric particles is suitable to function as coalescing agent. In one preferred embodiment an aqueous polymer dispersion is spray-coated in step a).

The coalescing agents include but are not limited to alcohols such as methanol, ethanol, n-propanol, isopropanol, n-butanol, tert-butanol, sec-butanol, ethylene glycol, 1,2-propanediol, 1,3-propanediol, ethylene carbonate, propylene carbonate, glycerol, 2-methyl-2,4-pentane diol, Propylene glycole butyl ether, di(ethylene glycole)butyl ether, 3-methoxy-1-butyl acetate and methoxyethanol and water-soluble ethers such as tetrahydrofuran and dioxane. The coalescing agent may or may not evaporate during the subsequent heat treatment step after coating.

The coalescing agents are used as liquid material, which can be blended into or dissolved in the aqueous film forming polymer dispersion or solution.

The coalescing agent can preferably be applied together with the polyurethane (or other film-forming polymer) and/or the antioxidant or as a separate solution via separate nozzles at the same time as the film-forming polymer or at different times from the film-forming polymer.

In a preferred embodiment, the coalescing agent is used in an amount in the range from 0 to 10% to % by weight, preferably less than 8% by weight, especially in the range from 0.1 to 6% by weight, more preferably in the range from 0.5% to 4% by weight and most preferably in the range form 1.0 to 3.0% by weight, based on the weight of the film-forming polymer.

In a preferred embodiment, a coalescing agent is added in step a) and an antioxidant is added in step a) and/or b). In a preferred embodiment, a coalescing agent and an antioxidant are added in step a).

In another embodiment at least one agent, which is able to cross-link polyurethanes in a heat treatment as in step b), for example—but not limited to—isocyanates or carbodiimides is added in step a). In a preferred embodiment a coalescing agent, an antioxidant and a cross-linker for polyurethanes are added in step a).

In a preferred embodiment, a deagglomerating aid is added before the heat-treatment step to the particles to be coated or preferably which have already been coated. A deagglomerating aid would be known by those skilled in the art to be for example a finely divided water-insoluble salt selected from organic and inorganic salts and mixtures thereof, and also waxes and surfactants. A water-insoluble salt refers herein to a salt which at a pH of 7 has a solubility in water of less than 5 g/l, preferably less than 3 g/l, especially less than 2 g/l and most preferably less than 1 g/l (at 25° C. and 1 bar). The use of a water-insoluble salt can reduce the tackiness due to the film-forming polymer, especially the polyurethane, which especially appears in the course of heat-treatment.

The water-insoluble salts are used as a solid material or in the form of dispersions, preferably as an aqueous dispersion. Solids are typically jetted into the apparatus as fine dusts by means of a carrier gas. The dispersion is preferably applied by means of a high speed stirrer by preparing the dispersion from solid material and water in a first step and introducing it in a second step rapidly into the fluidized bed preferably via a nozzle. Preferably both steps are carried out in the same apparatus. The aqueous dispersion can if appropriate be applied together with the polyurethane (or other film-forming polymer) or as a separate dispersion via separate nozzles at the same time as the polyurethane or at different times from the polyurethane. It is particularly preferable to apply the deagglomerating aid after the film-forming polymer has been applied and before the subsequent heat-treatment step. Optionally, the addition may be repeated after the heat-treatment step.

Suitable cations in the water-insoluble salt are for example $Ca^{2+}$, $Mg^{2+}$, $Sr^{2+}$, $Ba^{2+}$, $Al^{3+}$, $Sc^{3+}$, $Y^{3+}$, $Ln^{3+}$ (where Ln denotes lanthanoids), $Ti^{4+}$, $Zr^{4+}$, $Li^+$, $K^+$, $Na^+$ or $Zn^{2+}$. Suitable inorganic anionic counterions are for example carbonate, sulfate, bicarbonate, orthophosphate, silicate, oxide or hydroxide. When a salt occurs in various crystal forms, all crystal forms of the salt shall be included. The water-insoluble inorganic salts are preferably selected from calcium sulfate, calcium carbonate, calcium phosphate, calcium silicate, calcium fluoride, apatite, magnesium phosphate, magnesiumhydroxide, magnesium oxide, magnesium carbonate, dolomite, lithium carbonate, lithium phosphate, strontium carbonate, strontium sulfate, barium sulfate, zinc oxide, zinc phosphate, oxides, hydroxides, carbonates and phosphates of the lanthanoids, sodium lanthanoid sulfate, scandium sulfate, yttrium sulfate, lanthanum sulfate, scandium hydroxide, scandium oxide, aluminum oxide, hydrated aluminum oxide and mixtures thereof. Apatite refers to fluoroapatite, hydroxyl apatite, chloroapatite, carbonate apatite and carbonate fluoroapatite. Of particular suitability are calcium and magnesium salts such as calcium carbonate, calcium phosphate, magnesium carbonate, calcium oxide, magnesium oxide, calcium sulfate and mixtures thereof. Amorphous or crystalline forms of aluminum oxide, titanium dioxide and silicon dioxide are also suitable. Mixed metal oxides comprising at least one of the foregoing metal cations and optionally any other metal cation and exhibiting Perowskit- or Spinell-type structure are suitable provided they exhibit white or yellow color as powders. These deagglomerating aids can also be used in their hydrated forms. Useful deagglomerating aids further include many clays, talcum and zeolites. Silicon dioxide is preferably used in its amorphous form, for example as hydrophilic or hydrophobic Aerosil® as fumed silicas, which have particle sizes in the range 5-75 nm. Selectively can also be used water-soluble forms as commercially available aqueous silica sol, such as for example Levasil® Kieselsole (H.C. Starck GmbH), which have particle sizes in the range 5-75 nm.

The average primary particle size of the finely divided water-insoluble salt is typically less than 200 μm, preferably less than 100 μm, especially less than 50 μm, more preferably less than 20 μm, even more preferably less than 10 μm and most preferably in the range of less than 5 μm. Fumed silicas are often used as even finer particles, e.g. less than 50 nm, preferably less than 30 nm, even more preferably less than 20 nm primary particle size.

In a preferred embodiment, the finely divided water-insoluble salt is used in an amount in the range from 0.001% to 20% by weight, preferably less than 10% by weight, especially in the range from 0.001% to 5% by weight, more preferably in the range from 0.001% to 2% by weight and most preferably between 0.001 and 1% by weight, based on the weight of the water-absorbing polymeric particles.

In lieu of or in addition to the above inorganic salts it is also possible to use other known deagglomerating aids, examples being waxes and preferably micronized or preferably partially oxidized polyethylenic waxes, which can likewise be used in the form of an aqueous dispersion. Such waxes are described in EP 0 755 964, which is hereby expressly incorporated herein by reference.

Furthermore, to achieve deagglomeration, a second coating with a dispersion or solution of another polymer of high Tg (>50° C.) can be carried out.

Useful deagglomerating aids further include stearic acid, stearates—for example: magnesium stearate, calcium stearate, zinc stearate, aluminum stearate, and furthermore polyoxyethylene-20-sorbitan monolaurate and also polyethylene glycol 400 monostearate.

Useful deagglomerating aids likewise include surfactants. A surfactant can be used alone or mixed with one of the abovementioned deagglomerating aids, preferably a water-insoluble salt.

The addition can take place together with the film-forming polymer, before the addition of the film-forming polymer or after the addition of the film-forming polymer. In general, it can preferably be added before heat-treatment. The surfactant can further be applied during the post-crosslinking operation.

In a preferred embodiment a deagglomerating aid, preferably at least two different deagglomerating aids, is added in step a) and after step b).

In another embodiment a deagglomerating aid is added only after step b)

Useful surfactants include nonionic, anionic and cationic surfactants and also mixtures thereof. The water-absorbing material preferably comprises nonionic surfactants. Useful nonionic surfactants include for example sorbitan esters, such as the mono-, di- or triesters of sorbitans with $C_8$-$C_{18}$-carboxylic acids such as lauric, palmitic, stearic and oleic acids; polysorbates; alkylpolyglucosides having 8 to 22 and preferably 10 to 18 carbon atoms in the alkyl chain and 1 to 20 and preferably 1.1 to 5 glucoside units; N-alkylglucamides; alkylamine alkoxylates or alkylamide ethoxylates; alkoxylated $C_8$-$C_{22}$-alcohols such as fatty alcohol alkoxylates or oxo alcohol alkoxylates; block polymers of ethylene oxide, propylene oxide and/or butylene oxide; alkylphenol ethoxylates having $C_6$-$C_{14}$-alkyl chains and 5 to 30 mol of ethylene oxide units.

The amount of surfactant is generally in the range from 0.01% to 0.5% by weight, preferably less than 0.1% by weight and especially below 0.05% by weight, based on the weight of the water-absorbing material.

The heat-treatment takes place at temperatures above 50° C., preferably in a temperature range from 100 to 200° C., especially 120-180° C. Without wishing to be bound by theory, the heat-treatment causes the applied film-forming polymer, preferably polyurethane, to flow and form a polymeric film whereby the polymer chains are entangled. The duration of the heat-treatment is dependent on the heat-treatment temperature chosen and the glass transition and melting temperatures of the film-forming polymer. In general, a heat-treatment time in the range from 30 minutes to 120 minutes will be found to be sufficient. However, the desired formation of the polymeric film can also be achieved when heat-treatment for less than 30 minutes, for example in a fluidized bed dryer. Longer times are possible, of course, but especially at higher temperatures can lead to damage in the polymeric film or to the water-absorbing material.

It has been found that the water-absorbing material's performance can be optimized and the time needed for heat-treatment at a given temperature can be minimized if samples are taken from the coated water-absorbing material at specific pre-determined residence times from the heat-treatment dryer. In the beginning of the heat-treatment the CS-SFC values of the product increase steadily but then decrease or stay flat at a certain level after a while. It is therefore one embodiment of the present invention that in step b) the duration of the heat-treatment is chosen that the CS-SFC value of the obtained polymeric particles is at least 10%, preferably at least 30%, especially at least 50%, even more preferred at least 80% and most preferred 95% of the optimum CS-SFC value. It has also surprisingly been found that the optimum time for heat-treatment is further affected by addition of coalescing agents and/or anti-oxidative agents. The presence of cross-linkers for polyurethanes may also effect the optimum time.

The optimum CS-SFC-values are easily determined by treating a batch of coated water-absorbing polymeric particles at a given product temperature which is kept constant while agitating and periodic extraction of small samples from that batch. By determination of the water-absorbent material properties from these samples and tabulating or plotting the performance data versus residence time it is possible to determine the optimum heat treatment time period in the specific apparatus used. In general a performance optimum/maximum is observed. Product samples are typically taken after pre-determined residence time periods, for example every 5-10 minutes. A person skilled in the art will typically take about 5 or more samples from the beginning of the heat-treatment until the residence time is reached after which at least two subsequent samples from this sample collective exhibiting flat or decreasing CS-SFC data have been obtained. To determine the optimum conditions one has to take a sufficient number of product samples to obtain CS-SFC and other respective absorbency data for these samples. The data is then plotted versus residence time and the optimum residence time can be determined graphically. Alternatively a person skilled in the art will use fit-algorithms to determine the optimum residence time. Furthermore this process is preferably repeated for different heat-treatment temperatures in order to optimize also for heat-treatment product temperature. Optimum CS-SFC is maximum CS-SFC. However, for the production of certain water-absorbent materials it may be desirable to determine the residence time required to obtain just a desired fraction of that optimum CS-SFC while at the same time maximizing its CCRC or other relevant performance properties, which can be accomplished using the same procedure as described above by plotting or evaluating both or all of these parameters versus residence time. A person skilled in the art will also account for equipment specific effects like a heat-up curve when following the procedure above.

In one embodiment herein the water-absorbing material herein may be obtainable by process comprises the steps of
a) spray-coating water-absorbing polymeric particles with an elastic film-forming polymer in a fluidized bed reactor in the range from 0° C. to 150° C. and
b) heat-treatment of the coated particles at a temperature above 50° C.,
wherein in step a) and/or step b) an antioxidant or in step b) a coalescing agent is added and wherein step b) the duration of the heat-treatment is chosen that the CS-SFC value of the obtained polymeric particles is at least 10% of the optimum CS-SFC value; or by a process comprises the steps of
a) spray-coating water-absorbing polymeric particles with an elastic film-forming polymer in a fluidized bed reactor in the range from 0° C. to 150° C. and b) heat-treatment of the coated particles at a temperature above 50° C., wherein in step a) an antioxidant and a coalescing agent is added and wherein step b) the duration of the heat-treatment is chosen that the CS-SFC value of the obtained polymeric particles is at least 10% of the optimum CS-SFC value. Optionally a cross-linker for polyurethanes may be added in step a).

The heat-treatment is carried out for example in a fluidized bed dryer, a tunnel dryer, a tray dryer, a tower dryer, one or more heated screws or a disk dryer or a Nara® dryer. The heat-treatment can take place on trays in forced air ovens. In this case it is desirable to treat the coated polymer with a deagglomerating aid before heat-treatment. Alternatively, the tray can be anti-stick coated and the coated polymer then placed on the tray as a monoparticulate layer in order that sintering together may be avoided.

Heat-treatment is preferably done in a fluidized bed reactor and more preferably in a continuous fluidized bed reactor especially directly in the Wurster Coater. It is particularly preferable that the coating step a) and the heat-treatment step b) be carried out in a fluidized bed reactor, very particularly preferable in a continuous fluidized bed reactor.

For the process steps of coating, heat-treatment, and cooling, it may be possible to use an inert gas but in general this is not necessary. According to the invention it is possible to use air, dehumidified air or dried air in each of these steps or mixtures of air and inert gas in one or more of these process steps. In a preferred embodiment the oxygen content of the gas stream in the heat-treatment step is less than 8 Vol % preferably less than 1 Vol %.

It is believed that the water-absorbing material obtained by the process according to the present invention is surrounded by a homogeneous film. Without wishing to be bound by theory the encapsulation morphology is not particular critical as long as the shell is maintained during and after swelling and as long as the physical forces developed during swelling are almost evenly distributed across the swelling water-absorbing particle by the polymer film on the particle surface. Depending on the coating rate and amount of polymer applied based on the absorbent polymeric particles and the way the application is carried out, the polymeric film may conceivably not be completely uninterrupted, but have uncovered areas, such as islands. This embodiment too is encompassed by the invention. A flawed, for example a coating with holes is not disadvantageous as long as the particles of the superabsorbent polymer are coated such that despite the flaws in the coating, substantially similar mechanical forces occur in the swelling of the coated water-absorbing polymeric particles as in the case of a substantially flawless coating. The hydrophilicity of the polymer plays a minor part for this embodiment. The deliberate incorporation of such imperfections e.g. via the use of fillers or polymeric additives to the dispersion may provide a means to increase the absorption speed of the claimed materials, and may be used as an advantage. It may be advantageous to include water soluble fillers in the coating that subsequently dissolve during the swelling of the coated water-absorbing material. In one embodiment the film-forming polymer is forming a partially perforated film on the surface of virtually all coated water-absorbing polymeric particles.

The even distribution of physical forces can be made visible by microscopic observation of the swelling water-absorbing material. The individual particles tend to exhibit rounded or spherical shapes even when they are produced from very irregular water-absorbing polymeric particles. Without wishing to be bound by theory it is preferable that most or all water-absorbing polymeric particles of a given batch are uniformly coated. It may also be possible to use such water-absorbing material mixed with other granular non-coated superabsorbent polymers in any ratio.

It is generally observed that flawless and flawed particles exist side by side, and this can be microscopically visualized by staining methods.

It may be advantageous in such cases that the absorbent polymeric particle is post-crosslinked, as detailed above. Already post-crosslinked water-absorbing polymeric particles can be coated with the film-forming polymer especially polyurethane. It is likewise possible for the post-crosslinker not to be applied until before heat-treatment, i.e., preferably concurrently with the film-forming polymer especially polyurethane in the fluidized bed or after the film-forming polymer-coating step. In the latter version of the process, this can be accomplished for example concurrently with the preferred addition of the deagglomerating aid. In all cases, heat-treatment is carried out at temperatures in the range from 50 to 200° C., and most preferably carried out at temperatures in the range from 120 to 180° C.

It has been found out, that in some cases the powder flow and compacting properties of the water absorbing particles coated with elastic film forming polymers deteriote after heat treatment as in step b). They tend to stick and agglomerate in the warm state as well as after cooling down to ambient temperature and storage over long time under weight pressure as for example in a big bag. The tackiness can be reduced or eliminated and the flowability (i.e. flow rate) can be significantly improved by applying a deagglomeration aid in a final process step onto the already coated and heat-treated water absorbing particles. In a preferred embodiment the deagglomeration aid is jetted as dispersion onto the hot water absorbing particles in a fluidized bed. The benefit of this is the partially cooling of the coated particles and therefore saving time and energy for cooling down the whole mass to a temperature which allows discharging into big bags. Such deagglomeration aid is used for this purpose in an amount of 0.001-10 weight-%, preferably 0.01-5 weight-%, more preferably 0.05-1.0 weight-%, and most preferably 0.5-0.8 weight-%. Typical deagglomeration aids are described above.

After the heat-treatment step has been concluded, the dried water-absorbing polymeric materials are cooled. To this end, the warm and dry polymer is preferably continuously transferred into a downstream cooler. This can be for example a disk cooler, a Nara paddle cooler or a screw cooler. Cooling is via the walls and if appropriate the stirring elements of the cooler, through which a suitable cooling medium such as for example warm or cold water flows. Water or aqueous solutions or dispersions of additives may preferably be sprayed on in the cooler; this increases the efficiency of cooling (partial evaporation of water) and the residual moisture content in the finished product can be adjusted to a value in the range from 0% to 15% by weight, preferably in the range from 0.01% to 6% by weight and more preferably in the range from 0.1% to 3% by weight. The increased residual moisture content reduces the dust content of the product and helps to accelerate the swelling when such water-absorbing material is contacted with aqueous liquids. Examples for additives are triethanolamine, surfactants, silica, or aluminum-sulfate.

Optionally, however, it is possible to use the cooler for cooling only and to carry out the addition of water and additives in a downstream separate mixer. Cooling lowers the product temperature only to such an extent that the product can easily be packed in plastic bags or within silo trucks. Product temperature after cooling is typically less than 90°

C., preferably less than 60° C., most preferably less than 40° C. and preferably more than −20° C.

It may be preferable to use a fluidized bed cooler.

If coating and heat-treatment are both carried out in fluidized beds, the two operations can be carried out either in separate apparatus or in one apparatus having communicating chambers. If cooling too is to be carried out in a fluidized bed cooler, it can be carried out in a separate apparatus or optionally combined with the other two steps in just one apparatus having a third reaction chamber. More reaction chambers are possible as it may be desired to carry out certain steps like the coating step in multiple chambers consecutively linked to each other, so that the water absorbing polymer particles consecutively build the film-forming polymer shell in each chamber by successively passing the particles through each chamber one after another.

The process described herein is notable for the fact that it produces water absorbing polymeric particles with excellent absorbing properties in a good time-space yield. It further makes it possible to work in a gas stream containing oxygen particularly when at least one anti-oxidative agent is used.

The water-swellable material received according to the invention preferably comprises less than 20% by weight of water, or even less than 10% or even less than 8% or even less than 5%, or even no water. The water content of the water-swellable material can be determined by the EDANA test, number ERT 430.1-99 (February 1999) which involves drying the water-swellable material at 105° Celsius for 3 hours and determining the moisture content by the weight loss of the water-swellable materials after drying.

It is possible that the water-swellable material comprises two or more layers of coating agent (shells), obtainable by coating the water-swellable polymers twice or more. This may be the same coating agent or a different coating agent. However, preference for economic reasons is given to a single coating with a film-forming polymer and preferably with a polyurethane.

The water-absorbing material received according to the present invention is notable for the fact that the particles, which have an irregular shape when dry, assume in the swollen state a more rounded shape/morphology, since the forces onto the swelling absorbent core are distributed via the rebound forces of the elastic polymeric envelope over the surface and the elastic polymeric envelope substantially retains its morphological properties in this respect during the swelling process and in use. The enveloping film-forming polymer especially the polyurethane is permeable to saline, so that the polymer particles achieve excellent absorption values in the CS-CRC (Core Shell Centrifuge Retention Capacity) and in the CCRC (Cylinder centrifuge retention capacity) test and also good permeability in the CS-SFC test.

Preference is given to a water-absorbing material whose Core Shell Centrifuge Retention Capacity (CS-CRC) value is not less than 20 g/g, preferably not less than 25 g/g achieved by a process according to this invention.

Preference is likewise given to a water-absorbing material where CS-CRC and CS-SFC (Core Shell Saline Flow Capacity) satisfies the following relation: Log (CS-SFC'/150)>3.36−0.133×CS-CRC, where CS-SFC'=CS-SFC×$10^7$ and the dimension of 150 is [$cm^3$ s/g] achieved by a process according to this invention.

Preference is likewise given to a water-absorbing material where CS-CRC and CS-SFC (Core Shell Saline Flow Capacity) satisfies the following relation: Log (CS-SFC'/150)>2.5−0.095×CS-CRC, where CS-SFC'=CS-SFC×$10^7$ and the dimension of 150 is [$cm^3$ s/g] achieved by a process according to this invention.

Preference is given to a water-absorbing material whose Cylinder Centrifuge Retention Capacity (CCRC) value is not less than 20 g/g, preferably not less than 25 g/g, achieved by a process according to this invention.

Preference is likewise given to a water-absorbing material where CCRC and CS-SFC (Core Shell Saline Flow Capacity) satisfies the following relation: Log (CS-SFC'/150)>3.36−0.133×CCRC, where CS-SFC'=CS-SFC×$10^7$ and the dimension of 150 is [$cm^3$ s/g] achieved by a process according to this invention.

Preference is likewise given to a water-absorbing material where CCRC and CS-SFC (Core Shell Saline Flow Capacity) satisfies the following relation: Log (CS-SFC'/150)>2.5−0.095×CCRC, where CS-SFC'=CS-SFC×$10^7$ and the dimension of 150 is [$cm^3$ s/g] achieved by a process according to this invention.

Preferred may be in one embodiment that the resulting water-absorbing materials have a CS-SFC of at least 350×$10^{-7}$ $cm^3$ s/g, or preferably at least 400×$10^{-7}$ $cm^3$ s/g or even at least 450×$10^{-7}$ $cm^3$ s/g. In another embodiment, it may even be preferred that the resulting water-absorbing material herein has a CS-SFC of at least 540×$10^{-7}$ $cm^3$ s/g, or even preferably at least 600×$10^{-7}$ $cm^3$ s/g.

In addition, the water-absorbing materials made by the process of the invention have a high wet porosity (i.e. this means that once an amount of the water-swellable material of the invention is allowed to absorb a liquid and swell, it will typically form a (hydro)gel or (hydro)gel bed, which has a certain wet porosity, in particular compared to the uncoated water-absorbing polymeric particles, as can be measured with the PHL test disclosed in U.S. Pat. No. 5,562,646 which is incorporated herein by reference; if the water-absorbing material and water-absorbing polymeric particles are to be tested at different pressures than described in the test method, the weight used in this test should be adjusted accordingly.

In addition, the water-absorbing materials made by the process of the invention have a high permeability for liquid flow through the gel bed as can be measured with the CS-SFC test set out herein.

The water-absorbing material, hereinafter also referred to as hydrogel-forming polymer, was tested by the test methods described hereinbelow.

Methods:

The measurements should be carried out, unless otherwise stated, at an ambient temperature of 23±2° C. and a relative humidity of 50±10%. The water-absorbing polymeric particles are thoroughly mixed through before measurement. For the purpose of the following methods AGM means "Absorbent Gelling Material" and can relate to the water absorbing polymer particles as well as to the water-absorbing material. The respective meaning is clearly defined by the data given in the examples below.

CRC (Centrifuge Retention Capacity)

This method determines the free swellability of the hydrogel in a teabag. To determine CRC, 0.2000+/−0.0050 g of dried hydrogel (particle size fraction 106-850 μm or as specifically indicated in the examples which follow) is weighed into a teabag 60×85 mm in size, which is subsequently sealed shut. The teabag is placed for 30 minutes in an excess of 0.9% by weight sodium chloride solution (at least 0.83 l of sodium chloride solution/1 g of polymer powder). The teabag is subsequently centrifuged at 250 g for 3 minutes. The amount of liquid is determined by weighing the centrifuged teabag. The procedure corresponds to that of EDANA recommended test method No. 441.2-02 (EDANA=European Disposables and Nonwovens Association). The teabag material and also the centrifuge and the evaluation are likewise defined therein.

CS-CRC (Core Shell Centrifuge Retention Capacity)

CS-CRC is carried out completely analogously to CRC, except that the sample's swelling time is extended from 30 min to 240 min.

The CCRC-Method is Described Herein Below.

AUL (Absorbency Under Load 0.7 Psi)

Absorbency Under Load is determined similarly to the absorption under pressure test method No. 442.2-02 recommended by EDANA (European Disposables and Nonwovens Association), except that for each example the actual sample having the particle size distribution reported in the example is measured.

The measuring cell for determining AUL 0.7 psi is a Plexiglas cylinder 60 mm in internal diameter and 50 mm in height. Adhesively attached to its underside is a stainless steel sieve bottom having a mesh size of 36 μm. The measuring cell further includes a plastic plate having a diameter of 59 mm and a weight, which can be placed in the measuring cell together with the plastic plate. The plastic plate and the weight together weigh 1345 g. AUL 0.7 psi is determined by determining the weight of the empty Plexiglas cylinder and of the plastic plate and recording it as $W_0$. Then 0.900+/−0.005 g of hydrogel-forming polymer (particle size distribution 150-800 μm or as specifically reported in the examples which follow) is weighed into the Plexiglas cylinder and distributed very uniformly over the stainless steel sieve bottom. The plastic plate is then carefully placed in the Plexiglas cylinder, the entire unit is weighed and the weight is recorded as $W_a$. The weight is then placed on the plastic plate in the Plexiglas cylinder. A ceramic filter plate 120 mm in diameter, 10 mm in height and 0 in porosity (Duran, from Schott) is then placed in the middle of the Petri dish 200 mm in diameter and 30 mm in height and sufficient 0.9% by weight sodium chloride solution is introduced for the surface of the liquid to be level with the filter plate surface without the surface of the filter plate being wetted. A round filter paper 90 mm in diameter and <20 μm in pore size (S&S 589 Schwarzband from Schleicher & Schüll) is subsequently placed on the ceramic plate. The Plexiglas cylinder holding hydrogel-forming polymer is then placed with the plastic plate and weight on top of the filter paper and left there for 60 minutes. At the end of this period, the complete unit is taken out of the Petri dish from the filter paper and then the weight is removed from the Plexiglas cylinder. The Plexiglas cylinder holding swollen hydrogel is weighed out together with the plastic plate and the weight is recorded as $W_b$.

Absorbency under load (AUL) is calculated as follows:

$$\text{AUL } 0.7 \text{ psi } [g/g] = [W_b - W_a] / [W_a - W_0]$$

AUL 0.3 psi and 0.5 psi are measured similarly at the appropriate lower pressure.

CS-AUL (Core Shell Absorption Under Load 0.7 Psi)

The measuring cell for determining CS-AUL 0.7 psi is a Plexiglas cylinder 60 mm in internal diameter and 50 mm in height. Adhesively attached to its underside is a stainless steel sieve bottom having a mesh size of 36 μm (Steel 1.4401, wire diameter 0.028 mm, from Weisse & Eschrich). The measuring cell further includes a plastic plate having a diameter of 59 mm and a weight which can be placed in the measuring cell together with the plastic plate. The weight of the plastic plate and the weight together weigh 1345 g. AUL 0.7 psi is determined by determining the weight of the empty Plexiglas cylinder and of the plastic plate and recording it as $W_0$. Then 0.900+/−0.005 g of hydrogel-forming polymer (particle size distribution 150-800 μm or as specifically reported in the example which follows) is weighed into the Plexiglas cylinder and distributed very uniformly over the stainless steel sieve bottom. The plastic plate is then carefully placed in the Plexiglas cylinder, the entire unit is weighed and the weight is recorded as $W_a$. The weight is then placed on the plastic plate in the Plexiglas cylinder. A round filter paper with a diameter of 90 mm (No. 597 from Schleicher & Schüll) is placed in the center of a 500 ml crystallizing dish (from Schott) 115 mm in diameter and 65 mm in height. 200 ml of 0.9% by weight sodium chloride solution are then introduced and the Plexiglas cylinder holding hydrogel-forming polymer is then placed with the plastic plate and weight on top of the filter paper and left there for 240 minutes. At the end of this period, the complete unit is taken out of the Petri dish from the filter paper and adherent liquid is drained off for 5 seconds. Then the weight is removed from the Plexiglas cylinder. The Plexiglas cylinder holding swollen hydrogel is weighed out together with the plastic plate and the weight is recorded as $W_b$.

Absorbency under load (AUL) is calculated as follows:

$$\text{AUL } 0.7 \text{ psi } [g/g] = [W_b - W_a] / [W_a - W_0]$$

AUL 0.3 psi and 0.5 psi are measured similarly at the appropriate lower pressure.

Saline Flow Conductivity (SFC)

The method to determine the permeability of a swollen gel layer is the "Saline Flow Conductivity" also known as "Gel Layer Permeability" and is described in EP A 640 330. The equipment used for this method has been modified as described below.

FIG. 1 shows the permeability measurement equipment set-up with the open-ended tube for air admittance A, stoppered vent for refilling B, constant hydrostatic head reservoir C, Lab Jack D, delivery tube E, stopcock F, ring stand support G, receiving vessel H, balance I and the SFC apparatus L.

Figure 2:
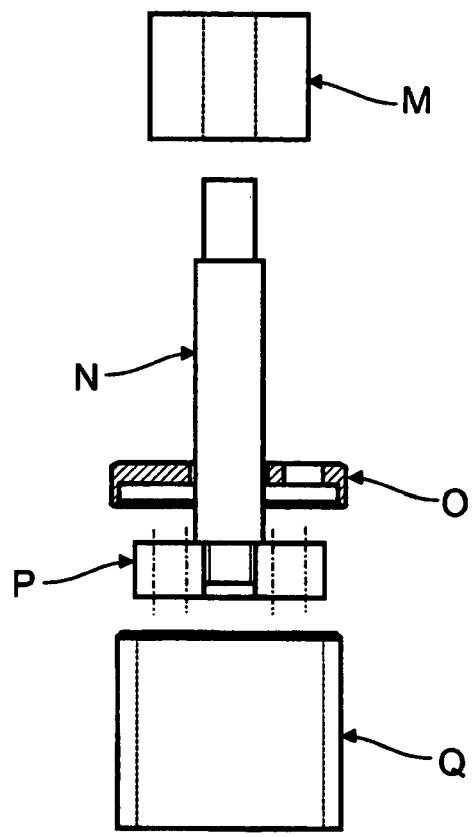
FIG. 2 is a detailed view of the SFC cylinder/plunger apparatus.

FIG. 2 shows the SFC apparatus L consisting of the metal weight M, the plunger shaft N, the lid O, the center plunger P and the cylinder Q.

The cylinder Q has an inner diameter of 6.00 cm (area=28.27 cm$^2$). The bottom of the cylinder Q is faced with a stainless-steel screen cloth (mesh width: 0.036 mm; wire diameter: 0.028 mm) that is bi-axially stretched to tautness prior to attachment. The plunger consists of a plunger shaft N of 21.15 mm diameter. The upper 26.0 mm having a diameter of 15.8 mm, forming a collar, a perforated center plunger P which is also screened with a stretched stainless-steel screen (mesh width: 0.036 mm; wire diameter: 0.028 mm), and annular stainless steel weights M. The annular stainless steel weights M have a center bore so they can slip on to plunger shaft and rest on the collar. The combined weight of the center plunger P, shaft and stainless-steel weights M must be 596 g (±6 g), which corresponds to 0.30 PSI over the area of the cylinder. The cylinder lid O has an opening in the center for vertically aligning the plunger shaft N and a second opening near the edge for introducing fluid from the reservoir into the cylinder Q.

Figure 3:
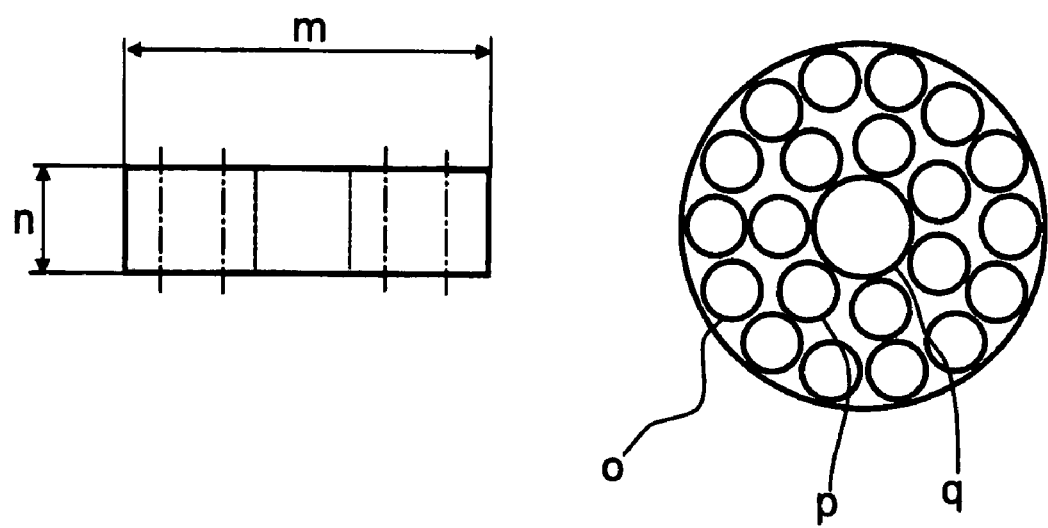
FIG. 3 is a view of the SFC plunger details.

The cylinder Q specification details are:
Outer diameter of the Cylinder: 70.35 mm
Inner diameter of the Cylinder: 60.0 mm
Height of the Cylinder: 60.5 mm
The cylinder lid O specification details are:
Outer diameter of SFC Lid: 76.05 mm
Inner diameter of SFC Lid: 70.5 mm
Total outer height of SFC Lid: 12.7 mm
Height of SFC Lid without collar: 6.35 mm
Diameter of hole for Plunger shaft positioned in the center: 22.25 mm
Diameter of hole in SFC lid: 12.7 mm
Distance centers of above mentioned two holes: 23.5 mm The metal weight M specification details are:
Diameter of Plunger shaft for metal weight: 16.0 mm
Diameter of metal weight: 50.0 mm
Height of metal weight: 39.0 mm FIG. 3 shows the plunger center P specification details
Diameter m of SFC Plunger center: 59.7 mm
Height n of SFC Plunger center: 16.5 mm
14 holes o with 9.65 mm diameter equally spaced on a 47.8 mm bolt circle and
7 holes p with a diameter of 9.65 mm equally spaced on a 26.7 mm bolt circle
⅝ inches thread q Prior to use, the stainless steel screens of SFC apparatus, should be accurately inspected for clogging, holes or over stretching and replaced when necessary. An SFC apparatus with damaged screen can deliver erroneous SFC results, and must not be used until the screen has been fully replaced.

Measure and clearly mark, with a permanent fine marker, the cylinder at a height of 5.00 cm (±0.05 cm) above the screen attached to the bottom of the cylinder. This marks the fluid level to be maintained during the analysis. Maintenance of correct and constant fluid level (hydrostatic pressure) is critical for measurement accuracy.

A constant hydrostatic head reservoir C is used to deliver NaCl solution to the cylinder and maintain the level of solution at a height of 5.0 cm above the screen attached to the bottom of the cylinder. The bottom end of the reservoir air-intake tube A is positioned so as to maintain the fluid level in the cylinder at the required 5.0 cm height during the measurement, i.e., the height of the bottom of the air tube A from the bench top is the same as the height from the bench top of the 5.0 cm mark on the cylinder as it sits on the support screen above the receiving vessel. Proper height alignment of the air intake tube A and the 5.0 cm fluid height mark on the cylinder is critical to the analysis. A suitable reservoir consists of a jar containing: a horizontally oriented L-shaped delivery tube E for fluid delivering, an open-ended vertical tube A for admitting air at a fixed height within the reservoir, and a stoppered vent B for re-filling the reservoir. The delivery tube E, positioned near the bottom of the reservoir C, contains a stopcock F for starting/stopping the delivery of fluid. The outlet of the tube is dimensioned to be inserted through the opening in the cylinder lid O, with its end positioned below the surface of the fluid in the cylinder (after the 5 cm height is attained). The air-intake tube is held in place with an o-ring collar. The reservoir can be positioned on a laboratory jack D in order to adjust its height relative to that of the cylinder. The components of the reservoir are sized so as to rapidly fill the cylinder to the required height (i.e., hydrostatic head) and maintain this height for the duration of the measurement. The reservoir must be capable to deliver liquid at a flow rate of minimum 3 g/sec for at least 10 minutes.

Position the plunger/cylinder apparatus on a ring stand with a 16 mesh rigid stainless steel support screen (or equivalent). This support screen is sufficiently permeable so as to not impede fluid flow and rigid enough to support the stainless steel mesh cloth preventing stretching. The support screen should be flat and level to avoid tilting the cylinder apparatus during the test. Collect the fluid passing through the screen in a collection reservoir, positioned below (but not supporting) the support screen. The collection reservoir is positioned on a balance accurate to at least 0.01 g. The digital output of the balance is connected to a computerized data acquisition system.

Preparation of Reagents

Following preparations are referred to a standard 1 liter volume. For preparation multiple than 1 liter, all the ingredients must be calculated as appropriate.

Jayco Synthetic Urine

Fill a 1 L volumetric flask with de-ionized water to 80% of its volume, add a stir bar and put it on a stirring plate. Separately, using a weighing paper or beaker weigh (accurate to ±0.01 g) the amounts of the following dry ingredients using the analytical balance and add them into the volumetric flask in the same order as listed below. Mix until all the solids are dissolved then remove the stir bar and dilute to 1 L volume with distilled water. Add a stir bar again and mix on a stirring plate for a few minutes more. The conductivity of the prepared solution must be 7.6±0.23 mS/cm.

Chemical Formula Anhydrous [Hydrated]
Potassium Chloride (KCl) 2.00 g
Sodium Sulfate ($Na_2SO_4$) 2.00 g
Ammonium dihydrogen phosphate ($NH_4H_2PO_4$) 0.85 g
Ammonium phosphate, dibasic (($NH_4)_2HPO_4$) 0.15 g
Calcium Chloride ($CaCl_2$) 0.19 g—[Calcium chloride hydrated ($2H_2O$) 0.25 g]
Magnesium chloride ($MgCl_2$) 0.23 g—[Magnesium chloride hydrated ($6H_2O$) 0.50 g]

To make the preparation faster, wait until total dissolution of each salt before adding the next one. Jayco may be stored in a clean glass container for 2 weeks. Do not use if solution becomes cloudy. Shelf life in a clean plastic container is 10 days.

0.118 M Sodium Chloride (NaCl) Solution

Using a weighing paper or beaker weigh (accurate to +0.01 g) 6.90 g of sodium chloride into a 1 L volumetric flask and fill to volume with de-ionized water. Add a stir bar and mix on a stirring plate until all the solids are dissolved. The conductivity of the prepared solution must be 12.50±0.38 mS/cm.

Test Preparation

Using a reference metal cylinder (40 mm diameter; 140 mm height) set the caliper gauge (e.g. Mitotoyo Digimatic Height Gage) to read zero. This operation is conveniently performed on a smooth and level bench top. Position the SFC apparatus without AGM under the caliper gauge and record the caliper as L1 to the nearest of 0.01 mm.

Fill the constant hydrostatic head reservoir with the 0.118 M NaCl solution. Position the bottom of the reservoir air-intake tube A so as to maintain the top part of the liquid meniscus in the SFC cylinder at the required 5.0 cm height during the measurement. Proper height alignment of the air-intake tube A at the 5 cm fluid height mark on the cylinder is critical to the analysis.

Saturate an 8 cm fritted disc (7 mm thick; e.g. Chemglass Inc. # CG 201-51, coarse porosity) by adding excess synthetic urine on the top of the disc. Repeating until the disc is saturated. Place the saturated fritted disc in the hydrating dish and add the synthetic urine until it reaches the level of the disc. The fluid height must not exceed the height of the disc.

Place the collection reservoir on the balance and connect the digital output of the balance to a computerized data acquisition system. Position the ring stand with a 16 mesh rigid stainless steel support screen above the collection dish. This 16 mesh screen should be sufficiently rigid to support the SFC apparatus during the measurement. The support screen must be flat and level.

AGM Sampling

AGM samples should be stored in a closed bottle and kept in a constant, low humidity environment. Mix the sample to evenly distribute particle sizes. Remove a representative sample of material to be tested from the center of the container using the spatula. The use of a sample divider is recommended to increase the homogeneity of the sample particle size distribution.

SFC Procedure

Position the weighing funnel on the analytical balance plate and zero the balance. Using a spatula weigh 0.9 g (±0.05 g) of AGM into the weighing funnel. Position the SFC cylinder on the bench, take the weighing funnel and gently, tapping with finger, transfer the AGM into the cylinder being sure to have an evenly dispersion of it on the screen. During the AGM transfer, gradually rotate the cylinder to facilitate the dispersion and get homogeneous distribution. It is important to have an even distribution of particles on the screen to obtain the highest precision result. At the end of the distribution the AGM material must not adhere to the cylinder walls. Insert the plunger shaft into the lid central hole then insert the plunger center into the cylinder for few centimeters. Keeping the plunger center away from AGM insert the lid in the cylinder and carefully rotate it until the alignment between the two is reached. Carefully rotate the plunger to reach the alignment with lid then move it down allowing it to rest on top of the dry AGM. Insert the stainless steel weight to the plunger rod and check if the lid moves freely. Proper seating of the lid prevents binding and assures an even distribution of the weight on the gel bed.

The thin screen on the cylinder bottom is easily stretched. To prevent stretching, apply a sideways pressure on the plunger rod, just above the lid, with the index finger while grasping the cylinder portion of the apparatus. This "locks" the plunger in place against the inside of the cylinder so that the apparatus can be lifted. Place the entire apparatus on the fritted disc in the hydrating dish. The fluid level in the dish should not exceed the height of the fritted disc. Care should be taken so that the layer does not loose fluid or take in air during this procedure. The fluid available in the dish should be enough for all the swelling phase. If needed, add more fluid to the dish during the hydration period to ensure there is sufficient synthetic urine available. After a period of 60 minutes, place the SFC apparatus under the caliper gauge and record the caliper as L2 to the nearest of 0.01 mm. Calculate, by difference L2−L1, the thickness of the gel layer as L0 to the nearest ±0.1 mm. If the reading changes with time, record only the initial value.

Transfer the SFC apparatus to the support screen above the collection dish. Be sure, when lifting the apparatus, to lock the plunger in place against the inside of the cylinder. Position the constant hydrostatic head reservoir such that the delivery tube is placed through the hole in the cylinder lid. Initiate the measurement in the following sequence:

a) Open the stopcock of the constant hydrostatic head reservoir and permit the fluid to reach the 5 cm mark. This fluid level should be obtained within 10 seconds of opening the stopcock.
b) Once 5 cm of fluid is attained, immediately initiate the data collection program.

With the aid of a computer attached to the balance, record the quantity of fluid passing through the gel layer versus time at intervals of 20 seconds for a time period of 10 minutes. At the end of 10 minutes, close the stopcock on the reservoir. The data from 60 seconds to the end of the experiment are used in the calculation. The data collected prior to 60 seconds are not included in the calculation. Perform the test in triplicate for each AGM sample.

Evaluation of the measurement remains unchanged from EP-A 640 330. Through-flux is captured automatically. Saline flow conductivity (SFC) is calculated as follows:

$$SFC\ [cm^3\ s/g]=(Fg(t=0)\times L_0)/(d\times A\times WP),$$

where $Fg(t=0)$ is the through-flux of NaCl solution in g/s, which is obtained from a linear regression analysis of the $Fg(t)$ data of the through-flux determinations by extrapolation to t=0, $L_0$ is the thickness of the gel layer in cm, d is the density of the NaCl solution in g/cm$^3$, A is the area of the gel layer in cm$^2$ and WP is the hydrostatic pressure above the gel layer in dyn/cm$^2$.

CS-SFC (Core Shell Saline Flow Conductivity)

CS-SFC is determined completely analogously to SFC, with the following changes:

To modify the SFC the person skilled in the art will design the feed line including the stopcock in such a way that the hydrodynamic resistance of the feed line is so low that prior to the start of the measurement time actually used for the evaluation an identical hydrodynamic pressure as in the SFC (5 cm) is attained and is also kept constant over the duration of the measurement time used for the evaluation.

- the weight of AGM used is 1.50+/−0.05 g
- a 0.9% by weight sodium chloride solution is used as solution to preswell the AGM sample and for through-flux measurement
- the preswell time of the sample for measurement is 240 minutes
- for preswelling, a filter paper 90 mm in diameter (Schleicher & Schüll, No 597) is placed in a 500 ml crystallizing dish (Schott, diameter=115 mm, height=65 mm) and 250 ml of 0.9% by weight sodium chloride solution are added, then the SFC measuring cell with the sample is placed on the filter paper and swelling is allowed for 240 minutes
- the through-flux data are recorded every 5 seconds, for a total of 3 minutes
- the points measured between 10 seconds and 180 seconds are used for evaluation and $Fg(t=0)$ is the through-flux of NaCl solution in g/s which is obtained from a linear regression analysis of the $Fg(t)$ data of the through-flux determinations by extrapolation to t=0
- the stock reservoir bottle in the SFC-measuring apparatus for through-flux solution contains about 5 kg of sodium chloride solution.

Methods for Analyzing the Coating Polymers:

Preparation of Films of the Elastic Film-Forming Polymer

In order to subject the elastic film-forming polymer used herein to some of the test methods below, including the Wet-elongation test, films need to be obtained of said polymers thereof.

The preferred average (as set out below) caliper of the (dry) films for evaluation in the test methods herein is around 60 µm.

Methods to prepare films are generally known to those skilled in the art and typically comprise solvent casting, hot-melt extrusion or melt blowing films. Films prepared by these methods may have a machine direction that is defined as the direction in which the film is drawn or pulled. The direction perpendicular to the machine direction is defined as the cross-direction.

For the purpose of the invention, the films used in the test methods below are formed by solvent casting, except when the elastic film-forming polymer cannot be made into a solution or dispersion of any of the solvents listed below, and then the films are made by hotmelt extrusion as described below. (The latter is the case when particulate matter from the elastic film-forming polymer is still visible in the mixture of the material or coating agent and the solvent, after attempting to dissolve or disperse it at room temperature for a period between 2 to 48 hours, or when the viscosity of the solution or dispersion is too high to allow film casting.)

The resulting film should have a smooth surface and be free of visible defects such as air bubbles or cracks.

An example to prepare a solvent cast film herein from a elastic film-forming polymer:
The film to be subjected to the tests herein can be prepared by casting a film from a solution or dispersion of said material or coating agent as follows:
The solution or dispersion is prepared by dissolving or dispersing the elastic film-forming polymer, at 10 weight %, in water, or if this is not possible, in THF (tetrahydrofuran), or if this is not possible, in dimethylformamide (DMF), or if this is not possible in methyl ethyl ketone (MEK), or if this is not possible, in dichloromethane or if this is not possible in toluene, or if this is not possible in cyclohexane (and if this is not possible, the hotmelt extrusion process below is used to form a film). Next, the dispersion or solution is poured into a Teflon dish and is covered with aluminum foil to slow evaporation, and the solvent or dispersant is slowly evaporated at a temperature above the minimum film forming temperature of the polymer, typically about 25° C., for a long period of time, e.g. during at least 48 hours, or even up to 7 days. Then, the films are placed in a vacuum oven for 6 hours, at 25° C., to ensure any remaining solvent is removed.
The process to form a film from an aqueous dispersions is as follows:

The dispersion may be used as received from the supplier, or diluted with water as long as the viscosity remains high enough to draw a film (200-500 cps). The dispersion (5-10 ml) is placed onto a piece of aluminum foil that is attached to the stage of the draw down table. The polymer dispersion is drawn using a Gardner metering rod #30 or #60 to draw a film that is 50-100 microns thick after drying. The dispersant is slowly evaporated at a temperature above the minimum film forming temperature of the polymer, typically about 25° C., for a long period of time, e.g. during at least 48 hours, or even up to 7 days. The film is heated in a vacuum oven at 150° C. for a minimum of 5 minutes up to 2 h, then the film is removed from the foil substrate by soaking in warm water bath for 5 to 10 min to remove the films from the substrate. The removed film is then placed onto a Teflon sheet and dried under ambient conditions for 24 h. The dried films are then sealed in a plastic bag until testing can be performed.
The process to prepare a hotmelt extruded film herein is as follows:

If the solvent casting method is not possible, films of the elastic film-forming polymer 1 herein may be extruded from a hot melt using a rotating single screw extrusion set of equipment operating at temperatures sufficiently high to allow the elastic film-forming polymer to flow. If the polymer has a melting temperature Tm, then the extrusion should take place at least 20 K above said Tm. If the polymer is amorphous (i.e. does not have a Tm), steady shear viscometry can be performed to determine the order to disorder transition for the polymer, or the temperature where the viscosity drops dramatically. The direction that the film is drawn from the extruder is defined as the machine direction and the direction perpendicular to the drawing direction is defined as the cross direction.

| For example | Wet-extensible material | Die Temperature [° C.] | Screw rpm |
|---|---|---|---|
| A | Irogran VP 654/5 | 180 | 40 |
| B | Elastollan LP 9109 | 170 | 30 |
| C | Estane 58245 | 180 | 30 |

-continued

| For example | Wet-extensible material | Die Temperature [° C.] | Screw rpm |
|---|---|---|---|
| D | Estane 4988 | 180 | 30 |
| E | Pellethane 2103-70A | 185 | 30 |

Heat-Treatment of the Films:

The heat-treatment of the films should, for the purpose of the test methods below, be done by placing the film in a vacuum oven at a temperature which is about 20 K above the highest Tg of the used elastic film-forming polymer, and this is done for 2 hours in a vacuum oven at less than 0.1 Torr, provided that when the elastic film-forming polymer has a melting temperature Tm, the heat-treatment temperature is at least 20 K below the Tm, and then preferably (as close to) 20 K above the highest Tg. When the Tg is reached, the temperature should be increased slowly above the highest Tg to avoid gaseous discharge that may lead to bubbles in the film. For example, a material with a hard segment Tg of 70° C. might be heat-treated at 90° C. for 10 min, followed by incremental increases in temperature until the heat-treatment temperature is reached.

If the elastic film-forming polymer has a Tm, then said heat-treatment of the films (prepared as set out above and to be tested by the methods below) is done at a temperature which is above the (highest) Tg and at least 20 K below the Tm and (as close to) 20 K above the (highest) Tg. For example, a wet-extensible material that has a Tm of 135° C. and a highest Tg (of the hard segment) of 100° C., would be heat-treated at 115° C.

In the absence of a measurable Tg or Tm, the temperature for heat-treatment in this method is the same as used in the process for making water-absorbing material.
Removal of Films, if Applicable If the dried and optionally heat-treated films are difficult to remove from the film-forming substrate, then they may be placed in a warm water bath for 30 s to 5 min to remove the films from the substrate. The film is then subsequently dried for 6-24 h at 25° C.
Wet-Elongation Test and Wet-Tensile-Stress Test:

This test method is used to measure the wet-elongation at break (=extensibility at break) and tensile properties of films of elastic film-forming polymers as used herein, by applying a uniaxial strain to a flat sample and measuring the force that is required to elongate the sample. The film samples are herein strained in the cross-direction, when applicable.

A preferred piece of equipment to do the tests is a tensile tester such as an MTS Synergie100 or an MTS Alliance available from MTS Systems Corporation 14000 Technology Drive, Eden Prairie, Minn., USA, with a 25N or 50N load cell. This measures the Constant Rate of Extension in which the pulling grip moves at a uniform rate and the force measuring mechanisms moves a negligible distance (less than 0.13 mm) with increasing force. The load cell is selected such that the measured loads (e.g. force) of the tested samples will be between 10 and 90% of the capacity of the load cell.

Each sample is die-cut from a film, each sample being 1×1 inch (2.5×2.5 cm), as defined above, using an anvil hydraulic press die to cut the film into sample(s) (Thus, when the film is made by a process that does not introduce any orientation, the film may be tested in either direction.). Test specimens (minimum of three) are chosen which are substantially free of visible defects such as air bubbles, holes, inclusions, and cuts. They must also have sharp and substantially defect-free edges.

The thickness of each dry specimen is measured to an accuracy of 0.001 mm with a low pressure caliper gauge such as a Mitutoyo Caliper Gauge using a pressure of about 0.1 psi. Three different areas of the sample are measured and the average caliper is determined. The dry weight of each specimen is measured using a standard analytical balance to an accuracy of 0.001 g and recorded. Dry specimens are tested without further preparation for the determination of dry-elongation, dry-secant modulus, and dry-tensile stress values used herein.

For wet testing, preweighed dry film specimens are immersed in saline solution [0.9% (w/w) NaCl] for a period of 24 hours at ambient temperature (23+/−2° C.). Films are secured in the bath with a 120-mesh corrosion-resistant metal screen that prevents the sample from rolling up and sticking to itself. The film is removed from the bath and blotted dry with an absorbent tissue such as a Bounty© towel to remove excess or non-absorbed solution from the surface. The wet caliper is determined as noted for the dry samples. Wet specimens are used for tensile testing without further preparation. Testing should be completed within 5 minutes after preparation is completed. Wet specimens are evaluated to determine wet-elongation, wet-secant modulus, and wet-tensile stress.

For the purpose of the present invention the Elongation to (or at) Break will be called Wet-elongation to (or at) Break and the tensile stress at break will be called Wet Stress at Break. (At the moment of break, the elongation to break % is the wet extensibility at break as used herein.)

Tensile testing is performed on a constant rate of extension tensile tester with computer interface such as an MTS Alliance tensile tester with Testworks 4 software. Load cells are selected such that measured forces fall within 10-90% of the cell capacity. Pneumatic jaws, fitted with flat 1"-square rubber-faced grips, are set to give a gauge length of 1 inch. The specimen is loaded with sufficient tension to eliminate observable slack, but less than 0.05N. The specimens are extended at a constant crosshead speed of 10"/min until the specimen completely breaks. If the specimen breaks at the grip interface or slippage within the grips is detected, then the data is disregarded and the test is repeated with a new specimen and the grip pressure is appropriately adjusted. Samples are run in triplicate to account for film variability.

The resulting tensile force-displacement data are converted to stress-strain curves using the initial sample dimensions from which the elongation, tensile stress, and modulus that are used herein are derived. Tensile stress at break is defined as the maximum stress measured as a specimen is taken to break, and is reported in MPa. The break point is defined as the point on the stress-strain curve at which the measured stress falls to 90% of its maximum value. The elongation at break is defined as the strain at that break point and is reported relative to the initial gauge length as a percentage. The secant modulus at 400% elongation is defined as the slope of the line that intersects the stress-strain curve at 0% and 400% strain. Three stress-strain curves are generated for each elastomeric film coating that is evaluated. Elongation, tensile stress, and modulus used herein are the average of the respective values derived from each curve.

The dry secant elastic modulus at 400% elongation ($SM_{dry,\,400\%}$) is calculated by submitting a dry film, as obtainable by the methods described above (but without soaking it in the 0.9% NaCl solution), to the same tensile test described above, and then calculating the slope of the line intersecting with the zero intercept and the stress-strain curve at 400%, as done above.

Glass Transition Temperatures

Glass Transition Temperatures (Tg's) are determined for the purpose of this invention by differential scanning calorimetry (DSC). The calorimeter should be capable of heating/cooling rates of at least 20° C./min over a temperature range, which includes the expected Tg's of the sample that is to be tested, e.g. of from −90° C. to 250° C., and the calorimeter should have a sensitivity of about 0.2 µW. TA Instruments Q1000 DSC is well-suited to determining the Tg's referred to herein. The material of interest can be analyzed using a temperature program such as: equilibrate at −90° C., ramp at 20° C./min to 120° C., hold isothermal for 5 minutes, ramp 20° C./min to −90° C., hold isothermal for 5 minutes, ramp 20° C./min to 250° C. The data (heat flow versus temperature) from the second heat cycle is used to calculate the Tg via a standard half extrapolated heat capacity temperature algorithm. Typically, 3-5 g of a sample material is weighed (+/− 0.1 g) into an aluminum DSC pan with crimped lid.

As used herein $Tg_1$ will be a lower temperature than $Tg_2$.

Polymer Molecular Weights

Gel Permeation Chromatography with Multi-Angle Light Scattering Detection (GPC-MALS) may be used for determining the molecular weight of the elastic film-forming polymers herein. Molecular weights referred to herein are the weight-average molar mass (Mw). A suitable system for making these measurements consists of a DAWN DSP Laser Photometer (Wyatt Technology), an Optilab DSP Interferometric Refractometer (Wyatt Technology), and a standard HPLC pump, such as a Waters 600E system, all run via ASTRA software (Wyatt Technology).

As with any chromatographic separation, the choice of solvent, column, temperature and elution profiles and conditions depends upon the specific polymer, which is to be tested. The following conditions have been found to be generally applicable for the elastic film-forming polymers referred to herein: Tetrahydrofuran (THF) is used as solvent and mobile phase; a flow rate of 1 mL/min is passed through two 300×7.5 mm, 5 µm, PLgel, Mixed-C GPC columns (Polymer Labs) which are placed in series and are heated to 40-45° C. (the Optilab refractometer is held at the same temperature); 100 µL of a 0.2% polymer solution in THF solution is injected for analysis. The dn/dc values are obtained from the literature where available or calculated with ASTRA utility. The weight-average molar mass (Mw) is calculated by the ASTRA software using the Zimm fit method.

Moisture Vapor Transmission Rate Method (MVTR Method)

MVTR method measures the amount of water vapor that is transmitted through a film under specific temperature and humidity. The transmitted vapor is absorbed by $CaCl_2$ desiccant and determined gravimetrically. Samples are evaluated in triplicate, along with a reference film sample of established permeability (e.g. Exxon Exxaire microporous material #XBF-110W) that is used as a positive control.

This test uses a flanged cup (machined from Delrin (McMaster-Carr Catalog #8572K34) and anhydrous $CaCl_2$ (Wako Pure Chemical Industries, Richmond, Va.; Catalog 030-00525). The height of the cup is 55 mm with an inner diameter of 30 mm and an outer diameter of 45 mm. The cup is fitted with a silicone gasket and lid containing 3 holes for thumb screws to completely seal the cup. Desiccant particles are of a size to pass through a No. 8 sieve but not through a No. 10 sieve. Film specimens approximately 1.5"×2.5" that are free of obvious defects are used for the analysis. The film must completely cover the cup opening, A, which is 0.0007065 $m^2$.

The cup is filled with $CaCl_2$ to within 1 cm of the top. The cup is tapped on the counter 10 times, and the $CaCl_2$ surface is leveled. The amount of $CaCl_2$ is adjusted until the headspace between the film surface and the top of the $CaCl_2$ is 1.0 cm. The film is placed on top of the cup across the opening (30 mm) and is secured using the silicone gasket, retaining ring, and thumb screws. Properly installed, the specimen should not be wrinkled or stretched. The sample assembly is weighed with an analytical balance and recorded to ±0.001 g. The assembly is placed in a constant temperature (40±3° C.) and humidity (75±3% RH) chamber for 5.0 hr ±5 min. The sample assembly is removed, covered with Saran Wrap® and is secured with a rubber band. The sample is equilibrated to room temperature for 30 min, the plastic wrap removed, and the assembly is reweighed and the weight is recorded to ±0.001 g. The absorbed moisture $M_a$ is the difference in initial and final assembly weights. MVTR, in $g/m^2/24$ hr ($g/m^2/$day), is calculated as:

MVTR=$M_a$/($A$*0.208 day)

Replicate results are averaged and rounded to the nearest 100 $g/m^2/24$ hr, e.g. 2865 $g/m^2/24$ hr is herein given as 2900 $g/m^2/24$ hr and 275 $g/m^2/24$ hr is given as 300 $g/m^2/24$ hr.

Method to Determine the Water-Swelling Capacity of the Film-Forming Polymer

The weight of the polymer specimen after soaking for 3 days in an excess of deionized water at room temperature (25° C.) is taken as $W_1$. The weight of this polymer specimen before drying is taken as W0. The water swelling capacity is then calculated as follows:

WSC [g/g]=($W_1$-$W_0$)/$W_0$

The water swelling capacity is the water uptake of the polymer specimen in g water per 1 g of dry polymer. For this test method it is necessary to prepare polymer specimen that are typically not thicker than 1.0 mm for moderately swelling polymers. It may be necessary to prepare polymer films of less than 0.5 mm thickness for low swelling polymers in order to obtain equilibrium swelling after 3 days. A person skilled in the art will adjust the thickness and dry sample weight in a way to obtain equilibrium swelling conditions after 3 days.

Cylinder Centrifuge Retention Capacity CCRC (4 Hours CCRC)

The Cylinder Centrifuge Retention Capacity (CCRC) method determines the fluid retention capacity of the water-swellable materials or polymers (sample) after centrifugation at an acceleration of 250 g, herein referred to as absorbent capacity. Prior to centrifugation, the sample is allowed to swell in excess saline solution in a rigid sample cylinder with mesh bottom and an open top.

Duplicate sample specimens are evaluated for each material tested and the average value is reported.

The CCRC can be measured at ambient conditions by placing the sample material (1.0+/−0.001 g) into a pre-weighed (+/−0.01 g) plexiglass sample container that is open at the top and closed on the bottom with a stainless steel mesh (400) that readily allows for saline flow into the cylinder but contains the absorbent particles being evaluated. The sample cylinder approximates a rectangular prism with rounded-edges in the 67 mm height dimension. The base dimensions (78×58 mm OD, 67.2×47.2 mM ID) precisely match those of modular tube adapters, herein referred to as the cylinder stand, which fit into the rectangular rotor buckets (Heraeus #75002252, VWR #20300-084) of the centrifuge (Heraeus Megafuge 1.0; Heraeus #75003491, VWR #20300-016).

The loaded sample cylinders are gently shaken to evenly distribute the sample across the mesh surface and then placed upright in a pan containing saline solution. The cylinders should be positioned to ensure free flow of saline through the mesh bottom. Cylinders should not be placed against each other or against the wall of the pan, or sealed against the pan bottom. The sample is allowed to swell, without confining pressure and in excess saline, for 4 hours.

After 4 hours, the cylinders are immediately removed from the solution. Each cylinder is placed (mesh side down) onto a cylinder stand and the resulting assembly is loaded into the rotor basket such that the two sample assemblies are in balancing positions in the centrifuge rotor.

The samples are centrifuged for 3 minutes (±10 s) after achieving the rotor velocity required to generate a centrifugal acceleration of 250±5 g at the bottom of the cylinder stand. The openings in the cylinder stands allow any solution expelled from the absorbent by the applied centrifugal forces to flow from the sample to the bottom of the rotor bucket where it is contained. The sample cylinders are promptly removed after the rotor comes to rest and weighed to the nearest 0.01 g.

The cylinder centrifuge retention capacity expressed as grams of saline solution absorbed per gram of sample material is calculated for each replicate as follows:

$$CCRC = \frac{m_{CS} - (m_{Cb} + m_S)}{m_S} \left[\frac{g}{g}\right]$$

where:
$m_{CS}$: is the mass of the cylinder with sample after centrifugation [g]
$m_{Cb}$: is the mass of the dry cylinder without sample [g]
$m_S$: is the mass of the sample without saline solution [g]

The CCRC referred to herein is the average of the duplicate samples reported to the nearest 0.01 g/g.

Method to Determine the Theoretical Equivalent Shell Caliper of the Water-Swellable Material Herein If the amount of film forming polymer comprised in the water-absorbing material is known, a theoretical equivalent average caliper may be determined as defined below.

This method calculates the average caliper of a coating layer or shell on the water-absorbing material herein, under the assumption that the water-absorbing material is to be monodisperse and spherical (which may not be the case in practice). It is believed that even in the case of irregular shaped particles this method gives a good estimate for the average caliper of the shell.

| Key Parameters | |
|---|---|
| | Symbol |
| INPUT Parameter | |
| Mass Median Particle Size of the water-absorbing polymer (AGM) prior to coating with the film-forming polymer (also called "average diameter") | D_AGM_dry |
| Intrinsic density of the base water-absorbing polymer (bulk phase, without coating) | Rho_AGM_intrinsic |
| Intrinsic density of the film-forming elastomeric polymer (coating or shell only) | Rho_polymer_shell |
| Coating (shell) Weight Fraction of the coated water-absorbing polymer (Percent of film-forming polymer coating as percent of total coated water-absorbing polymer) | c_shell_per_total |

-continued

| Key Parameters | |
|---|---|
| | Symbol |
| OUTPUT Parameters | |
| Average film-forming polymer coating caliper if the water-absorbing polymer is monodisperse and spherical | d_shell |
| Mass Median Particle Size of the coated water-absorbing polymer ("average diameter after coating") | D_AGM_coated |
| Coating Weight Ratio as Percent of Polymer Coating in percent of uncoated water-absorbing polymer weight | c_shell_to_bulk |

Formulas
(note: in this notation: all c which are in percent have ranges of 0 to 1 which is equivalent to 0 to 100%.)

$$d\_shell := \frac{D\_AGM\_dry}{2} \cdot \left[\left[1 + \frac{c\_shell\_per\_total}{(1 - c\_shell\_per\_total)} \cdot \frac{Rho\_AGM\_intrinsic}{Rho\_polymer\_shell}\right]^{\frac{1}{3}} - 1\right]$$

$$D\_coated\_AGM := D\_AGM\_dry + 2 \cdot d\_shell$$

$$c\_shell\_to\_bulk := \frac{c\_shell\_per\_total}{1 - c\_shell\_per\_total}$$

Example Calculation:
D_AGM_dry:=0.4 mm (400 µm); Rho_AGM_intrinsic:=Rho_polymer_shell:=1.5 g/cc

| C_shell_per_total [%] | 1 | 2 | 5 | 10 | 20 | 30 | 40 | 50 |
|---|---|---|---|---|---|---|---|---|
| C_shell_to_bulk [%] | 1.0 | 2.0 | 5.3 | 11 | 25 | 43 | 67 | 100 |
| d_shell [µm] | 0.7 | 1.4 | 3.4 | 7.1 | 15 | 25 | 37 | 52 |
| D_Coated_AGM [µm] | 401 | 403 | 407 | 414 | 431 | 450 | 474 | 504 |

INVENTIVE EXAMPLES

In all examples and comparative examples below—unless stated differently, the amounts of coating-polymer and deagglomerating aids used for coating are expressed as solids based on the amount of superabsorbent polymer.

Coating Agents Used:

| | |
|---|---|
| Permax ® 200 | NOVEON Inc., aqueous Polyurethane dispersion |
| Astacin ® Finish LD 1603 | BASF AG, aqueous Polyurethane dispersion |
| Levasil ® 50 | H. C. STARCK GmbH, aqueous colloidal solution of silica |

Comparative Example 1

Coating of ASAP 510 Z Commercial Product with Permax 200

The 150-500 µm fraction was sieved out of the commercially available product ASAP 510 Z (BASF AG) having the following properties and was then coated with Permax 200 according to the procedure below:

ASAP 510 Z (properties of the 150-500 µm fraction only):
CCRC=25.4 g/g
CS-AUL 0.7 psi=23.9 g/g
CS-SFC=55=$10^{-7}$ [$cm^3$ s/g]

A Wurster laboratory coater from Fa. Waldner without Wurster-tube was used, and the amount of absorbent polymer (ASAP 510 Z, 150-500 µm in this case) per batch was 2000 g. The Wurster apparatus was conical with a lower diameter of 150 mm expanding to an upper diameter of 300 mm, the carrier gas was nitrogen having a temperature of 30° C., and the gas flow speed was 1.4 m/s at a pressure of 2 bar. The bottom plate of the apparatus had drillings with 1.5 mm diameter and an effective open cross-section for through-air-flow of 4.2%.

The coating agents (polymer dispersion: Permax 200, Noveon Inc., deagglomeration agent: Levasil 50, H.C. Starck GmbH) have been atomized and spray-coated using a nitrogen-driven two-material nozzle from Fa. Schlick (Germany) operated in bottom spray mode, opening diameter 1.2 mm, the nitrogen temperature being 25° C. The coating agents have been sprayed each from a 20% by weight aqueous dispersion at a temperature of 23° C. First the aqueous polymer dispersion has been sprayed on, followed immediately by the aqueous dispersion of the deagglomeration agent thereafter.

Based on the weight of the absorbent polymer 2.5 wt. % Permax 200 and 0.5 wt. % Levasil have been used for coating. Spraying time for the polymer dispersion has been 30 minutes, and for the deagglomeration aid 5 minutes.

The coated material was subsequently removed and 1000 g have been transferred into a Lödige plow share mixer type M5R which has been pre-heated with an oil heated jacket (oil temperature about 200° C.). The material was gently agitated at about 20 rpm and heated to a product temperature of 165° C. within 20 minutes. The coated material was continuously agitated and held at that temperature for additional 60 minutes. During this heat treatment step a nitrogen blanket has been applied. Thereafter it was immediately poured onto a stainless steel tray and allowed to cool down to room temperature. Lumps have been removed from the coated material by coarse sieving over a 1000 µm screen and the coated material was subsequently tested for performance.

Example A1

Coating of ASAP 510 Z Commercial Product with Permax 200 and N-Butanol as Coalescing Aid The inventive example was carried out exactly like comparative example 1, except that 1 wt. % n-Butanol (=0.5 g) based on the solids weight of the aqueous Permax 200-dispersion has been added as coalescing aid to that dispersion prior to using it for spray-coating.

Comparative Example A2

Coating of ASAP 510 Z Commercial Product with Astacin Finish LD 1603

The comparative example was carried out exactly like comparative example 1, except that Astacin Finish LD 1603 was used as polymer dispersion.

Based on the weight of the absorbent polymer 1.0 wt. % Astacin Finish LD 1603 and 0.5 wt. % Levasil have been used for coating. Spraying time for the polymer dispersion has been 13 minutes, and for the deagglomeration aid 5 minutes.

Example A2

Coating of ASAP 510 Z Commercial Product with Astacin Finish LD 1603 and N-Butanol as Coalescing Aid The inventive example was carried out exactly like comparative example 2, except that 2.5 wt. % n-Butanol (=0.5 g) based on the solids weight of the aqueous Astacin Finish LD 1603-dispersion has been added as coalescing aid to that dispersion prior to using it for spray-coating.

Comparative Example A3

Coating of ASAP 510 Z Commercial Product with a Mix of 60% Astacin Finish LD 1603 and 40% Lepton TOP LB The comparative example was carried out exactly like comparative example 1, except that a blend of Astacin Finish LD 1603 and Lepton TOP LB was used as polymer dispersion. Based on the weight of the absorbent polymer 0.6 wt. % Astacin Finish LD 1603 and 0.4 wt. % Lepton TOP LB, and finally 0.5 wt. % Levasil have been used for coating. The two dispersions have been blended prior to coating. Spraying time for the polymer dispersion blend has been 13 minutes, and for the deagglomeration aid 5 minutes.

Example A3

Coating of ASAP 510 Z Commercial Product with a Mix of 60% Astacin Finish LD 1603 and 40% Lepton TOP LB and N-Butanol as Coalescing Aid The inventive example was carried out exactly like comparative example 3, except that 2.5 wt. % n-Butanol (=0.3 g) based on the solids weight of the aqueous Astacin Finish LD 1603-dispersion has been added as coalescing aid to that dispersion prior to blending it and using it for spray-coating.

TABLE

Performance data of examples A1-A3

|  | CCRC [g/g] | CS-AUL 0.7 psi [g/g] | CS-SFC [$\times 10^{-7}$ cm$^3$s/g] |
|---|---|---|---|
| Comparative example 1 | 23.6 | 23.0 | 490 |
| Example A1 | 21.8 | 21.8 | 653 |
| Comparative example A2 | 25.2 | 23.0 | 237 |
| Example A2 | 25.2 | 22.9 | 256 |
| Comparative example A3 | 25.4 | 23.1 | 216 |
| Example A3 | 25.2 | 23.8 | 318 |

As can be seen, the inventive examples are much better coated and exhibit higher CS-SFC under identical experimental conditions.

Comparative Example A4

Coating of ASAP 510 Z Commercial Product with Permax 200 without Using a Deagglomeration Agent The 150-500 μm fraction was sieved out of the commercially available product ASAP 510 Z (BASF AG) having the following properties and was then coated with Permax 200 according to the procedure below:

ASAP 510 Z (properties of the 150-500 μm fraction only):
CCRC=25.4 g/g
CS-AUL 0.7 psi=23.9 g/g
CS-SFC=55×10$^{-7}$ [cm$^3$ s/g]

A Wurster laboratory coater from Fa. Waldner without Wurster-tube was used, and the amount of absorbent polymer (ASAP 510 Z, 150-500 μm in this case) per batch was 900 g. The Wurster apparatus was conical with a lower diameter of 150 mm expanding to an upper diameter of 300 mm, the carrier gas was nitrogen having a temperature of 30° C., and the gas flow speed was 1.4 m/s at a pressure of 2 bar. The bottom plate of the apparatus had drillings with 1.5 mm diameter and an effective open cross-section for through-air-flow of 4.2%.

The coating agent (polymer dispersion: Permax 200, Noveon Inc.) has been atomized and spray-coated using a nitrogen-driven two-material nozzle from Fa. Schlick (Germany) operated in bottom spray mode, opening diameter 1.2 mm, the nitrogen temperature being 25° C. The coating agent has been sprayed from a 11% by weight aqueous dispersion at a temperature of 23° C.

Based on the weight of the absorbent polymer 1.0 wt. % Permax 200 has been used for coating.

The coated material was subsequently removed and has been transferred into a second laboratory fluidized bed coater in which it has been held and heat-treated at 185° C. for 45 minutes under nitrogen flow. Thereafter it was immediately poured onto a stainless steel tray and allowed to cool down to room temperature. Lumps have been removed from the coated material by coarse sieving over a 1000 μm screen and the coated material was subsequently tested for performance.

Example A4

Coating of ASAP 510 Z Commercial Product with Permax 200 and Polyethylene Glycol-400 as Coalescing Aid and without Deagglomerating Aid The inventive example was carried out exactly like comparative example 4, except that 2.5 wt. % Polyethylene glycole-400 based on the solids weight of the aqueous Permax 200-dispersion has been added as coalescing aid to that dispersion prior to using it for spray-coating.

Comparative Example A5

Coating of ASAP 510 Z Commercial Product with Lab Prepared Polyurethane Dispersion 1805-40 and without Using a Deagglomeration Agent Comparative example A5 was carried out identical to comparative example A4, except that the Permax 200 has been substituted by 1 wt. % of a laboratory made polyurethane dispersion 1805-40.

The polyurethane dispersion 1805-40 has been prepared as follows:

In a round-neck flask equipped with a reflux-condenser, a stirrer and heated with an oil bath, 800 g (0.40 mol) of a Polyesterole prepared from isophthalic acid, adipic acid and hexanediole-1,6 exhibiting an OH-number of 56 mg/g is added, then 80.4 g (0.60 mol) DMPA (Dimethylolpropionic acid) and 36.0 g (0.40 mol) Butanediole-1,4 are added.

The reaction mass is heated to 105° C. (oil bath temperature) and 400 g (1.80 mol) IPDI (Isophoronediisocyanate) and 160 g Acetone are added. After 4 hours stirring at 105° C. the reaction mass is diluted with 1600 g acetone.

The NCO-content of this solution has been determined to be 1.11%.

The solution is cooled to 45° C. and 68.0 g (0.40 mol) IPDA (Isophoronediamine) is added. After 90 minutes the solution is neutralized by adding 50.0 g (0.73 mol) aqueous ammonia (25% in water). The reaction mass is then dispersed again in 3000 g deionised water and the acetone is removed under vacuum.

A transparent polyurethane dispersion with a solid content of 30 wt. % is obtained.

Example A5

Coating of ASAP 510 Z Commercial Product with Lab Prepared Polyurethane Dispersion 1805-40 and N-Butanol as Coalescing Aid and without Deagglomerating Aid The inventive example was carried out exactly like comparative example 5, except that 2.5 wt. % n-Butanol based on the solids weight of the aqueous 1805-40-polyurethane dispersion has been added as coalescing aid to that dispersion prior to using it for spray-coating.

TABLE

Performance data of examples A4-A5

|  | CCRC [g/g] | CS-AUL 0.7 psi [g/g] | CS-SFC [×10⁻⁷ cm³s/g] |
|---|---|---|---|
| Comparative example A4 | 23.4 | 21.2 | 293 |
| Example A4 | 23.7 | 21.9 | 322 |
| Comparative example A5 | 23.4 | 23.4 | 379 |
| Example A5 | 23.7 | 22.7 | 397 |

Example A7-A17

Coating of ASAP 510 Z Commercial Product with Permax 200 Using Different Coalescing Aids The 150-850 μm fraction was sieved out of the commercially available product ASAP 510 Z (BASF AG) having the following properties and was then coated with Permax 200 according to the procedure below:

ASAP 510 Z (properties of the 150-850 μm fraction only):

CCRC=30.7 g/g

CS-AUL 0.7 psi=24.8 g/g

CS-SFC=35×10⁻⁷ [cm³ s/g]

A Wurster laboratory coater from Fa. Waldner without Wurster-tube was used, and the amount of absorbent polymer (ASAP 510 Z, 150-500 μm in this case) per batch was 500 g. The Wurster apparatus was conical with a lower diameter of 150 mm expanding to an upper diameter of 300 mm, the carrier gas was nitrogen having a temperature of 30° C., and the gas flow speed was 1.4 m/s at a pressure of 2 bar. The bottom plate of the apparatus had drillings with 1.5 mm diameter and an effective open cross-section for through-air-flow of 4.2%.

The coating agent (polymer dispersion: Permax 200, Noveon Inc.) has been atomized and spray-coated using a nitrogen-driven two-material nozzle from Fa. Schlick (Germany) operated in bottom spray mode, opening diameter 1.2 mm, the nitrogen temperature being 25° C. The coating agent has been sprayed from a 11% by weight aqueous dispersion at a temperature of 23° C.

Based on the weight of the absorbent polymer 2.5 wt. % Permax 200 has been used for coating in all the examples. A coalescing aid has been used as given in the table below, which was either mixed into the Permax-dispersion, or sprayed on separately onto the Permax-film afterwards. The amount of the coalescing aid has been always calculated based on the amount of Permax 200 solids.

The coated material was subsequently removed and has been transferred onto teflonized trays and was dried at 150° C. for 2 hours in a vacuum oven.

Thereafter it was allowed to cool down to room temperature. Lumps have been removed from the coated material by coarse sieving over a 1000 μm screen and the coated material was subsequently tested for performance.

Comparative Example A6

Coating of ASAP 510 Z Commercial Product with Permax 200 without Coalescing Aid

The comparative example A6 has been carried out exactly like the inventive examples A7-A17 except that no coalescing aid has been used.

TABLE

Performance data of examples A7-A17

| Example | Coalescing aid (type) | Coalescing aid [wt. %]* | Addition method | CCRC [g/g] | CS-AUL 0.7 psi [g/g] | CS-SFC [×10⁻⁷ cm³s/g] |
|---|---|---|---|---|---|---|
| Comparative A6 | none | none | none | 28.6 | 25.6 | 539 |
| A7 | PEG-400 | 1.0 | blend | 27.9 | 25.1 | 723 |
| A8 | PEG-400 | 2.5 | blend | 28.1 | 24.6 | 763 |
| A9 | PEG-400 | 5.0 | blend | 27.9 | 21.3 | 599 |

TABLE-continued

Performance data of examples A7-A17

| Example | Coalescing aid (type) | Coalescing aid [wt. %]* | Addition method | CCRC [g/g] | CS-AUL 0.7 psi [g/g] | CS-SFC [×10$^{-7}$ cm$^3$s/g] |
|---|---|---|---|---|---|---|
| A10 | PEG-400 | 1.0 | separate | 27.1 | 24.4 | 816 |
| A11 | n-Butanole | 1.0 | separate | 27.2 | 24.5 | 548 |
| A12 | 2-Methyl-2,4-pentan-diole | 1.0 | separate | 28.1 | 24.6 | 706 |
| A13 | n-Butanole | 1.0 | blend | 27.7 | 25.4 | 861 |
| A14 | 1,2-Propandiole | 1.0 | blend | 27.9 | 24.6 | 753 |
| A15 | 1,3-Propandiole | 1.0 | blend | 27.9 | 24.2 | 686 |
| A16 | Diethylenegly-colebutylether | 1.0 | blend | 27.0 | 24.7 | 624 |
| A17 | 3-Methoxy-1-butyl acetate | 1.0 | blend | 28.2 | 24.8 | 691 |

*based on Permax 200 solids
blend: coalescing aid was added into Permax prior to spray-coating
separate: coalescing aid was sprayed on separately after coating with Permax Example A18

Determination of the Optimum Heat Treatment Period

Example A13 has been reproduced, except that the coated material was not dried on teflonized trays but subsequently removed from the coater and transferred into a second laboratory fluidized bed dryer in which it has been held and heat treated at 185° C. for 45 minutes under nitrogen flow. Every 10 minutes a small sample was taken and allowed to cool down to room temperature. Lumps have been removed from the samples of the coated material by coarse sieving over a 1000 μm screen and the coated material was subsequently tested for performance.

When the CS-SFC is plotted vs. heat treatment time then a clear maximum is found after 30 minutes.

TABLE

Determination of the optimum heat treatment period of Example A18

| Heat treatment time [min] | CCRC [g/g] | CCRC (only 60 min AGM swelling instead of 4 hours) [g/g] | CS-SFC [×10$^{-7}$ cm$^3$s/g] |
|---|---|---|---|
| 10 | | | 85 |
| 20 | 28.4 | 27.4 | 637 |
| 30 | 27.1 | 26.4 | 957 |
| 40 | 26.3 | 25.7 | 634 |
| 50 | | | 437 |
| 60 | | | 202 |

Example A19

Determination of the Optimum Heat Treatment Period

Example A15 has been reproduced, except that the coated material was not dried on teflonized trays but subsequently removed from the coater and transferred into a second laboratory fluidized bed dryer in which it has been held and heat treated at 185° C. for 45 minutes under nitrogen flow. Every 10 minutes a small sample was taken and allowed to cool down to room temperature. Lumps have been removed from the samples of the coated material by coarse sieving over a 1000 μm screen and the coated material was subsequently tested for performance.

TABLE

Determination of the optimum heat treatment period of Example A19

| Heat treatment time [min] | CCRC [g/g] | CCRC (only 60 min AGM swelling instead of 4 hours) [g/g] | CS-SFC [×10$^{-7}$ cm$^3$s/g] |
|---|---|---|---|
| 10 | | | 128 |
| 20 | 27.8 | 26.9 | 954 |
| 30 | 26.0 | 25.7 | 742 |
| 40 | 25.1 | 24.9 | 248 |
| 50 | | | 114 |
| 60 | | | 60 |

BLENDING EXAMPLES

Examples B1-B13

Coating of ASAP 510 Z Commercial Product with Non-Polyurethane Dispersions, Polyurethane Dispersions and Blends of Dispersions In the examples that follow all samples have been prepared exactly like comparative example 1, except that non-Polyurethane dispersions or blends of dispersions have been used in the amounts given in the table. The respective amounts in weight % are based on the weight of the water-absorbing polymeric particles used.

Blends have been obtained by mixing at least two polymer dispersions together.

For 2.5 wt. % polymer coating out of 20 wt. % concentrated dispersion, the spraying time was about 30 minutes like in comparative example 1.

For 1.5 wt. % the spraying time was about 20 minutes, and for 1.0 wt. % the spraying time was about 13 minutes.

Commercial Dispersions Used for the Examples:

| | |
|---|---|
| Airflex EP 17: | Air Products Polymers B.V., aqueous Dispersion based on Vinylacetate-Ethylene-copolymer. |
| Astacin Finish LD 1603: | BASF AG, aqueous polyurethane dispersion |
| Lepton TOP LB: | BASF AG, aqueous dispersion based on polyacrylate and wax |

-continued

| | |
|---|---|
| Epotal A 480: | BASF AG, aqueous dispersion based on an anionic styrene-acrylonitrile-acrylate-copolymers. |
| Corial Binder OK: | BASF AG, aqueous dispersion based on polyacrylate, capable of forming films with medium hardness. |
| Corial Binder IF: | BASF AG, aqueous dispersion based on polyacrylate, capable of forming soft films. |
| Corial Ultrasoft NT: | BASF AG, aqueous dispersion based on polyacrylate, capable of forming very soft films. |

TABLE

Performance data of examples B1-B13

| | Coating Dispersion | CS-SFC $[cm^3 \cdot s/g \cdot 10^{-7}]$ | CS-AUL 0.7 [g/g] | CCRC [g/g] |
|---|---|---|---|---|
| Comparative Example 1 | 2.5% Permax 200 | 490 | 23.0 | 23.6 |
| Example B1 | 1.5% Permax + 1.0% Lepton LB | 512 | 21.7 | 23.5 |
| Example B2 | 2.5% Epotal A 480 | 226 | 19.5 | 25.7 |
| Example B3 | 2.5% Corial Binder OK | 180 | 22.7 | 25.5 |
| Example B4 | 2.5% Corial Binder IF | 266 | 23.1 | 25.7 |
| Example B5 | 2.5% Corial Ultrasoft NT | 230 | 22.3 | 25.7 |
| Example B6 | 2.5% Astacin Finish LD 1603 | 466 | 23.4 | 24.9 |
| Example B7 | 1.5% Astacin Finish LD 1603 | 321 | 23.2 | 25.4 |
| Example B8 | 1.0% Astacin Finish LD 1603 | 237 | 23.0 | 25.2 |
| Example B9 | 0.6% Astacin Finish LD 1603 0.4% Corial OK | 244 | 23.4 | 25.1 |
| Example B10 | 0.6% Astacin Finish LD 1603 0.4% Corial IF | 274 | 22.8 | 25.0 |
| Example B11 | 0.6% Astacin Finish LD 1603 0.4% Corial Ultrasoft NT | 257 | 23.4 | 25.2 |
| Example B12 | 0.6% Astacin Finish LD 1603 0.4% Lepton LB | 216 | 23.1 | 25.4 |
| Example B13 | 0.6% Astacin Finish LD 1603 0.4% Lepton LB 0.02% n-Butanol (as coalescing aid) | 318 | 23.8 | 25.2 |

All amounts are given in wt. % based on water-absorbing polymeric particles.

Comparative Example C1

Coating of ASAP 510 Z Commercial Product with a Polyurethane Dispersion Containing No Anti-Oxidant The 150-500 µm fraction was sieved out of the commercially available product ASAP 510 Z (BASF AG) having the following properties and was then coated with Permax 200 according to the procedure below:
ASAP 510 Z (properties of the 150-500 µm fraction only):
CCRC=25.4 g/g
CS-AUL 0.7 psi=23.9 g/g
CS-SFC=55×10$^{-7}$ [cm$^3$ s/g]
A Wurster laboratory coater from Fa. Waldner without Wurster-tube was used, and the amount of absorbent polymer (ASAP 510 Z, 150-500 µm in this case) per batch was 2000 g. The Wurster apparatus was conical with a lower diameter of 150 mm expanding to an upper diameter of 300 mm, the carrier gas was nitrogen having a temperature of 30° C., and the gas flow speed was 1.4 m/s at a pressure of 2 bar. The bottom plate of the apparatus had drillings with 1.5 mm diameter and an effective open cross-section for through-air-flow of 4.2%.
The coating agents (polymer dispersion: as per formulation of 1805-40 given below, deagglomeration agent: Levasil 50, H.C. Starck GmbH) have been atomized and spray-coated using a nitrogen-driven two-material nozzle from Fa. Schlick (Germany) operated in bottom spray mode, opening diameter 1.2 mm, the nitrogen temperature being 25° C. The coating agents have been sprayed each from a 20% by weight aqueous dispersion at a temperature of 23° C. First the aqueous polymer dispersion has been sprayed on, followed immediately by the aqueous dispersion of the deagglomeration agent thereafter.

Based on the weight of the absorbent polymer 2.5 wt. % Polymer dispersion and 0.5 wt. % Levasil have been used for coating. Spraying time for the polymer dispersion has been 30 minutes, and for the deagglomeration aid 5 minutes.

The coated material was subsequently removed and 200 g have been transferred into a laboratory fluidized bed dryer and allowed to dry in an air-flow at 185° C. for 10 minutes and for 20 minutes, respectively. At the respective times a small sample of 10 g has been extracted for analysis. Thereafter it was immediately poured onto a stainless steel tray and allowed to cool down to room temperature. Lumps have been removed from the coated material by coarse sieving over a 1000 µm screen and the coated material was subsequently tested for performance.
Preparation of the Polymer Dispersion:
The polyurethane dispersion 1805-40 has been prepared as follows:
In a round-neck flask equipped with a reflux-condenser, a stirrer and heated with an oil bath, 800 g (0.40 mol) of a Polyesterole prepared from isophthalic acid, adipic acid and hexanediole-1,6 exhibiting an OH-number of 56 mg/g is added, then 80.4 g (0.60 mol) DMPA (Dimethylolpropionic acid) and 36.0 g (0.40 mol) Butanediole-1,4 are added.
The reaction mass is heated to 105° C. (oil bath temperature) and 400 g (1.80 mol) IPDI (Isophoronediisocyanate) and 160 g Acetone are added. After 4 hours stirring at 105° C. the reaction mass is diluted with 1600 g acetone.
The NCO-content of this solution has been determined to be 1.11%.
The solution is cooled to 45° C. and 68.0 g (0.40 mol) IPDA (Isophoronediamine) is added. After 90 minutes the solution is neutralized by adding 50.0 g (0.73 mol) aqueous ammonia (25% in water). The reaction mass is then dispersed again in 3000 g deionised water and the acetone is removed under vacuum.

A transparent polyurethane dispersion with a solids content of 30 wt. % is obtained.

Comparative Example C2

Coating of ASAP 510 Z Commercial Product with a Polyurethane Dispersion Containing No Anti-Oxidant This example was carried out exactly like comparative example C1 except that a nitrogen flow was used in the heat treatment step.

Examples C1 Through C8

Coating of ASAP 510 Z Commercial Product with a Polyurethane Dispersion Containing an Anti-Oxidant Examples C1 through C8 have been carried out exactly like comparative example C1 except that the respective anti-oxidant as listed in the following table has been added to the polyurethane solution before the addition of the aqueous ammonia.

Masterbatches with 3 wt. % or 4.5 wt. % of anti-oxidant based on the content of polyurethane polymer in the respective dispersion have been prepared. These masterbatches have been further diluted with an identical dispersion which was prepared free of anti-oxidants to yield the dispersions as listed in the following table.

TABLE

Performance data of examples C1-C8

| | Carrier gas for fluid bed | Antioxidant Type | wt. %*** | CS-SFC after 10 Min heat treatment (cm$^3$*s/g*10$^{-7}$) | CS-SFC after 20 Min heat treatment (cm$^3$*s/g*10$^{-7}$) |
|---|---|---|---|---|---|
| Comparative Example C1 | Air | — | — | 92 | 310 |
| Comparative Example C2 | Nitrogen | — | — | 124 | 490 |
| Example C1 | Air | Chromanol | 1% | 171 | 379 |
| Example C2 | Air | Chromanol | 3% | 122 | 566 |
| Example C3 | Air | Vitamine E | 1% | 103 | 432 |
| Example C4 | Air | Vitamine E | 3% | 107 | 469 |
| Example C5 | Air | Irganox 1010 | 1% | 113 | 524 |
| Example C6 | Air | Irganox 1010 | 3% | 180 | 402 |
| Example C7 | Air | Mix* of Chromanol + Vitamine E + Irganox 1010 | 1%** | 184 | 392 |
| Example C8 | Air | Mix*of Chromanol + Vitamine E + Irganox 1010 | 3%** | 147 | 482 |

*the blending ratio by weight of the individual components in this mix is: Chromanol/Vitamine E/Irganox 1010 = 1/6.2/8.6.
**total usage amount of the mix as described in *)
***weight % based on solids in the polymer dispersion used for coating Irganox 1010:
Trade product of CIBA GmbH
Pentaerythrittetrakis(3,5-di-tert-butyl-4-hydroxyphenyl)propionate
CAS-Nummer 006683-19-8

While particular embodiments of the present invention have been illustrated and described, it would be obvious to those skilled in the art that various other changes and modifications that are within the scope of this invention. Each embodiment defined by certain properties or dimension for which a value is defined herein is to be understood to include embodiments with functional equivalent properties or dimensions, e.g. a dimension of 0.5 cm has to be understood as meaning "about 0.5 cm".

What is claimed is:

1. An absorbent structure for use in an adult or infant diapers or feminine hygiene articles, the absorbent structure comprising a water-absorbing material, the water-absorbing material comprising super absorbent polymer particles coated with a film coating, the film coating comprising an elastic film-forming polyurethane and a coalescing agent, the coalescing agent being miscible to at least 10 wt. % with water at 25 C and 1 bar ambient pressure, the water-absorbing material having a CCRC and CRC of not less than 25 g/g, and/or a CS-SFC of at least 350×10$^{-7}$ cm$^3$ s/g, wherein the film coating is applied in an amount of 0.01% to 25% by weight based on the weight of the water-absorbing material and the coalescing agent is present in an amount of not more than 10% by weight based on the weight of the film coating.

2. The absorbent structure of claim 1, wherein the film coating is a heat-treated or annealed film coating.

3. The absorbent structure of claim 1, wherein the water-absorbing particles are post-crosslinked.

4. The absorbent structure of claim 1, wherein the elastic film-forming polymer is a polyurethane.

5. The absorbent structure of claim 1, wherein the elastic film-forming polymer is a polyurethane dispersion blended with at least one polymer dispersion selected from the group consisting of poly-co(ethylene-vinylacetate), polyacetale and homo- and copolymers comprising acrylonitrile, butadiene, styrene, (meth-)acrylate, isoprene, or vinylpyrrolidone.

6. The absorbent structure of claim 1, wherein the coalescing agent is an alcohol.

7. The absorbent structure of claim 6, wherein the coalescing agent is a butanol.

8. The absorbent structure of claim 1, wherein the film-coating comprises an antioxidant and/or a deagglomerating aid.

9. The absorbent structure of claim 1, wherein the film coating is homogeneous.

10. The absorbent structure of claim 1, comprising an absorbent core that comprises the water-absorbing material and less than 20% by weight of fibrous absorbent material based on the weight of the water-absorbing material.

11. The absorbent structure of claim 10, wherein the absorbent core comprises adhesive or thermoplastic material.

* * * * *